United States Patent
Paczkowski et al.

(10) Patent No.: US 11,066,689 B2
(45) Date of Patent: *Jul. 20, 2021

(54) ANALYSIS AND SCREENING OF CELL SECRETION PROFILES

(71) Applicant: IsoPlexis Corporation, Branford, CT (US)

(72) Inventors: Patrick Paczkowski, Branford, CT (US); Sean MacKay, Branford, CT (US); Sean McCusker, Branford, CT (US)

(73) Assignee: IsoPlexis Corporation, Branford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/773,535

(22) Filed: Jan. 27, 2020

(65) Prior Publication Data

US 2020/0239926 A1    Jul. 30, 2020

Related U.S. Application Data

(63) Continuation of application No. 15/532,428, filed as application No. PCT/US2015/063754 on Dec. 3, 2015, now Pat. No. 10,584,366.

(Continued)

(51) Int. Cl.
*G06T 7/30* (2017.01)
*G01N 21/64* (2006.01)
(Continued)

(52) U.S. Cl.
CPC .............. *C12Q 1/00* (2013.01); *B01L 3/5085* (2013.01); *B01L 3/502761* (2013.01);
(Continued)

(58) Field of Classification Search
CPC .......... G06T 7/0012; G06T 7/30; G06T 7/33; G06T 7/337; G06T 2207/30024;
(Continued)

(56) References Cited

U.S. PATENT DOCUMENTS

| 5,858,801 A | 1/1999 | Brizzolara ..................... 436/518 |
| 6,039,897 A | 3/2000 | Lockhead et al. ........... 264/1.24 |

(Continued)

FOREIGN PATENT DOCUMENTS

| CN | 102690786 | 9/2012 | ............. C12N 15/10 |
| DE | 10127221 A1 | 11/2002 | ............. G01N 33/48 |

(Continued)

OTHER PUBLICATIONS

Adams et al. (2008) "Multitarget magnetic activated cell sorter", Proc Natl Acad Sci USA. , 105(47):18165-18170.

(Continued)

*Primary Examiner* — Andrew W Johns
(74) *Attorney, Agent, or Firm* — Cooley LLP

(57) ABSTRACT

Embodiments disclose apparatus, methods and software for performing biological screening and analysis implemented using an instrument platform capable of detecting a wide variety of cell-based secretions, expressed proteins, and other cellular components. The platform may be configured for simultaneous multiplexed detection of a plurality biological components such that a large number of discrete samples may be individually sequestered and evaluated to detect or identify constituents from the samples in a highly parallelized and scalable manner.

20 Claims, 39 Drawing Sheets

Related U.S. Application Data

(60) Provisional application No. 62/087,147, filed on Dec. 3, 2014.

(51) Int. Cl.
   | | |
   |---|---|
   | *C12Q 1/00* | (2006.01) |
   | *G01N 33/543* | (2006.01) |
   | *B01L 3/00* | (2006.01) |
   | *C12M 1/34* | (2006.01) |
   | *G06T 7/13* | (2017.01) |

(52) U.S. Cl.
   CPC ......... *C12M 41/46* (2013.01); *G01N 21/6452* (2013.01); *G01N 33/543* (2013.01); *G06T 7/13* (2017.01); *G06T 7/30* (2017.01); *B01L 2200/0668* (2013.01); *G06T 2207/10064* (2013.01); *G06T 2207/30024* (2013.01); *G06T 2207/30204* (2013.01)

(58) Field of Classification Search
   CPC ........... G06T 2207/30072; G06T 2207/30204; C12Q 1/00; C12M 41/46; G01N 21/6452; G01N 21/6486
   See application file for complete search history.

(56) References Cited

U.S. PATENT DOCUMENTS

| | | | |
|---|---|---|---|
| 6,165,739 A | 12/2000 | Clatch | 435/29 |
| 6,377,721 B1 | 4/2002 | Walt et al. | 385/12 |
| 6,429,027 B1 | 8/2002 | Chee et al. | 436/518 |
| 6,524,790 B1 | 2/2003 | Kopf-Sill et al. | 435/6 |
| 6,699,665 B1 | 3/2004 | Kim et al. | 435/6 |
| 6,924,153 B1 | 5/2005 | Boehringer et al. | 436/514 |
| 7,312,197 B2 | 12/2007 | Gong et al. | 514/12 |
| 7,381,375 B2 | 6/2008 | Ravkin et al. | 422/102 |
| 8,105,845 B2 | 1/2012 | Notcovich et al. | 436/518 |
| 8,394,590 B2 | 3/2013 | Kwong et al. | 435/6.12 |
| 8,460,878 B2 | 6/2013 | Walt et al. | 435/7.1 |
| 8,492,165 B2 | 7/2013 | Van Pelt et al. | 436/180 |
| 8,865,479 B2 * | 10/2014 | Love et al. | G01N 33/54366 436/548 |
| 9,188,586 B2 | 11/2015 | Fan et al. | G01N 33/54306 |
| 9,506,917 B2 | 11/2016 | Fan et al. | G01N 33/54306 |
| 9,824,870 B1 | 11/2017 | Straume et al. | H01J 49/0031 |
| 10,274,486 B2 | 4/2019 | Fan et al. | G01N 33/54366 |
| 10,584,366 B2 * | 3/2020 | Paczkowski et al. | G01N 21/6452 |
| 10,928,389 B2 | 2/2021 | Fan et al. | G01N 33/54393 |
| 2001/0016320 A1 | 8/2001 | He et al. | 435/6 |
| 2002/0090649 A1 | 7/2002 | Chan et al. | 435/7.1 |
| 2002/0100714 A1 | 8/2002 | Staats | 210/85 |
| 2002/0131974 A1 | 9/2002 | Segal | 424/184.1 |
| 2002/0146745 A1 | 10/2002 | Natan et al. | 435/7.1 |
| 2003/0013091 A1 | 1/2003 | Dmitrov | 435/6 |
| 2003/0082601 A1 | 5/2003 | Dill | 435/6 |
| 2003/0096232 A1 | 5/2003 | Kris et al. | 435/6 |
| 2003/0104486 A1 | 6/2003 | Selvan | 435/7.2 |
| 2003/0127610 A1 | 7/2003 | Gallagher | 250/574 |
| 2003/0190608 A1 | 10/2003 | Blackburn | 435/6 |
| 2003/0190689 A1 | 10/2003 | Crosby et al. | 435/7.23 |
| 2004/0092032 A1 | 5/2004 | Winkler et al. | 436/180 |
| 2004/0191124 A1 | 9/2004 | Noetzel et al. | 422/69 |
| 2004/0224321 A1 | 11/2004 | Nicolau et al. | 435/6 |
| 2004/0265889 A1 | 12/2004 | Durham et al. | 435/6 |
| 2005/0032144 A1 | 2/2005 | Lombardi et al. | 435/15 |
| 2005/0142033 A1 | 6/2005 | Glezer et al. | 422/58 |
| 2005/0197311 A1 | 9/2005 | Cooper et al. | 514/44 |
| 2005/0226779 A1 | 10/2005 | Oldham et al. | 422/99 |
| 2006/0246475 A1 | 11/2006 | Peterson et al. | 435/6 |
| 2006/0263818 A1 | 11/2006 | Scherer et al. | 435/6 |
| 2006/0286549 A1 | 12/2006 | Sohn et al. | 435/5 |
| 2007/0074972 A1 | 4/2007 | Nassef et al. | 204/451 |
| 2007/0122819 A1 | 5/2007 | Wu et al. | 435/6 |
| 2007/0202538 A1 | 8/2007 | Glezer et al. | 435/7.1 |
| 2008/0200343 A1 | 8/2008 | Clemens et al. | 506/9 |
| 2008/0207461 A1 | 8/2008 | Ermantraut et al. | 506/8 |
| 2008/0317627 A1 | 12/2008 | Shirai et al. | 422/52 |
| 2009/0017455 A1 | 1/2009 | Kwong et al. | 435/6 |
| 2009/0036324 A1 * | 2/2009 | Fan et al. | B01L 3/502746 506/9 |
| 2009/0053732 A1 | 2/2009 | Vermesh et al. | 435/7.1 |
| 2009/0137413 A1 | 5/2009 | Mehta et al. | 506/9 |
| 2009/0227043 A1 | 9/2009 | Huang | 436/501 |
| 2010/0009335 A1 | 1/2010 | Joseph et al. | 435/3 |
| 2010/0152054 A1 | 6/2010 | Love et al. | 506/9 |
| 2010/0297145 A1 | 11/2010 | Tsujikawa et al. | 424/172.1 |
| 2011/0034908 A1 | 2/2011 | Hyde et al. | 604/891.1 |
| 2011/0048952 A1 | 3/2011 | Van Pelt et al. | 204/600 |
| 2011/0177537 A1 | 7/2011 | Nissum et al. | 435/7.93 |
| 2012/0015824 A1 | 1/2012 | Love et al. | 506/3 |
| 2012/0156675 A1 | 6/2012 | Lueerssen et al. | 435/6.11 |
| 2013/0338047 A1 | 12/2013 | Love et al. | G01N 33/577 |
| 2014/0170642 A1 | 6/2014 | Huang et al. | G01N 33/54306 |
| 2014/0307931 A1 * | 10/2014 | Gierahn et al. | G06T 7/11 382/128 |
| 2015/0078999 A1 | 3/2015 | Heath et al. | C07K 7/64 |
| 2015/0086424 A1 | 3/2015 | Putnam et al. | G01N 33/54366 |
| 2015/0204862 A1 | 7/2015 | Fan et al. | G01N 33/54306 |
| 2015/0204864 A1 | 7/2015 | Fan et al. | G01N 33/54386 |
| 2016/0129445 A1 | 5/2016 | Corey et al. | B01L 7/52 |
| 2016/0167049 A1 | 6/2016 | Narahara et al. | B01L 3/502715 |
| 2016/0238594 A1 | 8/2016 | Xue et al. | G01N 33/5308 |
| 2017/0067887 A1 | 3/2017 | Fan et al. | G01N 33/54366 |
| 2017/0138942 A1 | 5/2017 | Fan et al. | G01N 33/54393 |
| 2018/0105855 A1 | 4/2018 | Paczkowski et al. | C12Q 1/00 |
| 2019/0195869 A1 | 6/2019 | Fan et al. | G01N 33/54393 |
| 2019/0285626 A1 | 9/2019 | Ng et al. | G01N 33/54386 |
| 2019/0324028 A1 | 10/2019 | Fan et al. | G01N 33/54366 |
| 2019/0376898 A1 | 12/2019 | Tsiomplikas et al. | G01N 21/6458 |
| 2020/0166518 A1 | 5/2020 | Mackay et al. | G01N 33/68 |
| 2020/0239926 A1 | 7/2020 | Paczkowski et al. | C12Q 1/00 |

FOREIGN PATENT DOCUMENTS

| | | | | |
|---|---|---|---|---|
| EP | 1816476 A1 | 8/2007 | | G01N 33/68 |
| EP | 2 336 348 A1 | 6/2011 | | C12Q 1/02 |
| JP | 2010-066146 A | 3/2010 | | G01N 33/543 |
| WO | WO 96/28538 A1 | 9/1996 | | C12M 1/00 |
| WO | WO 02/077259 A2 | 10/2002 | | |
| WO | WO 2003/048736 A2 | 6/2003 | | |
| WO | WO 2005/007892 A1 | 1/2005 | | C12Q 1/68 |
| WO | WO 2005/081867 A2 | 9/2005 | | |
| WO | WO 2005/090972 A1 | 9/2005 | | G01N 33/53 |
| WO | WO 2006/117541 A1 | 11/2006 | | C12M 1/33 |
| WO | WO 2007/014267 A2 | 2/2007 | | H01L 21/00 |
| WO | WO 2007/035633 A2 | 3/2007 | | G01N 33/53 |
| WO | WO 2008/016680 A1 | 2/2008 | | C12Q 1/68 |
| WO | WO 2009/012340 A2 | 1/2009 | | C12M 1/34 |
| WO | WO 2009/012343 A2 | 1/2009 | | C12M 1/34 |
| WO | WO 2010/065929 A2 | 6/2010 | | G01N 33/53 |
| WO | WO 2013/090404 A2 | 6/2013 | | C12Q 1/68 |
| WO | WO 2013/148448 A1 | 10/2013 | | G01N 33/574 |
| WO | WO 2014/031997 A1 | 2/2014 | | C12M 1/34 |
| WO | WO 2014/052989 A2 | 4/2014 | | G01N 33/543 |
| WO | WO 2016/057552 A1 | 4/2016 | | C12Q 1/68 |
| WO | WO 2016/057705 A1 | 4/2016 | | G01N 33/574 |
| WO | WO 2016/090148 A1 | 6/2016 | | G01N 33/543 |
| WO | WO 2016/090320 A1 | 6/2016 | | C12N 5/07 |

OTHER PUBLICATIONS

Adler et al. (2005) "Detection of femtogram amounts of biogenic amines using self-assembled DNA-protein nanostructures," Nature Methods, 2(2):147-149.

Amir et al., (2013) "viSNE enables visualization of high dimensional single-cell data and reveals phenotypic heterogeneity of leukemia", Nat Biotechnol., 31(6):545-52.

(56) References Cited

OTHER PUBLICATIONS

Anderson et al. (2002) "The human plasma proteome: history, character, and diagnostic prospects," Mol. Cell. Proteomics, 1:845-867.
Arenkov et al. (2000) "Protein microchips: use for immunoassays and enzymatic reactions," Anal. Biochem., 278:123-131.
Armstrong et al. (2000) "Suspension arrays for high throughput, multiplexed single nucleotide polymorphism genotyping," 40(2):102-108.
Ashton et al. (1973) "Smoking and carboxhemoglobin," Lancet. 2:857-858.
Balaban et al., (2004) "Bacterial persistence as a phenotypic switch", Science, 305(5690): 1622-5.
BD Biosciences (2007) "Purified Mouse Anti-Human IL-2," Accessible on the Internet at URL: http://www.bdbiosciences.com/ptProduct.jsp?prodid=6725.
BD Pharmingen (2003) "Technical data sheet: Purified mouse anti-human IL-2 monoclonal antibody (ELISA capture)," BD Biosciences. Accessible on the Internet at URL: http://www.bdbiosciences.com/ds/pm/tds/555051.pdf.
Becker et al. (2005) "Direct readout of protein-protein interactions by mass spectrometry from protein-DNA microarrays," Angew. Chemie. Int. Ed. 44:7635-7639.
Bendall et al., (2012) "From single cells to deep phenotypes in cancer", Nat Biotechnol., 30(7):639-47.
Bendall et al., (2011) "Single-cell mass cytometry of differential immune and drug responses across a human hematopoietic continuum", Science, 332(6030):687-96.
Bernard et al. (2001) "Micromosaic immunoassays," Analytical Chemistry. 73:8-12.
Betensky et al. (2002) "Influence of unrecognized molecular heterogeneity on randomized clinical trials," J. Clin. Oncol. 20:2495-2499.
Boozer et al. (2004) "DNA directed protein immobilization on mixed ssDNA/oligo(ethylene glycol) self-assembled monolayers for sensitive biosensors," Anal. Chem. 76:6967-6972.
Boozer et al. (2006) "DNA-Directed Protein Immobilization for Simultaneous Detection of Multiple Analytes by Surface Plasmon Resonance Biosensor," Analytical Chemistry. 78:1515-1519.
Breslauer et al. (2006) "Microfluidic-based systems biology," Mol. Biosyst. 2:97-112.
Bunimovich et al. (2006) "Quantitative Real-Time Measurements of DNA Hybridization with Alkylated Nonoxidized Silicon Nanowires in Electrolyte Solution," J. Am. Chem. Soc. 128:16323-16331.
Chattopadhyay, P. et al. (2014) "Single-cell technologies for monitoring immune systems," Nature Immunology, 15(2):128-135.
Chen et al. (2002) "Discordant protein and mRNA expression in lung adenocarcinomas," Mol. Cell. Proteomics. 1:304-313.
Chen et al. (2004) "Plasma proteome of severe acute respiratory syndrome analyzed by two-dimensional gel electrophoresis and mass spectrometry," Proc. Natl. Acad. Sci. USA. 101:17039-17044.
Chen et al. (2005) "Marked Differences in Human Melanoma Antigen-Specific T Cell Responsiveness after Vaccination Using a Functional Microarray," PLoS Medicine, 2(10):1018-1030.
Chen et al., (2007) "Multiplexed analysis of glycan variation on native proteins captured by antibody microarrays", Nat Methods, 4(5):437-44.
Chen X. et al. (2012) "Microfluidic Devices Targeting Blood Cell Lysis", On-Chip Pretreatment of Whole Blood by Using MEMS Technology, p. 64-83.
Cheong et al. (2009) "Using a microfluidic device for high-content analysis of cell signaling", Sci Signal, 2(75), p12.
Choi et al., (2011) "Immuno-hybridization chain reaction for enhancing detection of individual cytokinesecreting human peripheral mononuclear cells", Anal Chem, 83(17):6890-5.
Chou et al. (2000) "Sorting biomolecules with microdevices," Electrophoresis. 21:81-90.
Coussens et al. (2002) "Inflammation and cancer," Nature. 420:860-867.

Crowley et al. (2005) "Isolation of plasma from whole blood using planar microfilters for lab-on-a-chip applications," Lab on a Chip. 5:922-929.
Dandy et al. (2007) "Array feature size influences nucleic acid surface capture in DNA microarrays," Proc Natl. Acad. Sci. USA, 104:8223-8228.
Das S. et al., (2015) "A General Synthetic Approach for Designing Epitope Targeted Macrocyclic Peptide Ligands", Angewandte Chemie, 54:13219-13224.
De Marzo et al. (2007) "Inflammation in prostate carcinogenesis," Nature Reviews Cancer. 7:256-269.
Degenaar et al. (2001) "A method for micrometer resolution patterning of primary culture neurons for SPM analysis,"J. Biochem. 130:367-376.
Dehqanzada et al. (2005) "Assessing serum cytokine profiles in breast cancer patients receiving a HER2/neu vaccine using Luminex technology," Annals of Surgical Oncology, 12:S47-S48.
Delamarche et al. (1997) "Patterned delivery of immunoglobulins to surfaces using microfluidic networks," Science, 76:779-781.
Deyle, Kaycie M. et al. (2015) "Protein-targeting strategy used to develop a selective inhibitor of the E17K point mutation in the PH domain of Akt1"; Nat. Chem., 7(5), p. 455-462.
Dirks et al. (2004) "Paradigms for computational nucleic acid design," Nucleic Acids Research. 32(4):1392-1403.
Downward, J., (2003) "Targeting RAS Signalling Pathways in Cancer Therapy", Nature Reviews, vol. 3, 22 pages.
Elitas, Meltem et al. (2014) "A microchip platform for interrogating the single-cell level", Lab on a Chip, vol. 14, No. 18, p. 3582.
Engvall et al. (1972) "Enzyme-linked immunosorbent assay, Elisa. 3. Quantitation of specific antibodies by enzymeabeled anti-immunoglobulin in antigen-coated tubes," J. lmmunol. 109:129-135.
Erickson et al. (2003) "Modeling of DNA hybridization kinetics for spatially resolved biochips," Anal. Biochem. 317:186-200.
Eyer K. et al. (2013) "Implementing Enzyme-Linked Immunosorbent Assays on a Microfluidic Chip To Quantify Intracellular Molecules in Single Cells", Analytical Chemistry, vol. 85, No. 6, pp. 3280-3287.
Fainerman et al. (1998) "Adsorption of surfactants and proteins at fluid interfaces," Colloids and Surfaces, 143:141-165.
Fan et al., (2008) "Integrated barcode chips for rapid, multiplexed analysis of proteins in microliter quantities of blood", Nature Biotechnology, vol. 26, p. 1373-1378.
Fan et al., (2008) "Integrated blood barcode chips", Nature Biotechnology, vol. 26, No. 12, p. 1373-1378.
Fuji et al. (2005) "Clinical-scale high-throughput human plasma proteome analysis: lung adenocarcinoma," Droteomics. 5:1150-1159.
Fung (1973) "Stochastic flow in capillary blood vessels," Microvasc. Res. 5:34-38.
Galbraith, W. et al. (1993) "Remapping disparate images for conincidence", Journal of Microscopy, vol. 172, No. 2, pp. 163-176.
Gorelik et al. (2005) "Multiplexed immunobead-based cytokine profiling for early detection of ovarian cancer," Cancer Epidemiol. Biomarkers Prev. 14:981-987.
Green et al. (2006) "Capturing the uncultivated majority", Current Opinion in Biotechnology, 17(3), p. 250-255.
Groves et al. (1995) "In vitro maturation of clonal CD4+CD8+ cell lines in response to TCR engagement," J. Immunol. 154:5011-5022.
Guan et al. (2004) "Recombinant protein-based enzyme-linked immunosorbent assay and immunochromatographic tests for detection of immunoglobulin G antibodies to severe acute respiratory syndrome (SARS) coronavirus in SARS patients," Clinical and Diagnostics Laboratory Immunology, 11(2):287-291.
Hainfeld et al. (2002) "Silver and Gold-Based Autometallography of Nanogold," Ch. 3, Gold and Silver Staining, CRC Press. Washington, DC. pp. 29-46.
Han et al., (2010) "Multidimensional analysis of the frequencies and rates of cytokine secretion from single cells by quantitative microengraving", Lab Chip, 10(11):1391-400.
Han et al., (2012) "Polyfunctional responses by human T cells result from sequential release of cytokines", Proc Natl Acad Sci USA, 109(5):1607-12.

(56) References Cited

OTHER PUBLICATIONS

Heath et al. (2007) "Nanotechnology and cancer," Annual Review of Medicine. 59:251-265.
Henshall et al. (2007) "Assay: Validating biomarkers with VeraCode", Genet Eng Biotechnol News, 27(17): 1-3.
Holland et al. (1991) "Detection of specific polymerase chain reaction product by utilizing the 5'-3' exonuclease activity of Thermus aquaticus DNA polymerase" Proc. Natl. Acad. Sci. USA. 88:7276-7280.
Hong et al. (2003) "Integrated nanoliter systems," Nature Biotechnology, 21:1179-1183.
Hong et al. (2004) "A nanoliter-scale nucleic acid processor with parallel architecture," Nature Biotechnology, 22 (4):435-439.
Hsieh et al. (2006) "Systematical evaluation of the effects of sample collection procedures on low-molecular-weight serum/plasma proteome profiling," Proteomics. 6:3189-3198.
Huang et al. (2001) "Detection of multiple proteins in an antibody-based protein microarray system," Journal of Immunological Methods. 255:1-13.
Huang et al. (2004) "Continuous particle separation through deterministic lateral displacement," Science, 304:987-990.
Huang et al. (2007) "Counting low-copy number proteins in a single cell," Science. 315:81-84.
Huber et al. (2004) "Comparison of proteomic and genomic analyses of the human breast cancer cell line T47D and the antiestrogen-resistant derivative T47D-r," Molec. Cell. Proteomics. 3:43-55.
Hughes et al. (2003) "Molecular Monitoring of Chronic Myeloid Leukemia," Seminars in Hematology, 40(2):62-68.
Hughes, A. et al. (2014) "Single-cell western blotting", Nat Methods, 1(7):749-55.
Iannone et al. (1999) "Multiplexed single nucleotide polymorphism genotyping by oligonucleotide ligation and flow cytometry," Cytometry. 39(2):131-140.
Inerowicz et al. (2002) "Multiprotein immunoassay arrays fabricated by microcontact printing," Langmuir, 18:5263-5268.
Ivanova et al. (2002) "Polymer Microstructures Fabricated via Laser Ablatoin Used for Multianalyte Protein Microassay", Langmuir, vol. 18, p. 9539-9546.
Jeon et al. (1991) "Protein-surface interactions in the presence of polyethylene oxide: II. Effect of protein size," Journal of Colloid and Interface Science. 142(1):159-166.
Kim et al. (1979) "Establishment and characterization of BALB/c lymphoma lines with B cell properties," J. Immunol. 122:549-554.
Kiyonaka et al. (2004) "Semi-wet peptide/protein array using supramolecular hygrogel," Nature Materials. 3:58-64.
Kochenderfer et al. (2012) B-cell depletion and remissions of malignancy along with cytokine-associated toxicity in a clinical trial of anti-CD19 chimeric-antigen-receptor-transduced T-cells Blood, vol. 119, No. 12, p. 2709-2720.
Kozlov et al. (2004) "Efficient strategies for the conjugation of oligonucleotides to antibodies enabling highly sensitive protein detection," Biopolymers. 73:621-630.
Krzywinski M. et al. (2009) "Circos: An information aesthetic for comparative genomics"; Genome Res., 19, p. 1639-1645.
Kwak, M. et al. (2013) "Single-cell protein secretomic signatures as potential correlates to tumor cell lineage evolution and cell-cell interaction", Frontiers in Oncology, 3, Art. 10, p. 1-8.
Kwon et al. (2004) "Antibody arrays prepared by cutinase-mediated immobilization on self-assembled monolayers,"Anal Chem. 76:5713-5720.
Kwong et al. (2005) "Synchronous global assessment of gene and protein expression in colorectal cancer progression," Genomics. 86:142-158.
Lamb et al. (2006) "The Connectivity Map: using gene-expression signatures to connect small molecules, genes, and disease," Science. 313(5795):1929-1935.
Lambeck et al. (2007) "Serum cytokine profiling as a diagnostic and prognostic tool in ovarian cancer: a potential role or interleukin 7," Clinical Cancer Research, 13:2385-2391.
Lange et al. (2004) "Microcontact printing of DNA molecules," Analytical Chemistry. 76:1641-1647.
Lathrop (2003) "Therapeutic potential of the plasma proteome," Current Opinion in Molecular Therapeutics, 5:250-257.
Lecault et al., (2011) "High-throughput analysis of single hematopoietic stem cell proliferation in microfluidic cell culture arrays", Nat Methods, 8(7):581-586.
Lee et al. (2001) "SPR Imaging Measurements of 1-D and 2-D DNA Microarrays Created from Microfluidic Channels on Gold Thin Films," Analytical Chemistry, 73(22):5525-5531.
Lee et al., (2012) "Quantitative and dynamic assay of single cell chemotaxis", Integr Biol (Camb). 4(4):381-390.
Lin et al. (2005) "Evidence for the Presence of Disease-Perturbed Networks in Prostate Cancer Cells by Genomic and Droteomic Analyses: A Systems Approach to Disease," Cancer Res. 65:3081-3091.
Lin et al. (2007) "A cytokine-mediated link between innate immunity, inflammation, and cancer," Journal of Clinical Investigation. 117:1175-1183.
Liotta et al. (2003) "Protein microarrays: meeting analytical challenges for clinical applications", Cancer Cell, 3(4):317-325.
Liu et al. (2000) "Photopatterning of antibodies on biosensors," Bioconjugate Chem. 11:755-761.
Love et al. (2006) "A microengraving method for rapid selection of single cells producing antigenspecific antibodies", Nat Biotechnol, 24(6):703-707.
Lu, Yao et al. (2013) "High-Throughout Secretomic Analysis of Single Cells to Assess Functional Cellular Heterogeneity", vol. 85, No. 4, pp. 2548-2556.
Ma, Chao et al. (2011) "A clinical microchip for evaluation of single immune cells reveals phenotypically similar T cells", Nature Medicine, vol. 17, No. 6, pp. 738-743.
MacBeath et al. (2000) "Printing proteins as microarrays for high-throughput function determination," Science, 289:1760-1763.
Madoz-Gurpide et al. (2001) "Protein based microarrays: A tool for probing the proteome of cancer cells and issues," Proteomics, 1(10):1279-1287.
Martin et al. (2006) "Molecular biology of breast cancer," Clin. Trans. Oneel. 8(1):7-14.
Mellinghoff et al. (2006) "Molecular determinants of the response of glioblastomas to EGFR kinase inhibitors," N. Engl. J. Med. 353:2012-2024.
Michel et al. (2002) "Printing meets lithography: Soft approaches to high-resolution patterning," Chimia. 56:527-542.
Michor et al. (2010) "The origins and implications of intratumor heterogeneity", Cancer Prev Res (Phila), 3(11):1361-1364.
Mischel et al. (2004) "DNA-microarray analysis of brain cancer: molecular classification for therapy," Nature Rev. Neurosci. 5:782-794.
Nagrath et al. (2007) "Isolation of rare circulating tumour cells in cancer patients by microchip technology," Nature, 450:1235-1239.
Nam et al. (2003) "Nanoparticle-based bio-bar codes for the ultrasensitive detection of proteins," Science, 301:1884-1886.
Nam et al. (2003) "Nanoparticle-based bio-bar codes for the ultrasensitive detection of proteins," Science, 301:1884-1886,—Supporting Material pp. 1 to 12.
Nathanson et al. (2014) "Co-targeting of convergent nucleotide biosynthetic pathways for leukemia eradication", J. Exp. Med., vol. 211(3), p. 473-486.
Niemeyer (2007) "Functional devices from DNA and proteins," Nano Today, 2:42-52.
Niemeyer et al. (2005) "lmmuno-PCR: high sensitivity detection of proteins by nucleic acid amplification," Trends in Biotechnology, 23:208-216.
Ostrem, J.M. et al. (2013) "K-Ras(G12C) inhibitors allosterically control GTP affinity and effector interactions", Nature, vol. 503, 14 pages.
Ottesen et al. (2006) "Microfluidic digital PCR enables multigene analysis of individual environmental bacteria," Science, 314:1464-1467.
Pal et al. (2006) "Differential Phosphoprotein Mapping in Cancer Cells Using Protein Microarrays Produced from 2-D Liquid Fractionation," Anal. Chem. 78:702-710.

(56) References Cited

OTHER PUBLICATIONS

Park et al. (2002) "Array-Based Electrical Detection of DNA with Nanoparticle Probes," Science. 295:1503-1506.
Peluso et al. (2003) "Optimizing antibody immobilization strategies for the construction of protein arrays," Anal. Biochem. 312:113-124.
Phillips (2004) "Rapid analysis of inflammatory cytokines in cerebrospinal fluid using chip-based immunoaffinity electrophoresis," Electrophoresis. 25:1652-1659.
Pirrung (2002) "How to make a DNA chip," Angew. Chem. Int. Ed. 41:1276-1289.
Prados et al. (2003) "Temozolomide + OS1-774," Proc. Am. Soc. Clin. Oncology, 22:99.
Prime et al. (1991) "Self-assembled organic monolayers: model systems for studying adsorption of proteins at Urfaces," Science, 252:1164-1167.
Prime et al. (1993) "Adsorption of proteins onto surfaces containing end-attached oligo(ethylene oxide): a model system using self-assembled monolayers," J. Am. Chem. Soc.115(23):10714-10721.
Quake et al. (2000) "From Micro- to Nanofabrication with Soft Materials," Science, 290:1536-1540.
Radich et al. (2006) "Gene expression changes associated with progression and response in chronic myeloid leukemia," Proc. Natl. Acad. Sci. USA. 103(8):2794-2799.
Ramsden (1995) "Puzzles and Paradox in Protein Adsorption," J. Chem. Soc. Rev. 24:73-78.
Rich et al. (2004) "Phase II trial of gefitinib in recurrent glioblastoma," J. Clin.Oncology 22:133-142.
Rowat et al., (2009) "Tracking lineages of single cells in lines using a microfluidic device", Proc Natl Acad Sci USA, 106(43):18149-54.
Sachdeva et al., (2007) "Cytokine quantitation: technologies and applications", Front Biosci. M12:4682-95, Review.
Sano et al. (1992) "Immuno-PCR: very sensitive antigen detection by means of specific antibody-DNA conjugates," Science, 258:120-122.
Sarkar A. et al. (2014) "Microfluidic probe for single-cell analysis in adherent tissue culture", Nature Communications, vol. 5, 8 pages.
Schena et al. (1995) "Quantitative monitoring of gene expression patterns with a complementary DNA microarray," Science, 270:467-470.
Schubbert, S. et al. (2007) Hyperactive Ras in developmental disorders and cancer, Nature Reviews, vol. 7, 14 pages.
Schweitzer et al. (2002) "Multiplexed protein profiling on microarrays by rolling-circle amplification," Nature Biotechnology, 20:359-365.
Sedgwick H. et al. (2008) "Lab-on-a-chip technologies for proteomic analysis from isolated cells", A Journal of the Royal Society, vol. 5, No. 2, pp. S123-S130.
Shi Q. et al. (2011) "Single-cell proteomic chip for profiling intracellular signaling pathways in single tumor cells", Proceedings National Academy of Sciences PNAS, vol. 109, No. 2, pp. 419-424.
Shin Y. et al. (2010) "Chemistries for Patterning Robust DNA MicroBarcodes Enable Multiplex Assays of Cytoplasm Proteins from Single Cancer Cells", ChemPhysChem, vol. 11, No. 14, pp. 3063-3069.
Shin et al., (2011) "Protein signaling networks from single cell fluctuations and information theory profiling", Biophys J., 100(10):2378-86.
Sia et al. (2003) "Microfluidic devices fabricated in poly(dimethylsiloxane) for biological studies," Electrophoresis, 24:3563-3576.
Soen et al. (2003) "Detection and characterization of cellular immune responses using peptide-MHC microarrays," PLoS Biology, 1 (3):429-438.
Sorger, P. (2008) "Microfluidics closes in on point-of-care assays", Nature Biotechnology, vol. 26, p. 1345-1346.
Spiro et al. (2000) "A bead-based method for multiplexed identification and quantitation of DNA sequences using flow cytometry," 66(10):4258-4265.

Svanes et al. (1968) "Variations in small blood vessel hematocrits produced in hypthermic rats by micro-occlusion," Microvascular Research, 1:210-220.
Taton et al. (2000) "Scanometric DNA array detection with nanoparticle probes," Science, 289:1757-1760.
Thirumalapura et al. (2005) "Lipopolysaccharide microarrays for the detection of antibodies," Journal of Immunological Methods. 298:73-81.
Thorsen et al. (2002) "Microfluidic large-scale integration," Science. 298:580-584.
Thuillier et al. (2005) "Development of a low-cost hybrid Si/PDMS multi-layered pneumatic microvalve," Microsystem Technologies. 12(1):180-185.
Tian et al. (2004) "Integrated genomic and proteomic analyses of gene expression in mammalian cells," Mol. Cell. Proteomics. 3:960-969.
Toner et al. (2005) "Blood-on-a-chip," Annual Review of Biomedical Engineering. 7:77-103.
Toure, M. et al., (2016) "Small-Molecule PROTACS: New Approaches to Protein Degradation", Angew. Chem. Int. Ed., vol. 55, 9 pages.
Unger et al., (2000) "Monolithic microfabricated valves and pumps by multilayer soft lithography", Science, 288(5463): 113-6.
Van Duijn et al. (2002) "Detection of genetically modified organisms in foods by protein- and DNA-based techniques: bridging the methods," JAOAC Int. 85(3):787-791.
Wacker (2004) "DD1-microFIA-A readily configurable microarray-fluorescence immunoassay based on DNA-direcled immobilization of proteins," Chembiochem. 5:453-459.
Wang et al., (2010) "Single cell analysis: the new frontier in 'omics'", Trends Biotechnol., 28(6):281-90.
Wei et al., (2013) "Microchip platforms for multiplex single-cell functional proteomics with applications to immunology and cancer research", Genome Med., 5(8):75.
Wegner et al. (2003) "Fabrication of Histidine-Tagged Fusion Protein Arrays for Surface Plasmon Resonance maging Studies of Protein-Protein and Protein-DNA Interactions," Analytical Chemistry. 75:4740-4746.
Whitesides et al. (2001) "Soll lithography in biology and biochemistry," Annual Review of Biomedical Engineering, 3:335-373.
Wysocki et al. (1978) "Panning for lymphocytes: a method for cell selection," Proc. Nall. Acad. Sci. USA. 75(6):2844-2848.
Yamanaka Y. J. et al. (2012) "Single-cell analysis of the dynamics and functional outcomes of interactions between human natural killer cells and target cells" Integrative Biology, vol. 4, No. 10, p. 1175-1184.
Yang et al. (2006) "A microfluidic device for continuous, real lime blood plasma separation," Lab on a Chip, 5:871-880.
Yang et al., (2007) "Using a cross-flow microfluidic chip and external crosslinking reaction for monodisperse TPP-chitosan microparticles", Sensors and Acuators, 124:510-516.
Yu et al. (2005) "Contextual interactions determine whether the Drosophila homeodomain protein, Vnd, acts as a repressor or activator," Nucleic Acids Research. 33(8):1-11.
Yu Y. et al. (2015) "Analysis of the surface, secreted, and intracellular proteome of Propionibacterium acnes", EUPA Open Proteonomics, vol. 9, pp. 1-7.
Yu J. et al. (2014) "Microfluidics-Based Single-Cell Functional Proteomics for Fundamental and Applied Biomedical Applications," Annual Review of Analytical Chemistry, vol. 7, p. 275-295.
Zhang, K. et al. (2006) "Sequencing genomes from single cells by polymerase cloning", Nature Biotechnology 24(6):680-686.
Zhao et al. (2007) "High-Affinity TCRs Generated by Phage Display Provide CD4$^+$ T Cells with the Ability to Recognize and Kill Tumor Cell Lines", The Journal of Immunology, vol. 179, No. 9, p. 5845-5854.
Zimmermann et al. (2005) "Modeling and optimization of high-sensitivity, low-volume microfluidic-based surface immunoassays," Biomedical Microdevices. 7(2):99-110.

* cited by examiner

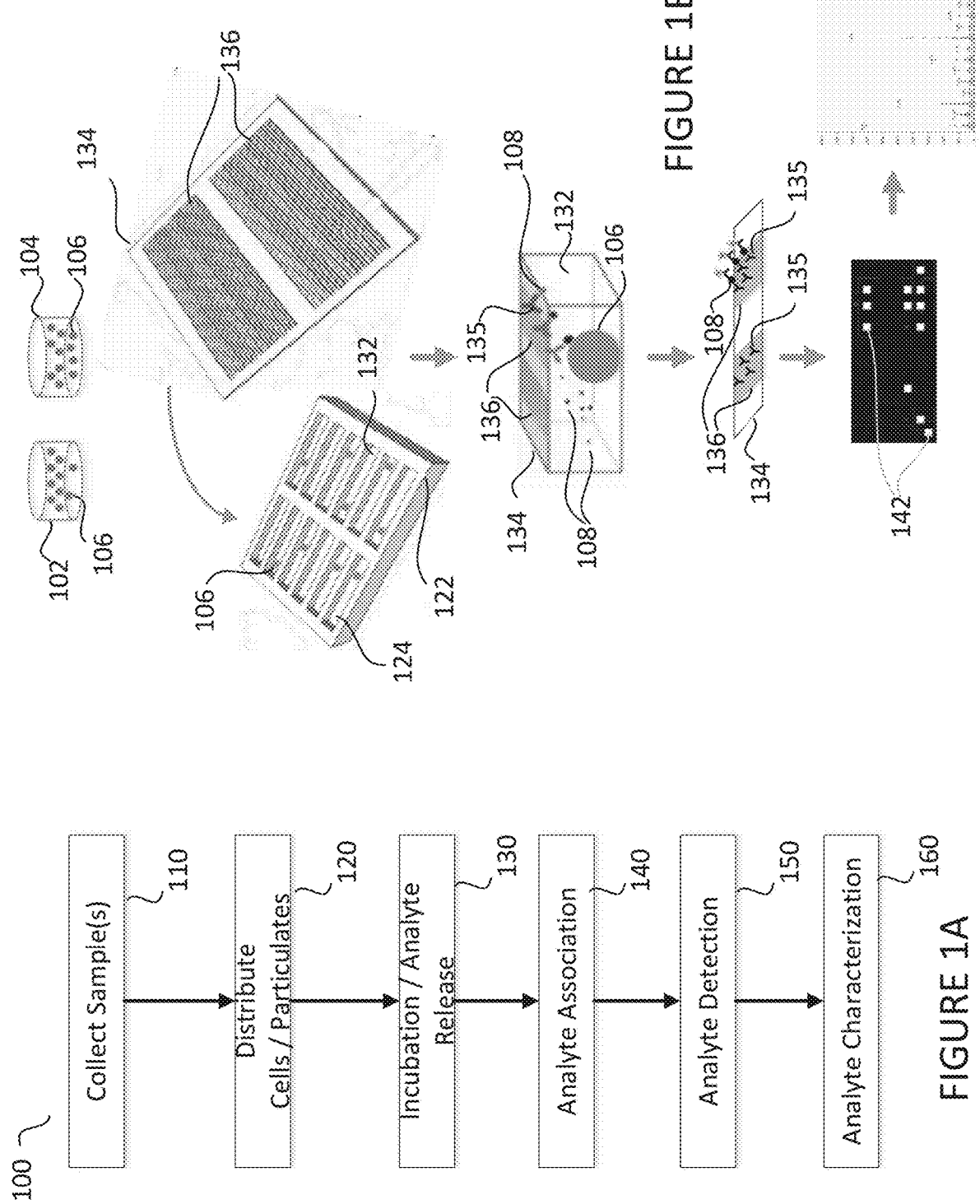

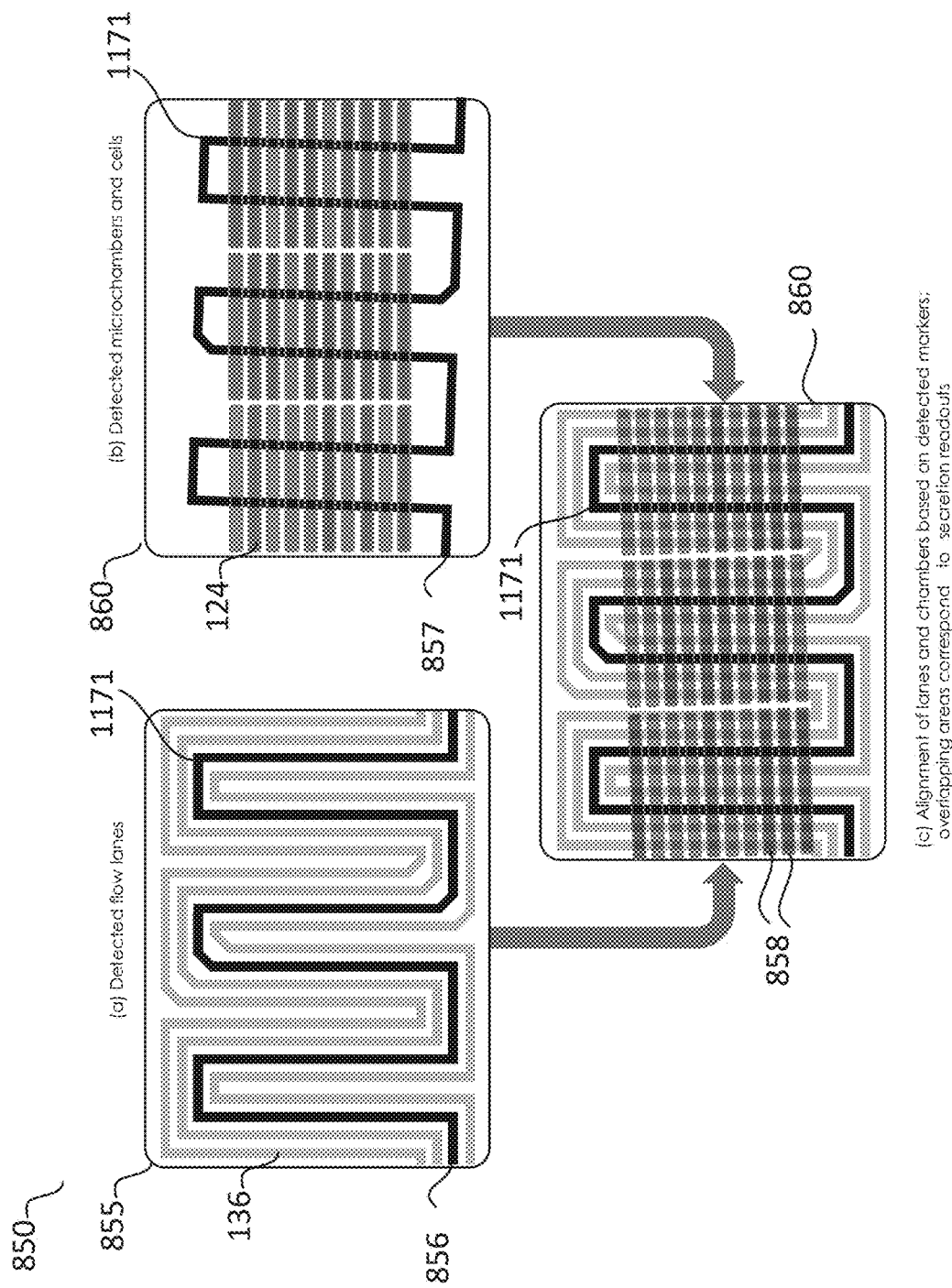

(c) Same chambers with both secretion barcodes overlaid. Note that each circled secretion corresponds to two distinct cytokines being secreted by the same cell, IFN-γ observed in wavelength 635 nM, and RANTES in wavelength 532 nM.

(a) Pie charts showing polyfunctionality percentages

26% confers a high probability CD4 functionality and proliferation readout. Poly-functionality of CD4+ T Cells secreting IFNg, Il-2 and TNF at the single-cell level are correlated with immune response, with respect to viral infections.

17% confers a medium probability CD4 functionality and proliferation readout.

(b) Bar graph displaying dominant polyfunctional groups in the sample
1810

(b) Heat map displaying dominant polyfunctional groups and secretion intensities
1815

ANALYSIS AND SCREENING OF CELL SECRETION PROFILES

CROSS REFERENCE TO RELATED APPLICATIONS

This application is a continuation application of U.S. patent application Ser. No. 15/532,428, filed Jun. 1, 2017, which is a National Stage Application, filed under 35 U.S.C § 371, of International Application No. PCT/US2015/063754 filed Dec. 3, 2015, which claims the benefit of priority to U.S. Provisional Patent Application Ser. No. 62/087,147 filed Dec. 3, 2014, the contents of each of which are incorporated by reference herein in their entirety.

FIELD OF THE DISCLOSURE

The present invention generally relates to cellular analysis, and more particularly to apparatus, methods, and software for biochemical assessment and functional characterization of cellular states.

BACKGROUND

In fields including cell biology and immunology, development of analytical techniques for evaluation and quantitation of cellular protein expression and secretion profiles is of significant importance to elucidate underlying biochemical processes and cell signaling mechanisms. Due in part to the heterogeneous behaviors often exhibited by cells, a need exists for tools and procedures capable of assaying large numbers of discrete cell populations that are also suitable for detection of biomolecules at the single cell level. Sensitive and accurate assessment of cellular phenotypes and functionalities as well as identification of drivers and interactions between individual cells have been shown to be important indicia of the capabilities and operation of biological systems.

As one example, immune cell response is directed by a large number of secreted proteins including cytokines, chemokines, and growth factors which represent important functional regulators mediating a range of cellular behaviors and cell-cell signaling processes. Monitoring these complex immuno-signaling pathways and cellular interactions present significant challenges to identifying clinically relevant measurements that can be used to understand that state of the immune system, predict clinical outcomes, and direct treatment or therapies. Increasingly, there is a demand for sensitive and highly-multiplexed technologies for cellular analysis that can be used to identify and rapidly evaluate correlatives of disease, cellular responses to various chemicals and therapeutic agents, and other cell-based processes involved in immunological interventions. Such technologies can also be used to better understand the underlying mechanisms of immunity.

SUMMARY OF THE DISCLOSURE

The present disclosure provides apparatus, methods and software useful for determining and investigating cellular processes and functional profiles. In various embodiments, the present teachings may be advantageously applied in the context of cellular analysis of immune cells. For example, T-cell functionality and correlative response to various therapies, chemical interactions and/or disease states may be assessed at the single cell level.

In various embodiments, apparatus, methods and software are disclosed for performing biological screening and analysis implemented using an instrument platform capable of detecting a wide variety of cell-based secretions, expressed proteins, and other cellular components. The platform may be configured for simultaneous multiplexed detection of a plurality of biological components such that a large number of discrete samples may be individually sequestered and evaluated to detect or identify constituents from the samples in a highly parallelized and scalable manner. In various embodiments, the platform is configured for automated or semi-automated processing significantly improving time-to-result, sample throughput, detection accuracy, and sensitivity.

The platform may be advantageously adapted for use in applications to analyze small numbers of cells and single cells. As disclosed herein, analysis of single cells and cellular interactions between single cells (e.g. cell-cell interactions) is particularly useful in immunological applications to aid in the determination of functional profiles for immuno cells such as B-cells, T cells (e.g. CD4+, CD8+ cells), and/or macrophage cells. While various examples and workflows are provided and discussed involving immuno cells, it will be appreciated that the apparatus, methods and software of the present teachings may be adapted for use with a wide variety of different cell types. Furthermore, the sample analysis techniques may be extended outside of cellular or biological analysis applications to be used in other chemical surveys where multiple discrete samples are desirably evaluated substantially simultaneously for a plurality of different analytes. Additionally, sample constituents other than cells may be evaluated in parallel, for example, beads or other particles containing chemicals, compounds or other analytes of interest. In various embodiments, the technologies disclosed herein are sufficiently sensitive to detect, distinguish, and quantify multiple analytes present in very small liquid or aqueous volumes (for example, from nanoliter and picoliter volumes or less).

In various embodiments, a system is described for discretely resolving analytes associated with a cellular population comprising: (a) a plurality of sample retention regions that receive at least one cell distributed from a population of cells and retain an associated plurality of analytes released by the at least one cell; (b) a plurality of analyte detection regions patterned with a plurality of discretely positioned analyte detection moieties, the analyte detection regions disposed in an ordered pattern alignable with the sample retention regions whereby, upon coupling, released analytes selectively associate with the plurality of analyte detection moieties forming an analyte pattern for each analyte detection region; (c) a plurality of first alignment markers disposed about the plurality of sample retention regions and a plurality of second alignment markers disposed about the plurality of analyte detection regions; and (d) an imaging apparatus that generates a plurality of images for selected sample retention regions and retained at least one cell and additionally at least one first alignment marker, the imaging apparatus further generating a plurality of images for analyte detection regions corresponding to the selected sample regions and associated analyte patterns and additionally at least one second alignment marker; and an image processor that aligns associated images for selected sample retention regions using the at least one first alignment marker and further aligns images for analyte detection regions with corresponding images for selected sample retention regions using the at least one second alignment marker, the image processor further identifying retained at least one cell in respective sample retention regions and corresponding analyte patterns to discretely resolve released analytes associated with the retained at least one cell based on the analyte detection moieties detected in the analyte pattern.

In other embodiments, the a method is described for discretely resolving analytes associated with a cellular population comprising: (a) acquiring a plurality of images for a plurality of sample retention regions that receive at least one cell distributed from a population of cells and retain an associated plurality of analytes released by the at least one cell; (b) acquiring a plurality of images for a plurality of analyte detection regions patterned with a plurality of discretely positioned analyte detection moieties, the analyte detection regions disposed in an ordered pattern alignable with the sample retention regions whereby, upon coupling, released analytes selectively associate with the plurality of analyte detection moieties forming an analyte pattern for each analyte detection region; (c) resolving a plurality of first alignment markers disposed about the plurality of sample retention regions; (d) resolving a plurality of second alignment markers disposed about the plurality of analyte detection regions; (e) aligning associated images for selected sample retention regions using at least one of the plurality of first alignment markers and further aligning images for analyte detection regions with corresponding images for selected sample retention regions using the at least one of the plurality of second alignment markers; and (f) identifying retained at least one cell in respective sample retention regions and corresponding analyte patterns to discretely resolve released analytes associated with the retained at least one cell based on the analyte detection moieties detected in the analyte pattern.

In further embodiments, described is non-transitory computer-readable media having computer executable code stored thereon for discretely resolving analytes associated with a cellular population, the code comprising: (a) an executable routine for acquiring a plurality of images for a plurality of sample retention regions that receive at least one cell distributed from a population of cells and retain an associated plurality of analytes released by the at least one cell; (b) an executable routine for acquiring a plurality of images for a plurality of analyte detection regions patterned with a plurality of discretely positioned analyte detection moieties, the analyte detection regions disposed in an ordered pattern alignable with the sample retention regions whereby, upon coupling, released analytes selectively associate with the plurality of analyte detection moieties forming an analyte pattern for each analyte detection region; (c) an executable routine for resolving a plurality of first alignment markers disposed about the plurality of sample retention regions; (d) an executable routine for resolving a plurality of second alignment markers disposed about the plurality of analyte detection regions; (e) an executable routine for aligning associated images for selected sample retention regions using at least one of the plurality of first alignment markers and further aligning images for analyte detection regions with corresponding images for selected sample retention regions using the at least one of the plurality of second alignment markers; and (f) an executable routine for identifying retained at least one cell in respective sample retention regions and corresponding analyte patterns to discretely resolve released analytes associated with the retained at least one cell based on the analyte detection moieties detected in the analyte pattern.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims. It is to be understood that both the foregoing general description and the following detailed description are exemplary and explanatory only and are not restrictive of the scope of disclosed embodiments, as set forth by the claims.

BRIEF DESCRIPTION OF THE DRAWINGS

These and other embodiments of the disclosure will be discussed with reference to the following exemplary and non-limiting illustrations, in which like elements are numbered similarly, and where:

FIG. 1A depicts an exemplary high-level workflow for performing sample analysis according to the present disclosure.

FIG. 1B illustrates an exemplary high-level workflow for performing sample analysis according to the present disclosure.

FIG. 6A-1 and FIG. 6A-2 depicts an exemplary cell/particulate location identification process according to the present disclosure.

FIG. 8B illustrates an exemplary process for association and alignment of features according to the present disclosure.

FIG. 9A-1 and FIG. 9A-2 depicts an exemplary method for cell/particulate position identification and discrimination according to the present disclosure.

FIG. 10C-1 and FIG. 10C-2 illustrates an example of an imaging and pixel comparison process showing pairwise readouts associated with marker patterns for exemplary sample retention regions according to the present disclosure.

DETAILED DESCRIPTION

Figure 1C:
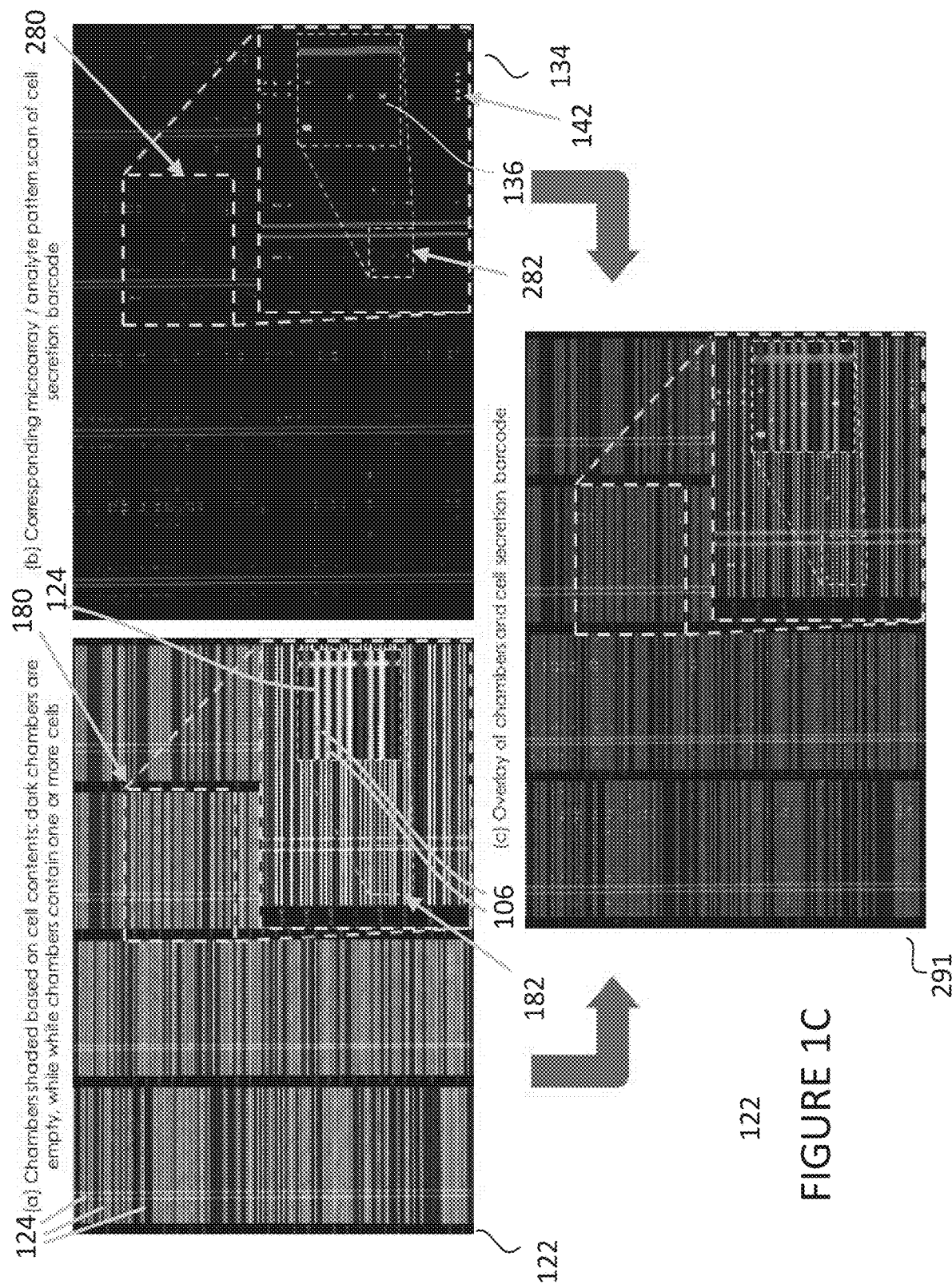
FIG. 1C depicts an exemplary sample array and an analyte detection substrate with magnified sub-portions according to the present disclosure.

Efforts to characterize the state or capabilities of a biological system or sample may be confounded or obscured by bulk analysis methods. This is evident in cellular analysis such as immunological surveys wherein a sample comprising many cells analyzed in a common volume or medium may act to mask or dilute analytes. It is therefore desirable in many instances to provide very small volume and single cell sample analysis capabilities. For small sample volumes including those involving a single or a few cells it is further desirable to sequester multiple samples in discrete reaction regions or areas so they may be subjected to parallel analysis. Such methods may require avoiding sample-to-sample cross-talk and contamination while providing the ability to subject the samples to uniform and discrete treatment. Collection of accurate and sensitive data in a scalable and multiplexed format with minimal user intervention is also important.

A particular example of a biochemical analysis particularly amenable to discrete cellular analysis relates to the evaluation of functional states based on secreted proteins from individual cells or arising from cell-to-cell interactions. In a model system comprising immune cell analysis, cell protein or chemical secretion profiles can be correlated with the quality of immune response at the single-cell level. For example, multiple cytokines may define or distinguish the differentiation stages in both CD4 and CD8 cell populations. Further, central memory and memory/effector cells may be associated with increased probabilities of secreting particular cytokines such as tumor necrosis factor alpha (TNF-α), interleukin 2 (IL2) and/or interferon gamma (IFN-γ). In contrast, cells that principally produce and secrete IFN-γ may be more likely to exhibit terminally differentiated effectors associated with programmed cell death (e.g. apoptosis).

To facilitate screening for a multiplicity of potential functional phenotypes such as those demonstrated in CD4 cells as well as to allow measurement of poly-functionality such as that associated with cellular immune response it is desirable to analyze multiple analytes simultaneously. For such analysis it is further desirable to enable detection of multiple analytes substantially simultaneously from individual or few numbers of cells where many hundreds, thousands, millions, or more discrete cells, samples, and/or discrete cellular interactions are evaluated for multiple analytes. Furthermore, the number of analytes that are screened for each cell or sample population may be between relatively few (for example between approximately 1-5 analytes) or more (for example between approximately 5 and 100 analytes) and perhaps even greater (for example more than 100 analytes) for each sample.

In a highly multiplexed system where many discrete samples may be desirably evaluated for many different analytes, a particular challenge arises in terms of quickly and accurately acquiring the associated data and performing high quality analysis. The small scale and large number of discrete samples to be simultaneously analyzed by such systems may make it impractical to perform these analyses adequately without a high degree of automation and/or user-independent computational analysis. This is particularly evident for developing single-cell technologies and cellular analysis systems intended to evaluate many hundreds, thousands or more discrete samples.

Exemplary single-cell analysis technologies have recently been described for example in "High-Throughput Secretomic Analysis of Single Cells to Assess Functional Cellular Heterogeneity" Analytical Chemistry, 2013, Volume 85, Pages 2548-2556, "Microfluidics-Based Single-Cell Functional Proteomics for Fundamental and Applied Biomedical Applications," Annual Review of Analytical Chemistry, 2014, Volume 7, Pages 275-95, and "Single-cell technologies for monitoring immune systems," Nature Immunology, 2014, Volume 15, Number 2, Pages 128-135 secreted proteins may be measured on a per-cell basis. Additionally, exemplary apparatus and platforms for single cell and few cell analyses are disclosed in PCT Application Serial Number PCT/US2013/056454 (PCT Patent Publication WO2014031997), U.S. patent application Ser. No. 12/174,601 (US Patent Publication 2009/0036324), U.S. patent application Ser. No. 12/174,598 (US Patent Publication 2009/0053732), U.S. patent application Ser. No. 12/857,510 (U.S. Pat. No. 8,865,479), and U.S. patent application Ser. No. 13/132,858 (US Patent Publication 2012/0015824).

As will be described in greater detail hereinbelow, systems such as the aforementioned single cell analysis and few-cell analyses platforms and technologies may be adapted to benefit from the automated and semi-automated analysis methods of the present teachings to improve throughput, accuracy, inference discovery and results confidence. Furthermore, the apparatus, methods, and software of the present teachings may facilitate analysis of very large numbers of discrete samples when performing multiplexed chemical, biochemical, or cellular secretion analysis including those where multiple analytes are detected, identified, and quantified for each sample.

According to various embodiments, the disclosed detection methods may be used to analyze a wide variety of compounds including for example biochemicals, cellular secretions and/or expressed proteins associated with a biological system (for example, immunological cells) in a multiplexed manner. Additionally, a multiplicity of different proteins and/or compounds associated with a single or few cells (including cell-cell interactions) may be detected and analyzed to generate a cellular secretion or expression profile reflecting the response or status of a representative cellular population, cellular sub-population, or single cell for a subject or sample.

In the context of immunological analysis, due to the phenotypic and functional heterogeneity of immuno cells and the plasticity of immune cell differentiation, conventional methods that analyze cells in bulk create difficulties in defining or identifying correlates of immune protection against diseases such as cancers and infectious agents such as pathogens. Secretion and expression profiles associated with immune protection are potentially valuable and measurable predictors of an individual's immunity. Such profiles may be used to evaluate and quantitate response to a pathogen, disease, or treatment and are helpful tools in clinical analysis.

Correlates of protective immunity (for example associated with T cells) have been particularly challenging for immunologists to identify at least in part as the degree of protection may not clearly match or have similarities with known cellular phenotypes and/or surface markers for the cells. Further, functional profiles for TH1 cells (Type I helper T cells), one of the major functional subsets differentiated from naïve CD4 T cells, have demonstrated marked heterogeneity as reflected by their various cytokine profiles. Using conventional methods based on flow cytometry, functional analysis of effector T cells have attempted to delineate functional subsets of cells. It has been shown that each of these cellular groupings or classes can produce and release different combinations of cytokines within an immune response such as that elicited by bacterial infection.

In various embodiments, the system and methods of the present disclosure provide novel methods to measure cellular secretions and/or cell signals (such as those associated with immune cells or immune response). Analysis may be conducted at the single or few cell level (including cell-cell interactions) where the effector level for a plurality of cytokines may be evaluated per cell across a relatively large number of cells in parallel.

As will be described in greater detail hereinbelow, the disclosed methods enhance and improve the performance of analysis platforms addressing particular issues related to distinguishing cellular retention regions or areas, identifying and classifying cells/particulates, addressing systematic errors, and automating analysis workflows to enable high throughput sensitive and accurate assessments required to analyze many hundreds, thousands, millions, or more discrete cells or samples in parallel. Such methods may advantageously be used to improve existing analysis platforms and technologies to create valuable discovery and screening tools that may be used to understand and survey many different types of cellular poly-functionality, such as those implicated and correlated with immune response.

FIGS. 1A/1B depict an exemplary high-level workflow 100 for performing sample analysis. The analysis may include evaluation of one or more samples 102, 104 comprising a population or distribution of cells, beads, or other particles 106 harvested or collected from one or more selected sample sources (for example, cells obtained from an individual or culture representative of a selected biological state, chemically responding to a disease, pathogen, or therapeutic treatment). According to the present disclosure, where reference is made to one or more populations of cells, beads, or particles as comprising the selected or desired sample to be analyzed other types of particulates associated with analytes to be detected and evaluated may also comprise the sample(s). Furthermore, the sample(s) may comprise various distinct or different populations of cells, beads, or other particles forming one or more mixed populations of materials to be analyzed collectively. It will be appreciated that references to "cells" or "beads" are intended as exemplary of classes of particles that may be analyzed for associated analytes. Thus, the present teachings can be applied to a wide variety of different types and compositions of particulates 106 without departing from the scope of the present teachings.

As referred to above, the cells/particulates 106 of the sample(s) 102, 104 are evaluated for constituents associated with or comprising a plurality of analytes 108. Analytes 108 according to the present disclosure may take many forms. For example, analytes 108 may comprise chemicals, compounds or materials that are labile, dispersed, diffused or dissolved within an aqueous medium (for example a cell culture medium) or a fluidic/semi-fluidic carrier that are associated, secreted or released by the cells/particulates 106. Analytes 108 may further comprise biomolecules or organic molecules such as nucleic acids, peptides, peptide fragments, cells surface receptors, nucleic acids, hormones, antigens, growth factors, proteins, antibodies, cytokines, chemokines, or other molecules. Analytes 108 may further comprise other types of materials or compounds such as ions or inorganic chemicals associated, secreted or released by the cells/particulates 106.

According to various embodiments, the apparatus and methods of the present disclosure are particularly well suited for the analysis of small concentrations of analytes 108 associated with discrete single or few-cells contained within or comprising the samples 102, 104. Such analytes 108 may include for example cell-membrane associated proteins, cytokines, chemokines, or other biochemicals secreted or released by the cellular samples 102, 104 that are desirably analyzed in parallel in a highly-multiplexed manner. Sample populations or cellular constituents thereof may further be compared for similarities and/or differences in analyte presence, expression, or abundance such as may arise from a first control, normal, or untreated cellular population compared with a second test, abnormal/diseased, or treated cellular population.

According to FIGS. 1A/1B, one or more samples 102, 104 containing cells/particulates 106 to be analyzed are harvested or collected in Step 110. The cells/particulates 106 are then distributed and retained in discrete portions in Step 120. Sample distribution is accomplished using a substrate comprising a sample array 122 having a plurality of discrete chambers, wells, troughs, channels or other features/areas that comprise retention regions 124. The retention regions 124 are further suitably configured to contain, hold, or sequester at least a portion of the cells/particulates 106. In various embodiments, the array 122 used for distributing the cells/particulates 106 comprises a plurality of retention regions 124 such as wells, troughs, cavities, or depressions formed in the sample array 122 that are suitably sized based on the dimensionality of the cells/particulates 106. Distribution of the cells/particulates in Step 120 may involve dispersing the sample in a selected fluidic volume such that a desired number of cells/particulates are expected to be disposed in one or more of the retention regions based on the volume of the regions and the amount of fluid-containing sample to be located, disposed, or placed therein.

In various embodiments, the sample array 122 may comprise a plurality of discrete retention regions each configurable to hold or position a desired number of cells/particulates. The sample array 122 according to the present teachings may include a large number of retention regions 124. For example, many hundreds, thousands, or millions of discrete retention regions 124 may be formed in the sample array 122. In one exemplary embodiment, the sample array 122 may comprise a structure of between approximately 1-10 cm in length and/or width having between approximately 1,000-100,000 discrete retention regions formed therein.

In various embodiments, the sample retention regions 124 comprise microchambers/microwells having dimensions of approximately 0.01-5 millimeters in length and about 0.5-100 micrometers in depth. In other embodiments, the microchambers/microwells have a generally rectangular profile with a length of approximately 0.1-2000 micrometers, a width of about 0.1-100 micrometers and a depth of about 1-100 micrometers. The size and shape of the microchambers/microwells can be configured for a variety of applications and cell/particulate types. For example, to accommodate larger cell/particulates commensurately larger microwells may be desirably used. Additionally, for experiments involving more than a single cell/particulate to be evaluated in each microchamber/microwell the size and/or dimensionality of the microchamber/microwell can be configured accordingly. Additionally, the density of the sample array 122 can be flexibly configured, for example, with between approximately 100-50,000 microchambers/microwells per $cm^2$.

Using dilution methods such as those based on Poisson statistics, an expected distribution of cells/particulates 106 may be achieved resulting in at least a portion of the retention regions 124 receiving a small number of cells/particulates or in various embodiments a single cell/particulate 106. According to this approach for sample dilution/distribution some retention regions 124 may receive no cells/particulates 106 while others may receive more than the desired amount of cells/particulates 106 (e.g. more than one or a few cells). In various embodiments, analysis of analytes 108 associated with sample populations of a few cells/particulates 106 and more particularly single cells/particulates 106 includes identification of the presence and numerosity of cells/particulates 106 within respective retention regions 124. As will be described hereinbelow, the system and methods of the present disclosure are able to effectively image and distinguish desired cell/particulate distributions for the various retention regions to identify those which contain the desired amount or number of cells/particulates.

Following sample distribution, the cells/particulates 106 are incubated in respective retention regions for a selected period or duration in State 130. Incubating according to selected criteria or protocols, the retained cells/particulates 106 release analytes 108 into a surrounding volume 132 within the discrete retention regions 124 (e.g. the volume in which medium containing discrete single or few cells/particulates are retained). The configuration of the sample array 122 allows the cells/particulates 106 of the sample(s) 102, 104 to secrete/release analytes 108 into the volume 132. During the incubation period analyte concentrations may build up and/or diffuse within the volume 132 of the retention regions 124.

Analytes 108 released into the volume 132 of the retention regions 124, for example by dispersal or diffusion throughout at least a portion of the retention region, may further associate or react with one or more detection moieties 135 disposed or located about selected positions of an analyte detection substrate 134 in Step 140. The detection moieties 135 may comprise antibodies, nucleic acids, proteins or other chemical/biochemical constituents that selectively react, couple, recognize, or otherwise distinguish and/or detect the presence of one or more selected analytes 108. In general, the size and configuration of the retention regions 124 provides sufficient volume/area to allow analytes 108 to be dispersed in a manner so that they may be discretely detected by the detection moieties 135 through association with or positioning about selected portions or regions (e.g. analyte detection regions 136 where the detection moieties 135 are positioned or disposed) of the analyte detection substrate 134.

In various embodiments, secretions, biochemicals, cytokines, chemokines, proteins, peptides, peptide fragments, cells surface receptors, nucleic acids, hormones, antigens, growth factors or expressed proteins associated with the distributed cells/particulates 106 retained in discrete retention regions 124 diffuse and distribute in the volume 132 and become selectively associated with, captured, or retained by one or more detection moieties 135 disposed or positioned in analyte detection regions 136 associated with the analyte detection substrate 134 forming a detectible or discernable pattern, fingerprint, or barcode 142 which when detected in State 150 forms a representation of the presence and composition of analytes 108 associated with respective cells/particulates 106 contained within occupied retention regions 124.

In various embodiments, the analyte detection substrate 134 is configured with a plurality of analyte capture or detection moieties 135 capable of detecting and distinguishing numerous analytes 108 (for example between approximately 10-1000 different types of analytes). The positioning or association of the analyte detection moieties 135 in analyte detection regions 136 on the analyte detection substrate 134 is conducted in such a manner so that simultaneous determinations of analyte 108 presences and/or abundance may be determined in a highly multiplexed manner based on the pattern, fingerprint, or barcode 142. In various embodiments, the disposition or positioning of the analyte detection moieties 135 disposed or positioned in analyte detection regions 136 on the analyte detection substrate 134 permit secreted and/or released cytokines, chemokines, proteins, or other cellular constituents to be readily and individually classified based on the types and presence of the analytes 108.

The analyte detection substrate 134 may be comprised of a plurality of capture agents or detection moieties 135 each discretely or specifically recognizing a compound, chemical or biochemical of interest. The analyte detection moieties 135 may further be arranged in distinct or positionally discrete features (e.g. analyte detection regions 136) about the analyte detection substrate 134 providing spatial separation between the various analyte detection moieties 135. Such spatially separate arrangements of analyte detection moieties 135 provide for spatial encoding or patterning the detected analytes 108 in or about analyte detection regions 136 that may be resolved based on a known distribution of the analyte detection moieties 135 in or about analyte detection regions 136 associated with the analyte detection substrate 134. In various embodiments, the analyte detection substrate 134 may comprise analyte detection moieties 135 arranged in the analyte detection regions 136 as a plurality of lines, spots or other discrete shapes or combinations of shapes.

Each analyte detection region 136 may further be comprised of one or more types of analyte detection moieties 135 capable of being distinguished from one another through the use of different markers, labels, dyes, or other means generating distinct signals or other spectrally separable characteristics that may be discerned upon imaging, for example, using different optical characteristics or wavelengths during imaging. In various embodiments, the analyte detection substrate 134 comprises one or more duplicative, redundant, or repeating analyte detection moieties 135 or analyte detection regions 136 that may be used, for example, to provide multiple opportunities for analyte presence to be discerned and compared using signals, readouts, or patterns obtained for the corresponding analyte detection regions 136.

A plurality of analytes 108 are desirably identifiable and/or quantifiable for the cell(s)/particulate(s) 106 associated with respective sample retention regions 124. In various embodiments, the analyte detection substrate 134 provides the ability to detect and resolve approximately 5-1000 or more different analytes 108 using corresponding analyte detection moieties 135/analyte detection regions 136. The analyte detection moieties 135/analyte detection regions 136 disposed or located on the analyte detection substrate 134 are typically ordered or patterned in a manner that corresponds with or is complimentary to the sample retention regions 124 of the sample array 122. Thus the length and width of respective analyte detection regions 136 and the overall size and/or groupings of analyte detection regions 136 may be variably configured based on the corresponding or available area determined by the sample retention regions 124.

As will be described in greater detail hereinbelow, signals resulting from the coupling or association of analytes 108 with corresponding analyte detection moieties 135 associated with the analyte detection regions 136 may be imaged forming signal fingerprints, barcodes or other discernable patterns that may be analyzed and resolved to determine analytes 108 present in respective sample retention regions 124 of the sample array 122. These analytes 108 may further be correlated with cell(s)/particulate(s) determined to be present in respective sample retention region 124.

Detected analyte patterns may be resolved to the presence or quantity of discrete analytes based on the spatial separation, spectral separation, or a combination of both spatial and spectral separation for the analyte detection moieties 135/analyte detection regions 136. The present apparatus and methods may be used to resolve the presence of a plurality of analytes 108 by multiplexed detection of 2 or more, 3 or more, 4 or more, 5 or more, 10 or more, 20 or more, 40 or more, 50 or more, 100 or more, 1000 or more analytes of interest. The image analysis apparatus and methods of the present disclosure thus provide the ability to detect large numbers of different analytes for large numbers of discrete single cells/particulates or discrete few cells/particulates (co-located or co-positioned in corresponding sample retention regions 124) in parallel.

Analyte detection in Step 150 may comprise imaging the analyte detection substrate 134 (either directly or following separation from the sample array 122) to identify signals or markers (e.g. for example fluorescent and or radioactive) representative of the presence of analytes 108 that have coupled or associated with analyte detection moieties 135. In various embodiments, the analyte detection moieties 135 may comprise light-generating markers, energy-emitting markers, dyes, or other labels 136 and utilize techniques such as antibody capture and ELISA analysis for analyte detection.

Cells/particulates 106 and their corresponding analytes 108 are characterized in Step 160 by association of detected or discerned patterns, fingerprints, signal readouts or barcodes 142 with respective retention regions 124. This processing includes identifying and distinguishing discrete retention regions 124 associated with corresponding areas for the analyte detection substrate 134. As will be described in greater detail hereinbelow, this process may include a number of operations that determine the position and/or orientation of corresponding cells/particulates 106, retention regions 124, and detected or discerned patterns, fingerprints, or barcodes 142 in a highly multiplexed manner. This analysis further provides a basis to discern the secretions, biochemicals, and/or expressed proteins for individual or a few cells in a highly parallel manner allowing other analysis such as phenotypic characterization to be performed from the resulting patterns of detected analytes to characterize individual samples including quantitation of analytes, determination of expression patterns, categorization or grouping of samples into classes, and other analytical functions.

A particular challenge in high throughput single cell analysis results from the large number of very small features that must be rapidly and accurately assessed in a substantially parallel manner. Such apparatus and methods should be capable of not only separating and retaining single cells in discrete regions but also should accurately discern large numbers of discrete low abundance analytes with a high degree of confidence. Sample and substrate features are typically diminutive in size necessitating high-resolution and careful imaging (for example using high resolution instruments and/or microscopes). In various embodiments, potentially complex analyte detection patterns, fingerprints, signal readouts or barcodes must also be discerned or associated with individual wells or analytes 113 or analytes 115 to provide the ability to simultaneously detect and evaluate multiple analytes from each sample. Again the size of the analyte regions or areas and the closely spaced disposition of the analytes to be detected presents a particular challenge in terms of performing accurate analysis.

FIG. 1C depicts an image of a portion of an exemplary sample array 122 with magnified sub-portion 180 according to the present disclosure. The sample array 122 may comprise many hundreds, thousands or more of discrete sample retention areas 124 as shown in the magnified sub-portion 182. Each sample retention area 124 may further retain a single cell or few cells (or similarly particles) 106. Individual cells/particulates 106 should not only be confidently discernable and associated with a respective sample retention area 124 in which they reside but also must be distinguished from various potential artifacts, noise and other sources of error. Various factors that may directly influence imaging quality include for example, the size of the cells versus potential contaminants, distinguishing particular cell-types in mixed populations, low quality/contrast in the image acquisition, deformities in the sample array, bubbles and other artifacts. As will be appreciated by those of skill in the art, imaging and resolving cells/particulates in the presence of such confounding factors presents particular challenges.

FIG. 1C further depicts an image of a portion of an exemplary analyte detection substrate 134 with magnified sub-portions 280, 282 according to the present disclosure. The analyte detection substrate 134 may comprise many hundreds, thousands or more of discrete analyte detection regions 136 as shown in the magnified sub-portion 282. Each analyte detection region 136 may form an analyte pattern 142 corresponding to markers 135 detecting analytes 108 associated with cells/particulates 106. Various factors that may directly influence imaging quality include for example, the noise and background for regions where analyte markers 135/patterns 142 are detected. As will be appreciated by those of skill in the art, imaging and resolving markers 135/analyte patterns 142 in the presence of such confounding factors presents particular challenges.

FIG. 1C further depicts an exemplary overlay, merging, or association 291 of corresponding images of portions of the sample array 122 and the analyte detection substrate 134. Alignment and positioning of corresponding portions of the images of the sample array 122 and the analyte detection substrate 134 provides a means to associate the signals from various markers 135 detecting analytes 108 forming the analyte patterns 142 with the cell/particulate 106 for which the analytes 108 are further associated. Mechanisms for aligning and positioning the corresponding portions of the images and analyzing the associated data is described in greater detail hereinbelow.

As previously described and in various embodiments, features that are to be desirably detected and associated during analysis 100 include the various cells or particles 106, the retention regions or microchambers 124, and the patterns, fingerprints, signal readouts or barcodes. The small size (for example, typically on the order of 20 micrometers or less in at least one dimension) and distinctive properties associated with imaging and resolving the various features presents numerous challenges that are to be desirably overcome, especially when applying automated or semi-automated data acquisition and processing mechanisms required to achieve acceptable throughput and accuracy. The present methods and apparatus are capable of achieving requisite high-quality data for single- or two-cell/particulate chemical or biochemical profile readouts, in particular, per assay chamber or retention region 124 while imaging large numbers of these features including for example thousands of cells/particulates 106, thousands of microchambers or retention regions 124, and for hundreds of thousands if not millions of readouts for ease of detection and analysis.

For cellular analysis involving sample arrays with very small feature sizes imaging at very high resolutions may be impractical and/or infeasible necessitating alternative methods for data acquisition and analysis. One reason for this limitation is that imaging devices, such as scanning microscopes and fluorimeters have resolution limitations. Upgrades to such hardware components can be very costly and integration of newer components difficult to perform for standardized or calibrated workflows that may be necessary in clinical and research settings. Additionally, addressing limitations in the field of view of imaging devices such as scanning microscopes that may be used for feature resolution scans, by leveraging conventional capture and tiling approaches is impractical or infeasible due to time, cost, and computational constraints. For example, imaging and analyzing a full sample array 122 with the many thousands or more of retention regions 124, cells/particulates 106, and analyte signal readouts could easily involve capturing and tiling thousands of images which may be overly time consuming or computationally prohibitive. The size of such a tiled image may readily exceed hundreds of millions of pixels or more making it very difficult to process and analyze. Alternatively, imaging at lower resolutions may be performed, however, such an approach may contribute to diminished analysis quality and result in high quantization errors where each feature has a limited number of pixels that may prevent accurate assessments of cell type, noise correction, and/or signal resolution.

A further limitation of some workflows is that the optical/detection characteristics and requirements of the cell/particulate sample array may be distinct and different from those leveraged to resolve/image the secretion profiles or detected compounds. Simultaneous imaging on a single device may therefore be impossible/impractical to conduct. Thus it may be desirable if not a prerequisite to perform multiple imagings using different signal/data acquisition devices (e.g. multiple microscopes/signal capture devices). These devices may not output data in identical formats (for example, at the same resolution or orientation) and therefore additional challenges are present to align and associate detected secretion patterns with specific retention regions and cells/particulates.

At the resolutions used to image both the sample array and chemical signal fingerprints the minute measurements required are potentially confounded by many sources of imperfections. For example, even micron levels of warping or distortion in the substrate surfaces as well as very small contaminants should be accounted for to achieve sufficiently high quality and accurate results. Additionally, imaging biological data including cells often results in inconsistencies in cell morphology and observed structure as well as the intensity and quality of the signal (secretion) readouts. The system, methods, and software of the present disclosure effectively address potentially observable variations such as those exemplified above while distinguishing noise/background with a high degree of confidence.

According to various embodiments, desirable features of the present teachings include the ability to automate data acquisition/extraction processes avoiding time-consuming and error-prone manual methods for obtaining data. Acquisition of assay data, even when attempting to leverage existing off-the-shelf/conventional image processing software, is both time-consuming (on the order of days per assay) and inaccurate. A further benefit of the present methods is that development of the integrated and optimized imaging solution disclosed herein provides the ability to confidently detect large numbers of very small features with a high degree of accuracy remaining economical and efficient time-wise while accommodating inconsistency of features, presence of noise, distortions or deformities in the substrate materials among other challenges. In various embodiments, the methods may be applied to develop automated procedures that are simultaneously very accurate, but likewise sufficiently practical to analyze, both from a time standpoint (for example less than 30 minutes of hands-on time) and a hardware standpoint (can be performed on a conventional computer).

Figure 1D:
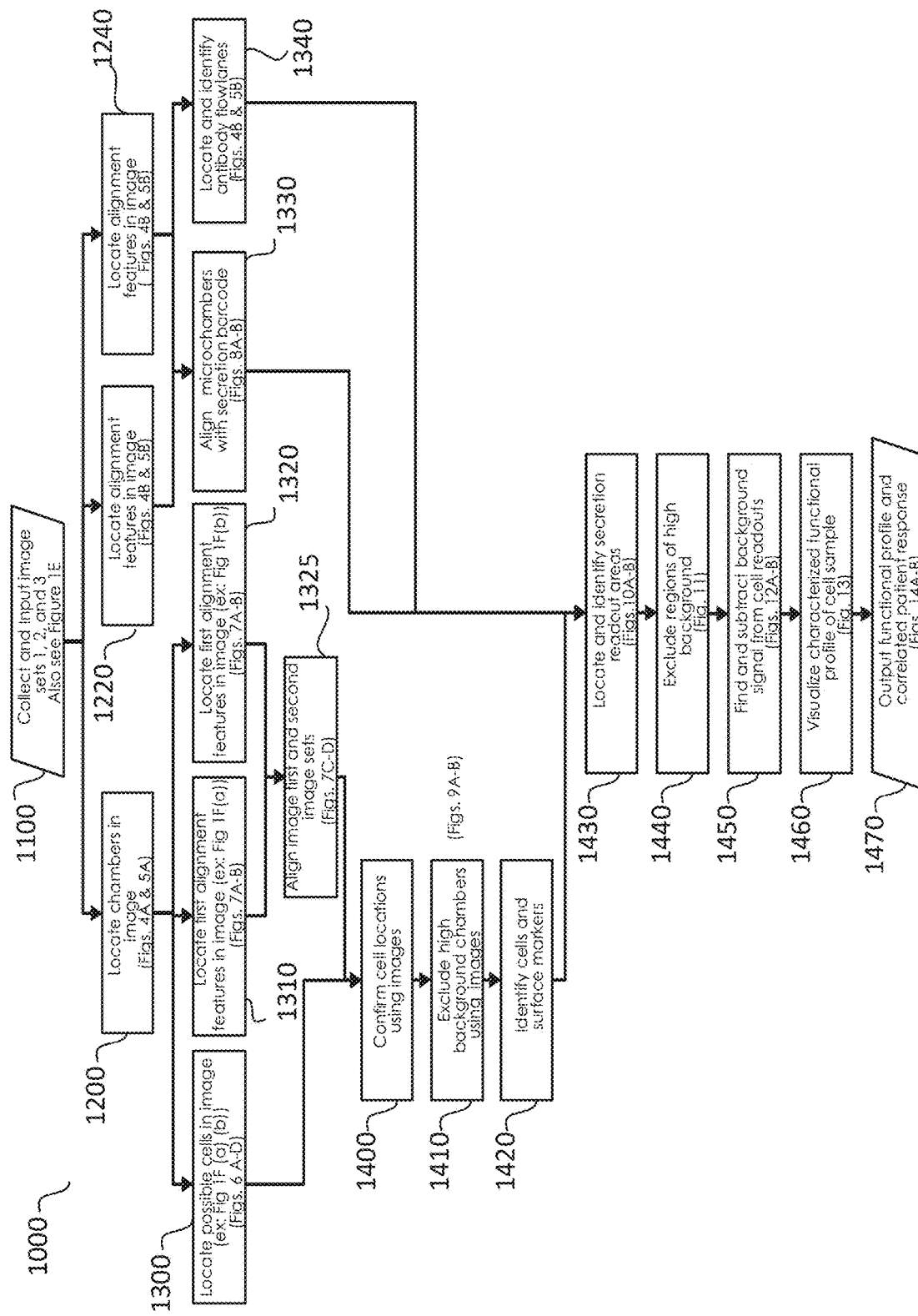
FIG. 1D depicts an exemplary detailed analysis workflow for imaging and resolution of sample array data according to the present disclosure.

As discussed above, the methods and apparatus for cellular analysis address many issues and shortcomings of conventional single cell image analysis solutions. FIG. 1D depicts a detailed analysis workflow 1000 that may be used for imaging and resolution of sample array data (for example single cell analysis arrays) according to the present disclosure. The workflow 1000 commences in state 1100 with collection of a plurality of images associated with sample retention regions 124 of the sample array 122 and associated patterns, fingerprints, signal readouts or barcodes 142 representing signal acquisitions from detected analytes 108 for various cells/particulates 106 disposed in the sample retention regions 124.

In various embodiments, sample imaging and analysis operates by evaluation of groupings or collections of associated images and signal acquisition information for selected regions of the sample array 122. A selected imaged region of the sample array 122 may represent a sub-region 180/182 (see FIG. 1C) where a portion of sample retention regions 124 from the sample array 122 are captured in an image. According to the present disclosure, rather than attempting to stitch a representation of the entire sample array together (a laborious, computationally expensive and error-prone process), each sub-region 180, 182 may be independently imaged and evaluated to achieve high quality data and results rapidly using inexpensive commodity computing systems. Fiducials, labels, identifiers or other positional features (collectively, alignment markers) may be included, etched, or printed on the sample array 122. The alignment markers may further be used to facilitate orienting or identifying sample retention regions 124 through or across multiple images and scans such that discrete sample retention regions 124 of the sample array 122 may be associated with cells/particulates 106 residing or disposed therein. The cells/particulates 106 may further be associated with the identified patterns, fingerprints, signal readouts or barcodes (collectively analyte patterns) for the cells/particulates 106 facilitating high accuracy profiling of the detected released secretions and analytes 108.

As will be described in greater detail hereinbelow, a first image or scan (for example, a high resolution light field image) is obtained for a selected sub-region 180, 182 of the sample array 122. The high resolution image (such as may be obtained using a light microscope with a 10×-50× objective) may be used for initial cell/particulate detection. Using this first image the location, number, and distribution of cells/particulates 106 in the various sample retention regions 124 of the sub-region 180, 182 of the sample array 122 may be discerned. Additionally, sample retention regions 122 containing a desired number of cells/particulates 106 (for example single cells or two or more interacting cells) may be identified and distinguished from sample retention regions 122 containing no cells/particulates 106 or more than a desired number of cells/particulates 106. The high resolution image is also helpful for identifying and discriminating between relatively small effector cells/particulates 106 (for example in immunological assays identifying and distinguishing T-cells and natural killer cells from other cells which may be present in the sample.)

To further aid in accurate alignment of images and/or alignment markers associated with sample retention regions 124 and associated analyte detection regions 136, a second image for substantially the same or similar sub-region 180, 182 may also be obtained. The second image may comprise a lower resolution image or other image type applying different optical parameters compared to the first image. Together, the first and second images for imaged sub-regions 180,182 may aid in the alignment of various images/scans and provide improved cell/particulate detection and identification accuracy compared to the use of single imagings. In various embodiments, the second image may be obtained in various manners including using different optical settings such as adjusting contrast or focal plane orientation, changing digital resolutions, applying a designated fraction or percentage reduction in magnification compared to the first image (for example, 1×-5× for a lower resolution image as compared to 10×-50× for the first image or scan), and may be taken with different illumination/microscopy methods, (e.g., darkfield, phase contrast, fluorescence). In various embodiments, the analysis system may be preconfigured with desired optical settings or may perform a determination on-the-fly based on the data quality and experimental design parameters as to what types of optical settings are applied to both first and second images at each resolution setting. It will be appreciated that higher and/or lower resolutions and magnifications can be readily adopted for use in the imaging processes. In various embodiments, the magnification and other optical parameters for imaging will be determined, at least in part, by the dimensions of the sample array 122/sample retention features 124 and analyte detection substrate 134/analyte detection regions 136 as well as the type of cell/particulates 106 and analyte detection moieties used.

In addition to the first and second cell/particulate images obtained for a selected sub-region 180, 182, an additional scan or signal acquisition is performed to obtain or identify the analyte pattern 142 representative of the detected, released, or secreted compounds or analytes 108 associated with the cells/particulates 106 present in the sample retention regions 122 of the sub-region 180, 182. In various embodiments, the scan or signal acquisition information obtained for each sub-region 180, 182 may be obtained on separate instruments and/or at different times providing for more flexible data acquisition. Additionally, first and second imagings may be based on different optical properties or characteristics from one another and as compared to the analyte pattern scan. For example, the first and second imagings may be visible light-based images while the analyte pattern scan acquired from fluorescent signals.

In various embodiments, the various first and second images for selected sub-regions 180, 182 are associated and accurately aligned using fiducials or alignment markers that are detected and resolved in selected corresponding image sets. Furthermore, a separate set of alignment markers (or additional imaging of the first set of alignment markers at a different wavelengths using different markers, dyes, or labels) may be imaged in both the sample array/particulate imaging and the analyte detection scans. Alignment between the sample array images and the analyte detection scans may thus be performed to match or associate the secretions or released analytes 108 detected from the analyte pattern 142 associated with a selected sample retention region 124 with the corresponding cell(s)/particulate(s) 106 located or disposed therein.

It will be appreciated that many factors contribute to the overall quality of each image and the visibility of features/details in the respective images. Factors such as differences in lighting conditions, brightness, contrast, and focus can significantly affect imaging. By obtaining multiple images in the manner described above, it will be appreciated that the combined results of the images may contribute to improved identification reliability of both sample retention areas 124 and cell(s)/particulate(s) 106 contained therein. Furthermore, due to the generally small size of features (such as sample retention area outlines/borders and cell/particulate profiles in the images) having more than a single image and at different resolutions can prove to be very helpful in resolving/imaging the sample array 122 and constituents therein. As will be described in greater detail hereinbelow, various potential sources of noise and error that can otherwise act to obscure portions or entire features within a sub-region 180, 182 or result in misregistration of cell(s)/particulate(s) 106 and/or analyte patterns 142 can be reduced or eliminated using the multiple imaging methods of the present disclosure. These methods can be helpful in resolving or distinguishing useable data with increased accuracy and improved quantification capabilities from the sample array 122.

Figure 1E:
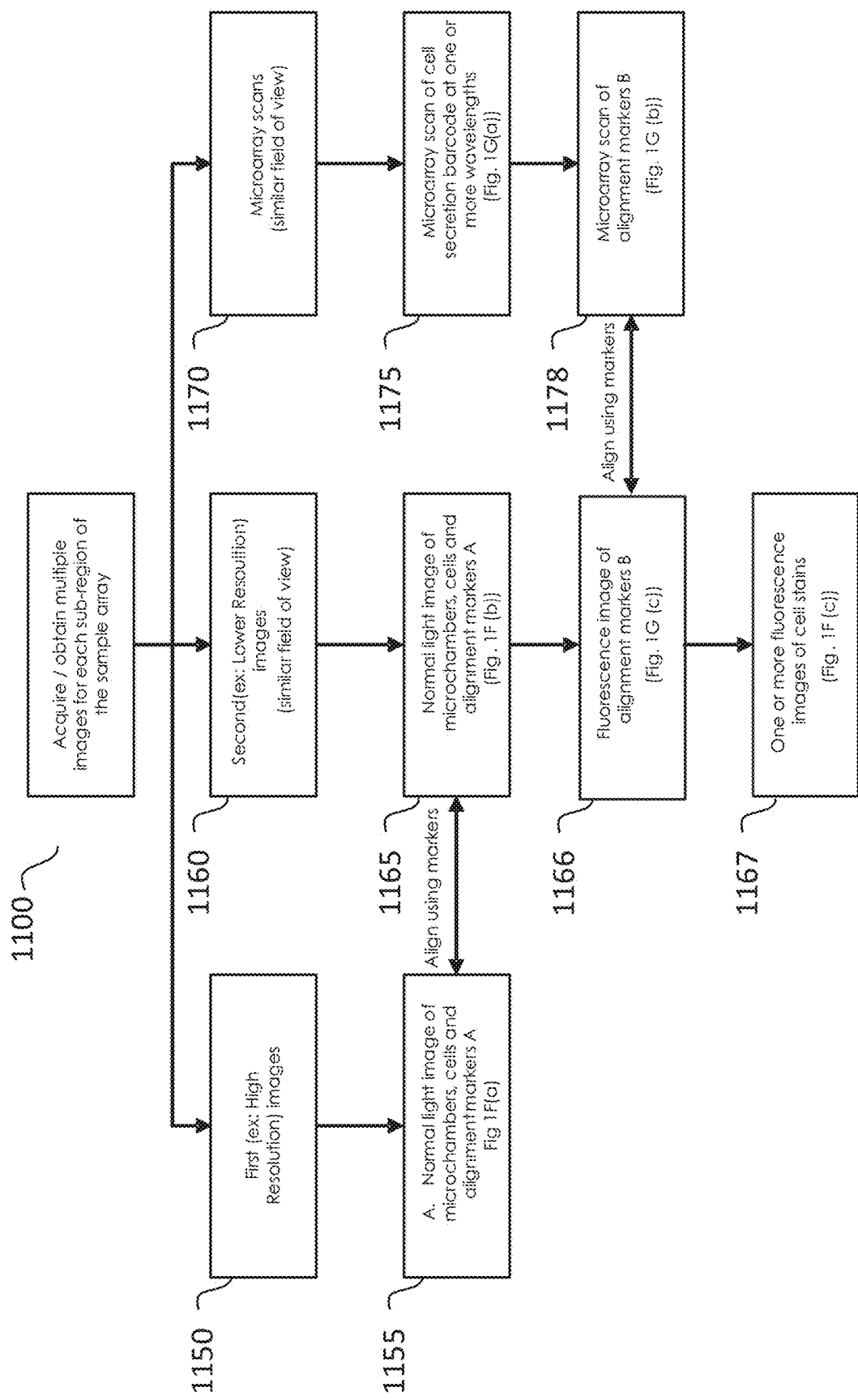
FIG. 1E depicts an exemplary outline of processes associated with multiple imaging of sub-regions of a sample array according to the present disclosure.

FIG. 1E depicts an outline of the processes associated with the multiple imaging of sub-regions 180, 182 of the sample array 122 described in Step 1100 in FIG. 1D. High resolution images 1150 may comprise one or more light field/bright field images 1155 of the microchambers/sample retention regions 124 and associated or nearby first alignment markers (designated in the diagram by an exemplary "A"). Second images 1160 may likewise comprise one or more light field images 1165 having a similar field of view for the sample retention areas 124 and associated cell(s)/particulate(s) 106 as the high resolution images 1155. First and second images may be aligned using alignment markers present on the sample array 122 and identified within the corresponding images to provide the ability to orient first and second images 1155/1165 with respect to one another.

Corresponding analyte pattern(s) 142 obtained, for example, through a fluorescent imaging or scan 1170 comprise one or more scans 1175 of analyte patterns 142. The analyte patterns may be further resolved to individual detected analytes 108 released or secreted by cell(s)/particulate(s) 106 present in the sample retention regions 124. The scans 1175 may further comprise discrete discernable patterns, fingerprints, detection patterns or barcodes 142 obtained by imaging at various selected wavelengths or using two or more modes of detection to form a collection of analyte patterns that are combined and evaluated to identify detected analytes 108 associated with, released, or secreted by the cell(s)/particulate(s) 108.

In various embodiments, a second imaging 1166 of the areas corresponding to the first and/or second images is obtained to identify one or more second alignment markers. In various embodiments, the second imaging is acquired at a different wavelength or emission spectrum for the second alignment markers such that they may be readily distinguished from the one or more first alignment markers. For example, a fluorescent imaging or scan of the corresponding regions of the first and/or second images may be obtained to distinguish a discrete marker set designated "B" in the Figure. Using the image and associated alignment marker sets, the microarray scan/analyte pattern (corresponding to the discernable pattern, fingerprint, or barcode 142 of analytes 108) including corresponding alignment markers "B" may be used to align or orient the first and/or second images with the corresponding microarray scan/analyte pattern. Taken together using the processes described above, the various images and scans for respective portions on the sample array 122 may be desirably oriented and aligned to associate cell(s)/particulate(s) 106 with corresponding analytes 108 to enable high quality profiling and compound analysis.

In certain embodiments, one or more additional imagings 1167 of the cell(s)/particulate(s) 106 associated with the selected sub-region 180, 182 imaged in the corresponding first and second images may be obtained. The cell imaging process 1167 may utilize similar or different wavelengths or scanning configurations as the alignment marker imagings or analyte detection scans. In various embodiments, the various cells or particulates 106 may be labelled with fluorescent or light-emitting dyes, stains, or other identification means to resolve the location or disposition of the cell(s)/particulate(s) 106 in various sample retention regions 109 of the sample array 122. This information may further be used to definitively identify the presence and/or number of cell(s)/particulate(s) 106 in a selected sample retention region 108 and may further be used to aid in associating the identified cell(s)/particulate(s) 106 with their corresponding discernable analyte pattern 142 and corresponding released or secreted analytes 108.

In various embodiments, the dimensionality and other characteristics of the cell/particulate 106 being analyzed may determine the number and or type of images to be acquired for subsequent detection and analysis. For example, relatively large cells (for example THP-1 cells) may be imaged without staining and subsequent fluorescent imaging. For relatively small cells (for example CD4 cells) fluorescent stains may not be required with multiple light field images acquired at various magnifications. For other small cell types, staining and fluorescent imaging as well as one or more light field images may be used. For mixed populations of cells and very small cells, surface markers may be used and detected with appropriate imaging parameters to distinguish cell types and/or to verify the presence of cells.

Figure 1F:
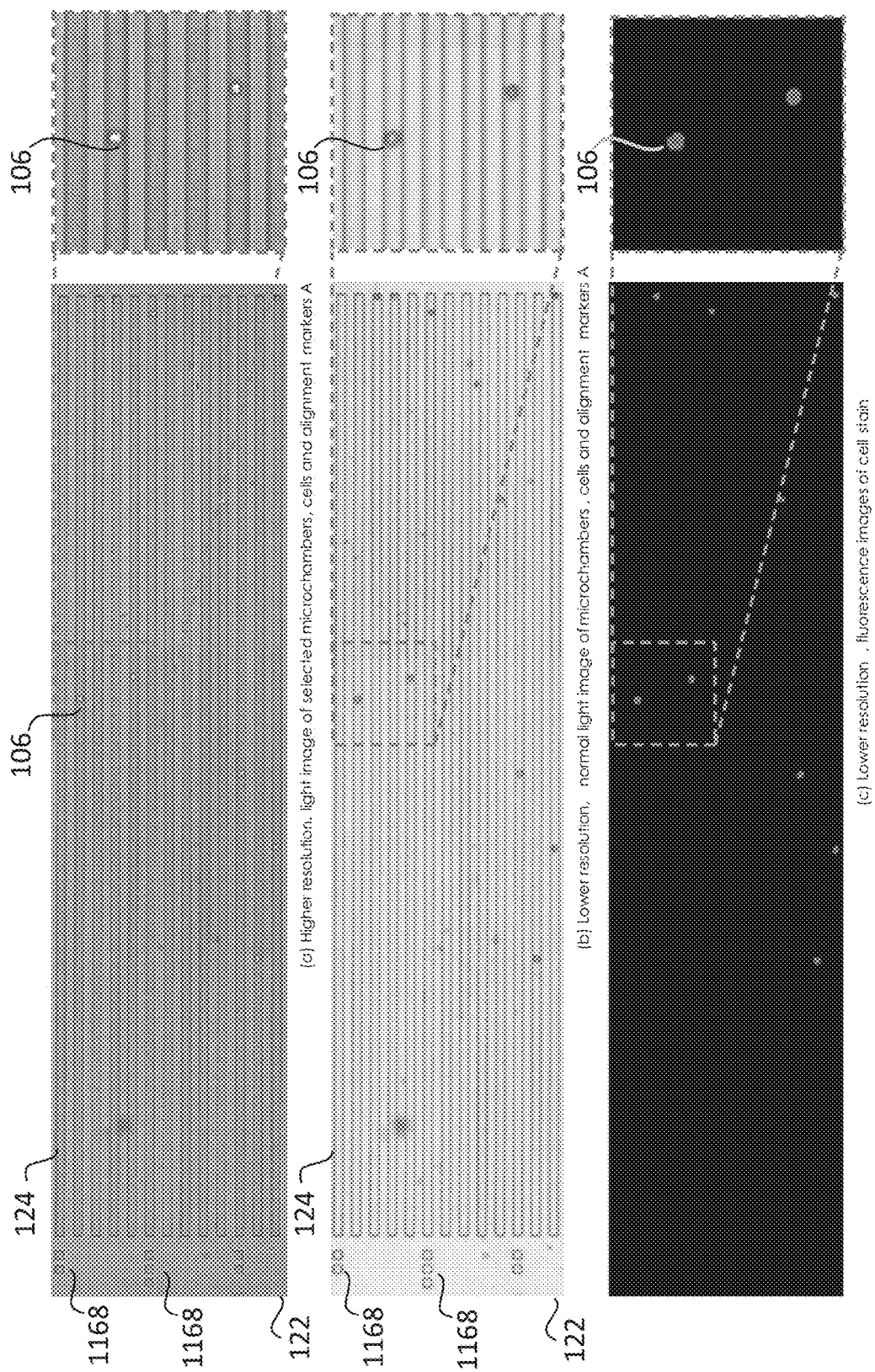
FIG. 1F depicts exemplary imaging of a selected sub-regions of sample array and cells/particulates according to the present disclosure.

FIG. 1F panel (a) depicts an exemplary high resolution imaging of a selected sub-region 180 of the sample array 122 comprising a plurality of sample retention regions 124. Cell(s)/particulate(s) 106 are further positioned in various sample retention regions 124 (further shown in expanded view). First and second positional/alignment markers 1168, 1171 (e.g. markers sets comprising "A" and "B") are further located about the sample retention regions 122 for alignment of images as discussed above. FIG. 1F panel (b) depicts an exemplary corresponding second image of a selected sub-region 180 of the sample array 122 comprising the same plurality of sample retention region 124. Cell(s)/particulate(s) 106 are positioned in the sample retention regions 124 at similar or identical locations as visualized in the first image. Positional alignment markers 1168 are visible about the sample retention regions 122 for alignment as discussed above. FIG. 1F panel (c) depicts the additional imaging of cells/particulates 106 resultant from fluorescent labeling and imaging (step 1166 in FIG. 1E). Cell/particulate positioning and orientation with respect to other cells/particulates may be preserved and comparable to that obtained for the light field images in panels (a) and (b) above. Cell/particulate positions are not necessarily required to be fixed or maintained in a single position however as the sample retention region 122 in which it resides may limit overall movement of the cell/particulate 106.

Figure 1G:
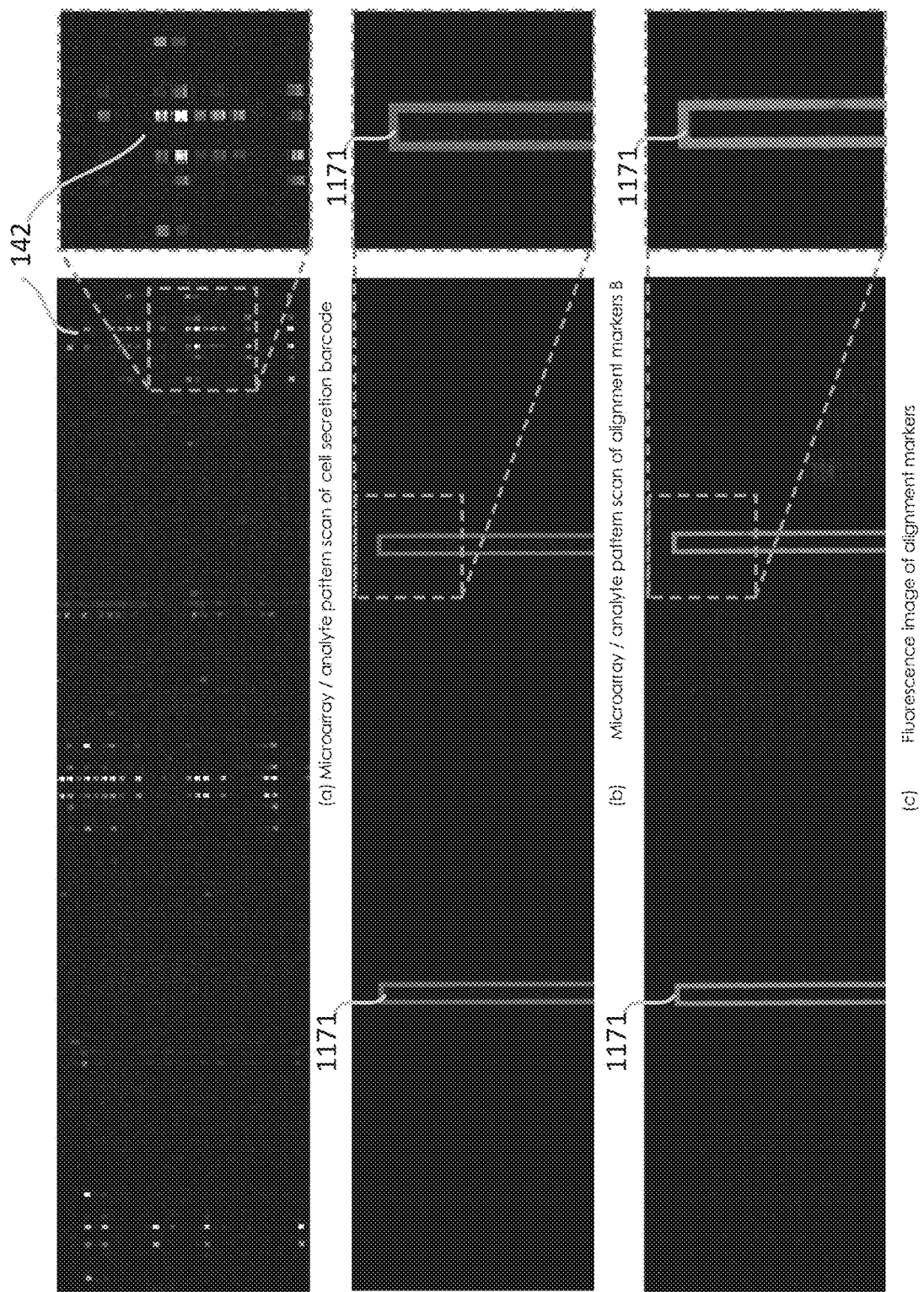
FIG. 1G depicts exemplary signal scans for analyte patterns and alignment markers according to the present disclosure.

FIG. 1G panel (a) depicts exemplary signal and alignment scans showing microarray/analyte patterns associated with detected analytes 108 released or secreted by cells/particulates 106. As described above the analyte pattern 142 may be resolved to individual or discretely detected analytes 108 associated with cells/particulates 106 disposed or retained in various retention regions 122. By correlating the analyte scans and underlying detected analyte patterns 142 with the first and/or second images for the sample retention regions 122 with cells/particulates 106, individual cells/particulates or collections of cells/particulates can be attributed to releasing or secreting multiple analytes 108 in a parallel and multiplexed manner.

According to the device imaging process (FIG. 1E, state 1175) analyte patterns 142 may be detected using multiple wavelengths or imaging/scan modes. For example, multiple discretely and differentially tagged or labelled analyte detection moieties 135 may be disposed in or co-occupy generally the same analyte detection region(s) or area(s) 136 of the analyte detection substrate 134. Different analytes 108 may selectively bind or associate with the differentially labelled analyte detection moieties 135 and be separately resolved or detected on the basis of the tags or labels 135 associated with the analyte detection moieties 135. Discrete resolution of co-located analytes 108 in the same analyte detection region 136 may be determined on the basis of different emitted signal/wavelengths associated with the tags or labels. Additionally, multiple images may be obtained at different wavelengths or use different filters or optical settings to separately resolve the analytes 108 in these regions. In certain embodiments, separate imagings may be acquired for the same analyte detection regions 136 to generate different analyte patterns 142 based on the analytes 108 present and the tag, marker, dye or label associated with the analyte detection moiety 135.

FIG. 1G panel (b) depicts detected second alignment markers 1171 associated with the analyte detection substrate 134. The second alignment markers 1171 may be resolvable in the device imaging process as previously described (FIG. 1E, state 1166). FIG. 1G panel (c) depicts detected second alignment markers 1171 associated with the sample array 122. The second alignment markers 1171 may be resolvable in the device imaging process as previously described (FIG. 1E, state 1166). According to various embodiments, the detected alignment markers for the analyte detection substrate 134 and the sample array 122 may be used to associate and orient the first and/or second images of the sample array 122 (FIG. 1E, state 1168). Alignment between these imagings and scans thus provides the ability to associate respective analyte patterns 142 with specific cell/particulates 106 releasing or secreting analytes 106 within analyte detection regions 136 as will be described in greater detail hereinbelow.

Figure 1H:
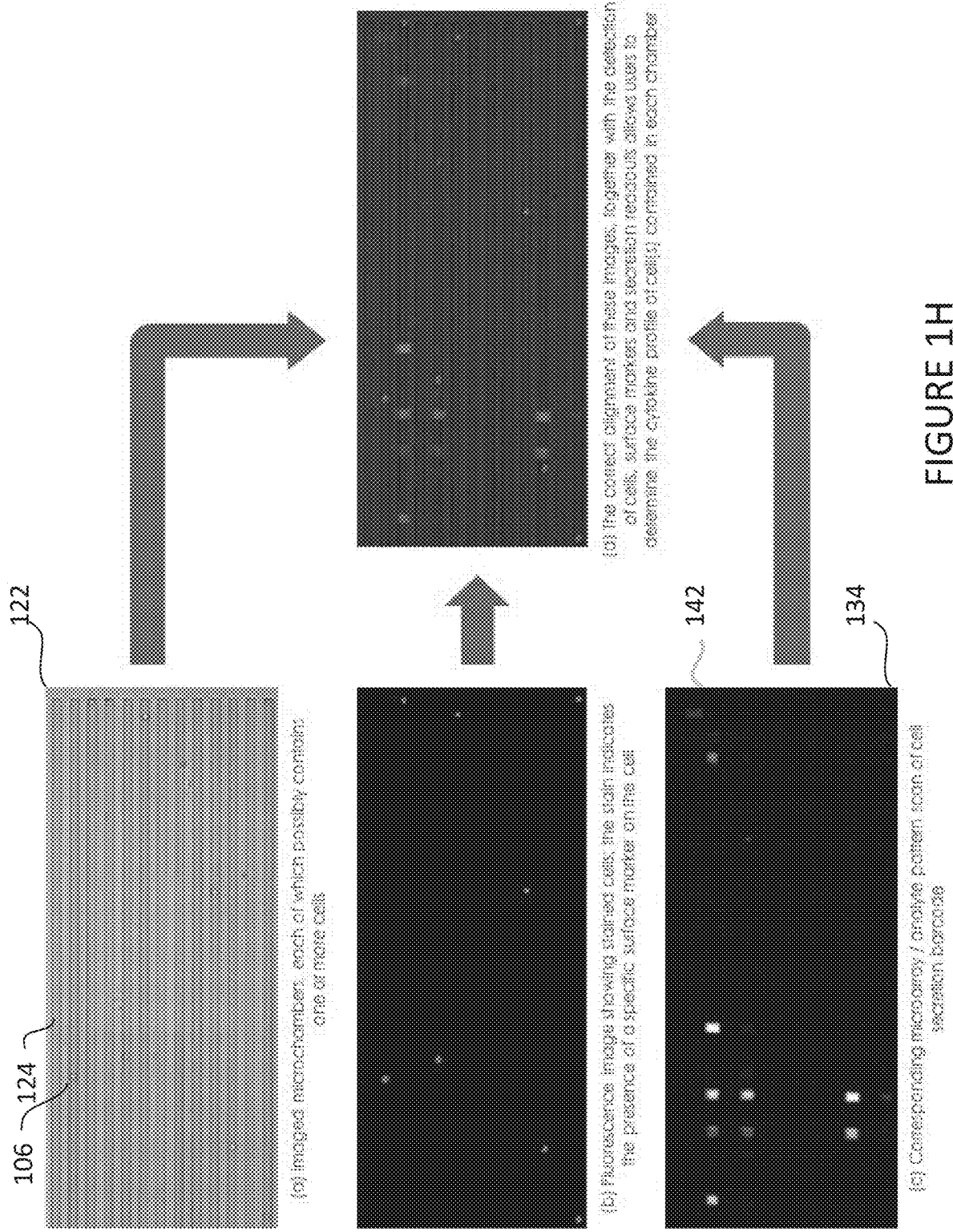
FIG. 1H depicts exemplary light field and fluorescent image panels for a sample array with associated image panel for a corresponding analyte detection substrate and the merging of the images panels according to the present disclosure.

FIG. 1H depicts a light field image (panel a) for a portion of an exemplary sample array 122 with sample retention regions 124 retaining single cells/particulates 106. FIG. 1H further depicts a corresponding fluorescent image (panel b) showing the cells 106 visualized by for example by a stain indicating the presence of a selected surface marker on the cells/particulates 106. FIG. 1H further depicts a corresponding image (panel c) for a portion of an exemplary analyte detection substrate 134 with analyte patterns 142 corresponding to markers 135 detecting analytes 108 associated with the cells/particulates 106. FIG. 1H further depicts the merging of the various images (panel d) to provide a mechanism to associate respective analyte patterns 142 with the associated cells/particulates 106 whose analytes 108 were detected.

Referring again to FIG. 1D, collected images of the various sub-regions 180, 182 of the sample array 122 and analyte detection substrate 134 are used in further processing steps according to the detailed analysis workflow 1000.

Initially, in state 1200 microchambers/sample retention regions 124 of the sample array 124 are located and resolved for respective images. Due, in part, to small feature size of the sample retention regions 124 as well as potential artifacts and distortions associated with the structures themselves and resulting images, it is desirable to conduct detailed evaluation of the various images and scans. These processes contribute to high quality analysis and aid in accurate determination of the various analytes associated with respective cells/particulates 106.

According to various embodiments, the sample array 122 may be configured with an ordered pattern or positioning of sample retention regions 124. An exemplary pattern may take the form of a two dimensional grid having rows and columns as depicted in FIG. 1C. To aid in orientation and determination of sample retention regions 124 and cell/particulates 106 residing therein, a regular patterning may be used where the dimensions of the sample retention regions 124 are generally similar and typically approximately equal to one another across various portions or sections of the sample array 122. Offsets between sample retention regions 124 may likewise be configured as generally similar and typically approximately equivalent to one another across various portions or sections of the sample array 122.

A principal operation during sample retention region identification processes is to determine the relative position or location of the imaged sample retention regions. The graphical or pixel area of selected sample retention regions 124 may then be used for determining respective positioning of cells/particulates 106 localized therein and alignment with analyte patterns 142. Improving the automated analysis capabilities of the imaging system is an important consideration to increasing overall analysis throughput. Thus, it is desirable to increase or maximize the number or proportion of sample retention regions 122 that may be detected.

In various embodiments, the regular ordering or patterning of the sample retention regions 122 provide generally consistent or expected dimensions and spacing that is helpful to leverage in automated analysis. Further, the associated detection procedures may be extendable or configurable to a number of different orientations, dimensions, spacings, and quantities of sample retention regions 124 on the sample array 122. The system may also be configured for analysis of different array configurations depending on the particular assay or preference of the user.

The imaging and identification processes may further accommodate various imperfections and deformities in the sample array 122 and associated sample retention regions 124. In certain embodiments, the sample array 122 is fabricated in such a manner that various deformities and/or imperfections may be present as a result of manufacture and/or processing. In some instances, the sample retention regions 124 may be slightly out of alignment or off-axis with respect to each other or have variations from lot-to-lot or array-to-array. There may also exist minor variations in sample retention region dimensions and spacing across the sample array 122. Further, various artifacts and debris may be present on the sample array or associated with various sample retention regions 124 that obscure sample retention region outlines or profiles. Additionally, the resultant images of the sample array and sample retention regions may include imperfections such as blurry areas or broken/distorted sample retention region outlines.

Figure 2:
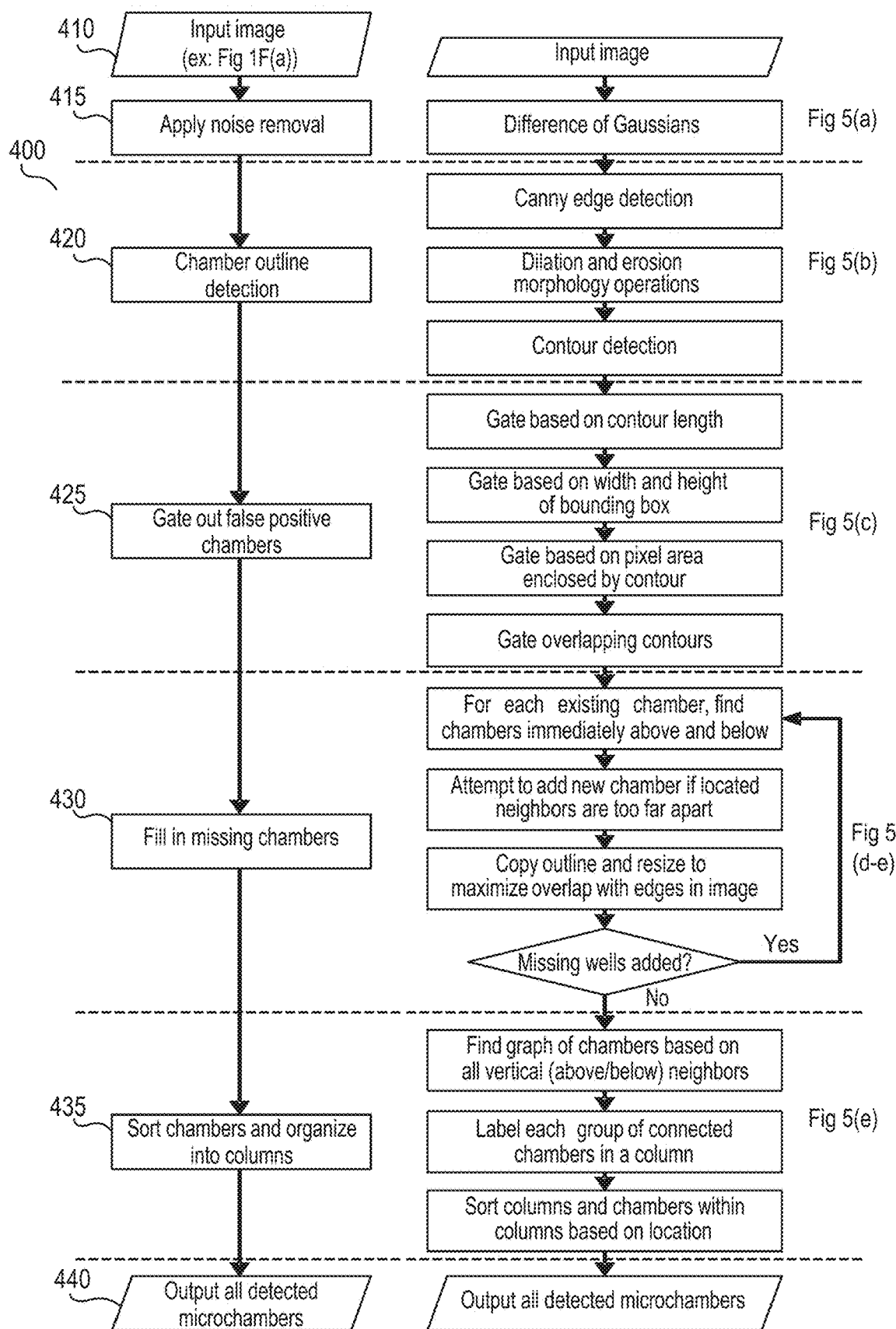
FIG. 2 depicts an exemplary process for sample retention region location determination and resolution according to the present disclosure.
Figure 4:
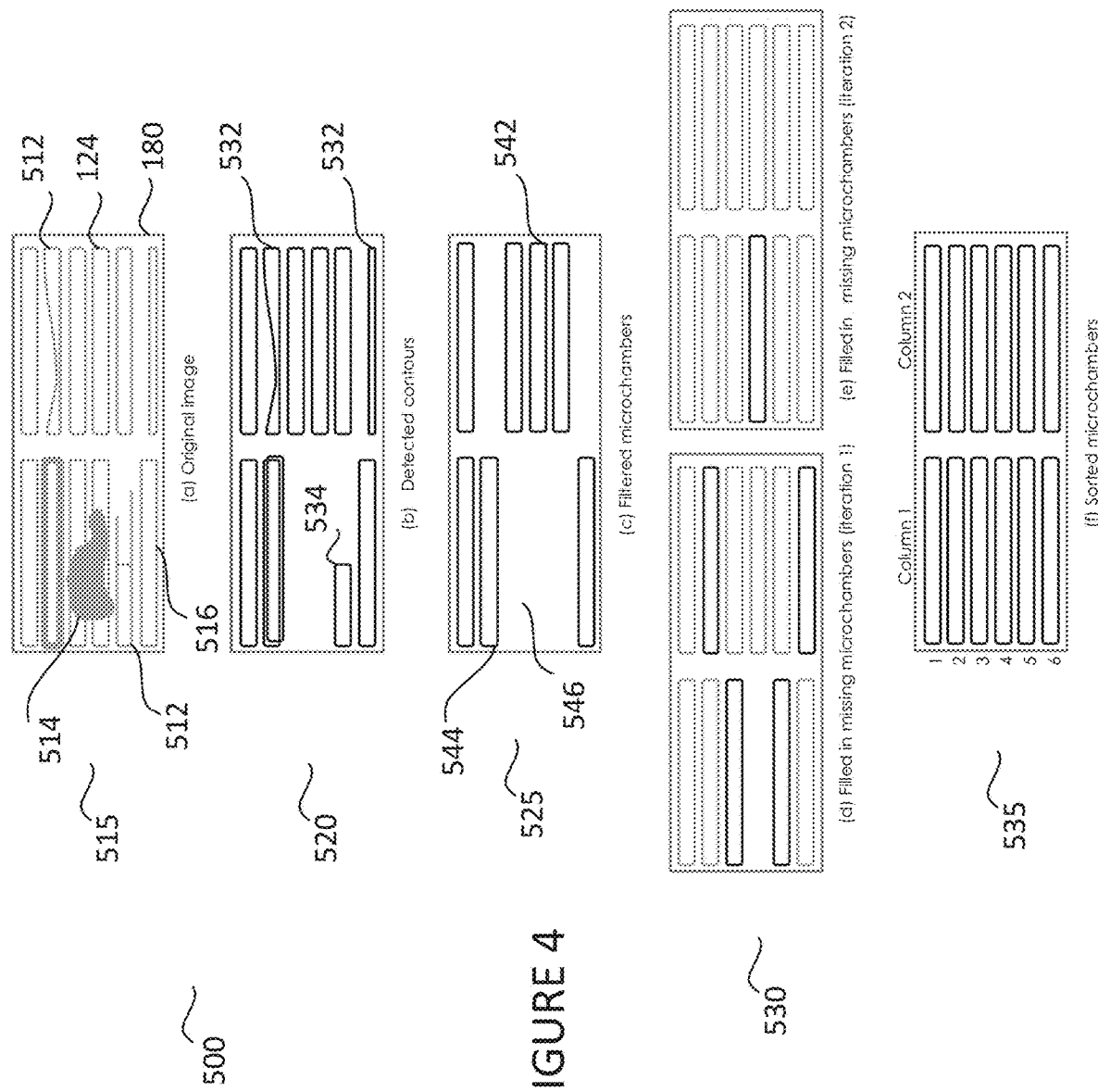
FIG. 4 illustrates exemplary operation of a sample retention region identification process according to the present disclosure.

A more detailed process 400 for microchamber/sample retention region 124 location and resolution associated with step 1200 is shown in FIG. 2. Additionally, FIG. 4 illustrates the principal operations 500 of sample retention region identification in a pictorial manner. As shown in FIG. 4, exemplary sample retention regions 124 may be subject to various imperfections 512 and artifacts 514 that obscure or confound analysis and are desirably addressed during automated image analysis.

The process 400 may be performed for selected, desired, or substantially all imagings of the sample array 122, for example using the high resolution light field images represented in FIG. 1F(a) and/or the second light field images represented in FIG. 1F(b). For each input image (410), representative of a selected sub-region 180, 182 of the sample array 122, a noise removal process (415/515) may be applied. The noise removal process may use various methods to identify noise and artifacts in the images including applying Gaussian difference methods. The results of the noise removal processing may exclude portions of sample retention regions of low quality or that cannot be confidently resolved or distinguished from surrounding background, noise or artifacts and may also be used to counteract or address small imperfections and image blurriness. Additionally, artifacts including imaged dust and debris may be removed from the image and/or excluded from further processing and image analysis. Artifact removal may be conducted in such a manner so as to avoid high likelihoods of excluding cells/particulates from the image.

Following noise removal (415/515), an outline detection routine (420/520) may be performed to detect the peripheries, boundaries, or edges of the various sample retention regions 124 in the image 410. Edges, contours, and other shape-based characteristics for the sample retention regions 124 may be determined by a number of methods including application of Canny edge detection methods. The morphology or profile of the sample retention regions 124 may be evaluated as part of this process to identify various distortions affecting selected sample retention regions 124 such as dilations 532 and/or erosions 534. Left unaddressed, these distortions may create difficulties in subsequent operations and potentially result in inaccurate or erroneous analyte analysis.

Application of the above-described processes helps identify and remove potentially problematic features and components of the image and may be used in connection with a filtering process (425/525). Excluding sample retention regions that are affected by artifacts and noise as well as those subject to significant deformities or other problems leaves a subset of filtered sample retention regions 542 having generally desirable and/or tolerable characteristics that may be readily analyzed in downstream operations. Certain filtering process may include gating out or excluding chambers by applying various criteria. For example, selected sample retention regions may be gated on the basis of discrepancies or deviations in contour length, width, height, or as a result of observed overlaps in the retention chambers.

It will be appreciated that exclusion of sample retention regions affected by noise, artifacts, and other issues results in a potential loss of data and information associated with cell(s)/particulate(s) 106 and detected analytes 108. In certain instances, a sample used in the analysis may be particularly rare or valuable, the analytes 108 or the detection moieties 135 used may be expensive or timely results are required which makes it important to capture as much information as practical from a given analysis or run.

A notable enhancement to the image analysis routines of the present disclosure is the application of a recapture or fill-in procedure (430/530). According to this approach, the expected or predicted location of a sample retention region 124 may be determined using the pattern of regular orderings among sample retention regions 124. For example, for a sample retention region 124 that has not been located or which may have been excluded in previous operations the relative location of neighboring sample retention regions 124 may be determined. Using an iterative process, existing/identified sample retention regions 544 immediately above and/or below a missing region 546 may be used to help identify the expected location of a sample retention region in the missing region 546. Attempts may further be made to recreate or add a missing sample retention region 546 on the basis of distance or space separating adjacent identified sample retention regions 124. Outlining and resizing operations may also be used to determine the approximate or expected position of sample retention regions 124. Taken together, where these operations are successfully applied, missing sample retention regions may be added back or constructed into the image. Application of these processes therefore provides the ability to rehabilitate or recover data from the image that might otherwise be lost or discarded.

Following the above-described operations, identified/remaining sample retention regions in the various images may be sorted and organized (435/535). In various embodiments, the sample retention regions 124 in a selected image may be oriented and/or grouped with respect to neighboring sample retention regions. For example, vertically aligned sample retention regions may be labelled in a columnar manner and sorted/cataloged for ease of further analysis. Detected, located, and/or identified sample retention regions 124 within the image may then be outputted (440) completing the process (1200/400/500).

In addition to the microchamber/sample retention region identification process 1200 described above, additional operations 1220, 1240 may be performed to identify and locate associated alignment features or markers associated with analyte scans and corresponding cell/particulate imagings. Such processes may be performed for selected, desired, or substantially all imagings/scans of the sample array 122 and analyte detection substrate 136. For example, a first alignment feature identification process 1220 may be performed using scans for the detected second alignment markers 1171 associated with the sample array 122 represented in FIG. 1G(c). A corresponding second alignment feature identification process 1240 may be performed using scans for detected second alignment markers 1171 associated with the analyte detection substrate 134 represented in FIG. 1G(b). Location of the alignment features for scans representing portions of the sample array 122 and the corresponding portions of the analyte detection substrate 134 may be performed according to the steps 450 outlined in FIG. 3 and illustrated renditions 550 in FIG. 5.

Using selected input images/scans (455, 555), alignment feature outlines, edges, or peripheries may first be detected (460, 560) using Canny edge detection methods and/or applying line detection approaches such as Hough transforms. In various embodiments, the alignment features comprise fine details, dimensions, and/or geometries 558 including for example angles, turns, and profiles that may aid in confident determination and resolution of the position of the alignment features. The alignment features, may further be resolved as a grouping of one or more segments to aid in determination of portions of the alignment features that are clearly identifiable and portions which may be less-clearly resolved.

Figure 5:
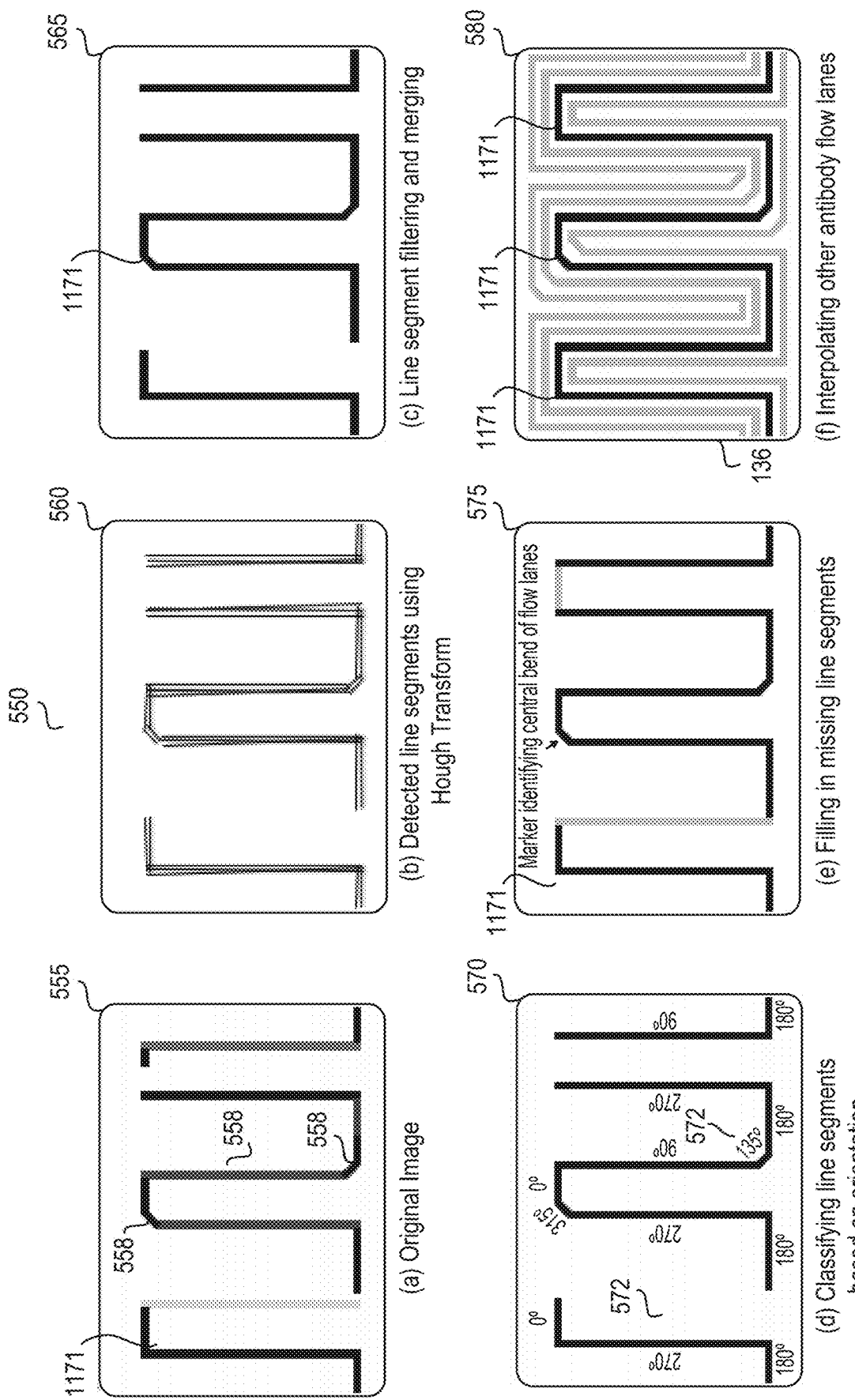
FIG. 5 depicts exemplary processes for alignment feature location and resolution according to the present disclosure.

In various embodiments, alignment portions or segments that are clearly resolved are filtered and grouped (465, 565). Filtering operations may include identifying selected expected or imaged angles, determined orientation and/or locations for portions of the segments and merging similar or expected portions/segments while removing or excluding less-confidently evaluated alignment portions. The remaining segments/alignment portions may be further identified, labelled, and/or ordered (470/570) for example according to angle and positioning. A portion of the operations may classify and/or label segment portions based on orientation or angle 572 as shown in FIG. 5. Using known or expected orientations for the alignment markers, portions that may be missing or poorly resolved from the images/scans may be filled in or reconstructed (475/575). Comparisons between expected and actual intervals between alignment markers may be used to reconstruct missing regions or segments.

Using the actual and reconstructed alignment markers, additional interpolation operations (480/580) may then be performed, for example, between adjacent segments to obtain expected orientations and positioning of analyte detection regions, flow lanes, and cell/particulate retention regions. Applying these operations to respective images for analyte detection regions and analyte patterns thus facilitate determination of expected and actual regions where cell/particulates 106 and analyte detection moieties 134 reside.

Referring again to FIG. 1D, using located sample retention regions 122 determined in step 1200, a subsequent stage 1300 of the analysis 1000 determines potential cells/particulates 106 that may reside in the sample retention regions 122. The operations of cell/particulate localization 1300 address issues associated with variances that may occur between cells/particulates and facilitate identifying/distinguishing desired cells/particulates 106 from both other cells/particulates 106 that may reside in the same sample retention region 122 as well as discriminating cells/particulates from other materials such as dust or particles that may not be associated with analyte release or secretions.

In various embodiments, a cell may have an expected morphology, shape, or size when analyzed. For example, cells may be expected to be approximately round and convex. Similarly, particulates may have known dimensions and uniformity. During imaging, the image of a cell may have an expected profile, for example, with a generally darker outline or peripheral portion as compared to a generally lighter interior portion. Similarly, particulates may have other expected characteristics such as being uniformly illuminated or displaying various other optical properties. Cells in particular can be challenging to identify with a high degree of confidence due to variance between the physical characteristics of individual cells. For example, cell size can vary, but may be assumed to reside within a selected range (for example approximately in the range of 5-20 microns) where cell morphology remains fairly consistent and independent of size. Further, in assays involving few or single cell(s)/particulate(s), a majority of the space within the sample retention regions 124 may remain open and cells/particulates 106 may be located in a variety of different positions within the sample retention regions 124.

According to the location identification step 1300, the occupancy and location (e.g. pixel area in a corresponding image) of one or more cells/particulates 106 within selected previously identified microchamber/sample retention regions 124 may be determined. These processes desirably accommodate cell-cell variances and deformities, variations in image quality, and help provide precise and accurate detection. The detection processes 1300 are also desirably configured as extendable to different cell/particulate types having different physical properties and dimensions while able to handle large numbers of discrete identifications associated with the large number of sample retention regions 124 to be analyzed.

Figures 1, 6A:
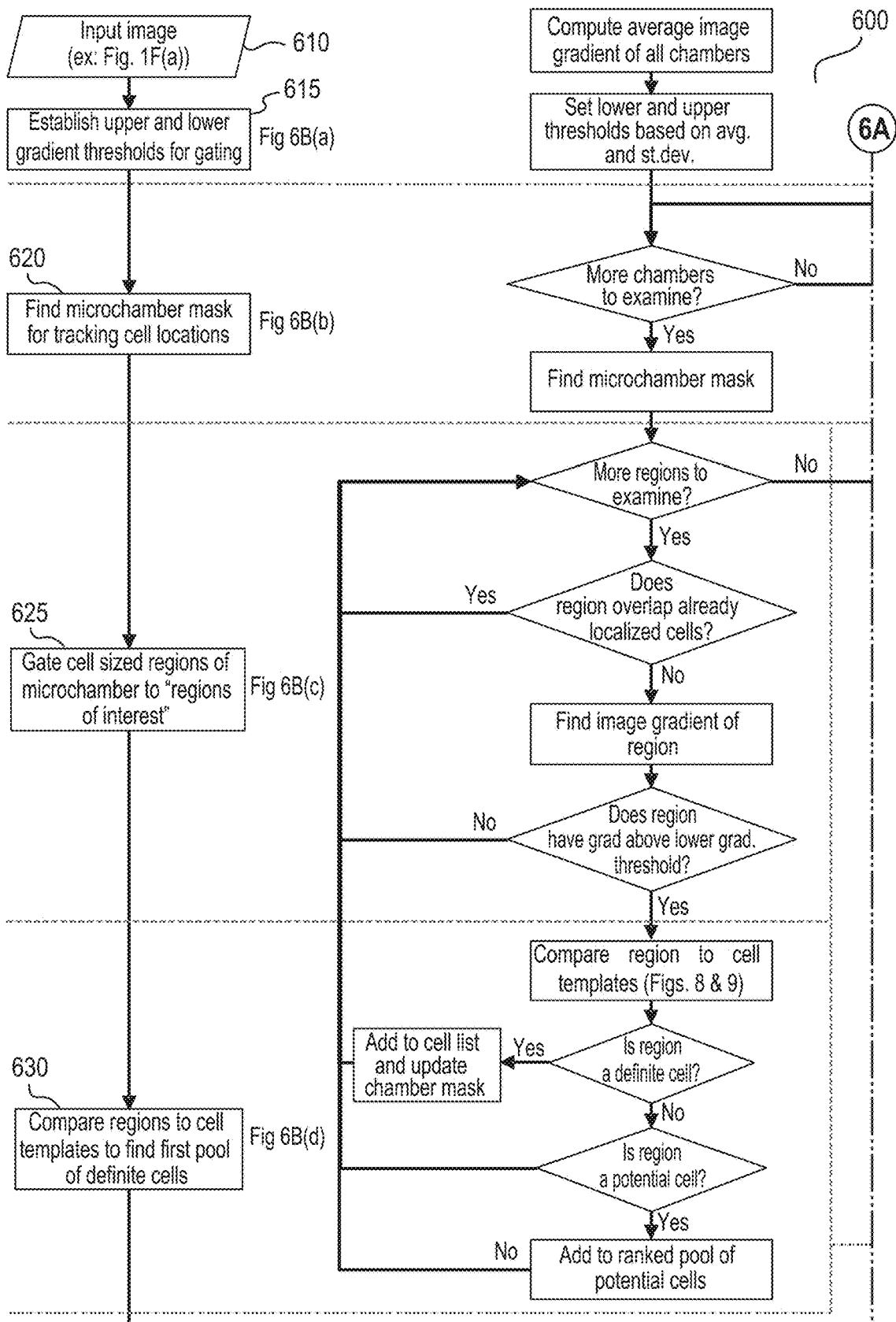
Figures 2, 6A:
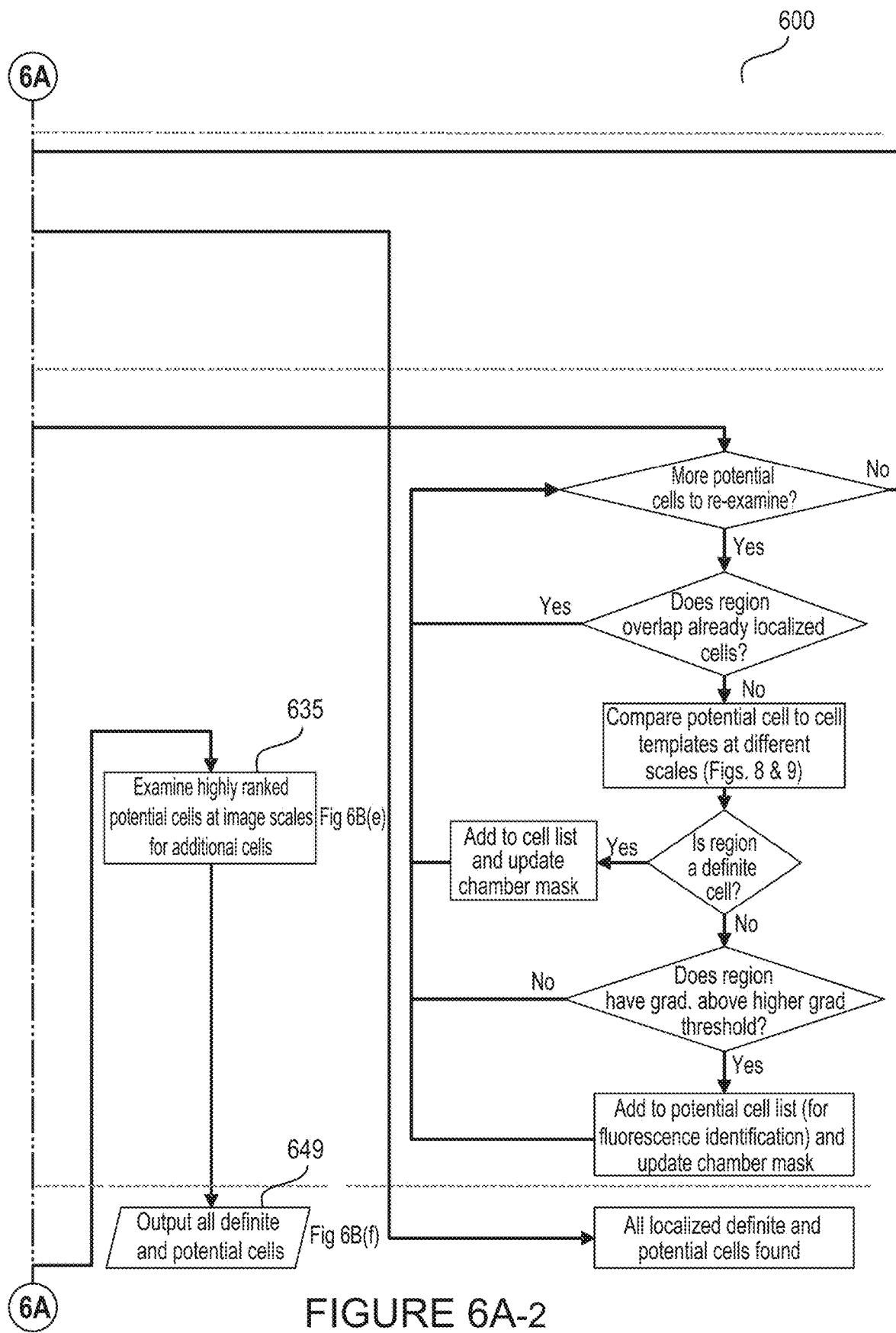

FIG. 6A illustrates an exemplary detailed process 600 for cell/particulate location identification. Commencing in state 610 acquired light field images for the various sample retention regions 124 may be used. Such images may include the first or second light field images depicted in FIGS. 1F(a) and 1F(b). Cell localization 600 may include establishing an upper and lower boundary or gradient threshold (step 615) used to determine criteria for including or excluding cells based on candidate identifications. In various embodiments, thresholds may be determined by computing an average or mean image intensity gradient for selected chambers/sample retention regions 124. Thereafter, upper and lower boundary thresholds may be determined using statistical parameters or calculations such as identifying boundaries based on a selected number or percentage of standard deviations from the average or mean image intensity gradient. The image intensity gradient may then be used in subsequent analysis to include or exclude candidate cells/particulates in a readily automated manner.

To establish potential locations 660 where candidate cells/particulates may reside, one or more sample region masks or boundaries are identified (state 620). Depicted in the exemplary visualization 650 in FIG. 6B, the sample regions boundary mask 655 provides a convenient tool to delineate areas 658 that are to be searched or analyzed for cells/particulates 106. The masks 655 may further serve to enumerate chamber or particle retention regions or areas to be considered and a logical flow may be applied where each area 658 is analyzed separately (serially or in parallel) proceeding until all areas 658 have been processed. In state 625, for each area 658 delineated by a boundary mask 655, putative cell/particulate identifications 662 may be made. The identifications 662 may be based on selected criteria such as size/dimensionality of features located in the area 658 under consideration. These criteria may further match or conform to expected proportionality or criteria that cells/particulates 106 located in the areas 658 may be expected to meet. Cell/particulate identification may include one or more features within the respective areas 658 delineating one or more potential cell/particulate identifications. Each putative cell/particulate identification 662 may further comprise performing a gradient intensity analysis where, based on established gradient thresholds determined above, candidate cells/particulates 106 may be identified as described in greater detail hereinbelow.

To improve the accuracy of cell/particulate determination and/or to select or discriminate between desired cells/particulates 106, a feature template comparison is performed (state 630). FIGS. 6C and 6D depict exemplary cell template matching processes 670, 672 corresponding to the feature template comparison process. In various embodiments, a collection or catalog of multiple cell/particulate template images 674 may be obtained. The catalog may further be used to compare against images or regions having a putative cell(s)/particulate(s).

In various embodiments, cell templates 674 retrieved from a database are compared to designated regions/areas corresponding to putative cells/particulates of interest for each sample retention area 124. Multiple imagings/renditions 678 of both the cell/particulate template 674 and/or the selected region 676 under consideration may be made. The images 674, 676, 678 may further be normalized, scaled, and/or balanced by various operations (for example normalizing intensities to a range of approximately 0-1). In various embodiments, the multiple renditions 678 may comprise various intensity gradients and/or magnitude for the various images (for example, representing changes in intensity or magnitudes for the original and/or template image).

Applying a directional gradient imaging approach, selected or calculated changes in intensity for the images may be determined. As illustrated, three gradient images are depicted for the putative 676 and template 674 images. Each of the three corresponding pairs of images may then be compared to each other (for example pixel by pixel) to determine similarities and differences between the putative 676 and template 674 images. In various embodiments, a total intensity difference across the various images is computed and a similarity measure between the putative region 676 and the template 674 is determined. This information may be used in connection with designated thresholds to both include or exclude putative cell/particulate identifications as well as to further classify the identifications as potential/lower accuracy/false positive identifications 682 or definitive/higher accuracy/cell match identifications 684. State 630 is completed with the retention of definitive/higher accuracy/cell match identifications 661.

To increase the percentage of productive cell/particulate analyte analysis, potential/lower accuracy/false positive identifications 682 may be re-examined in state 635. For example, putative identifications that were not designated as definitive but nonetheless were highly ranked or likely cell/particulate candidates may be considered against the previously described criteria where additional cells/particulates may be included or retained as definitive/higher accuracy/cell match identifications 661.

Figure 6B:
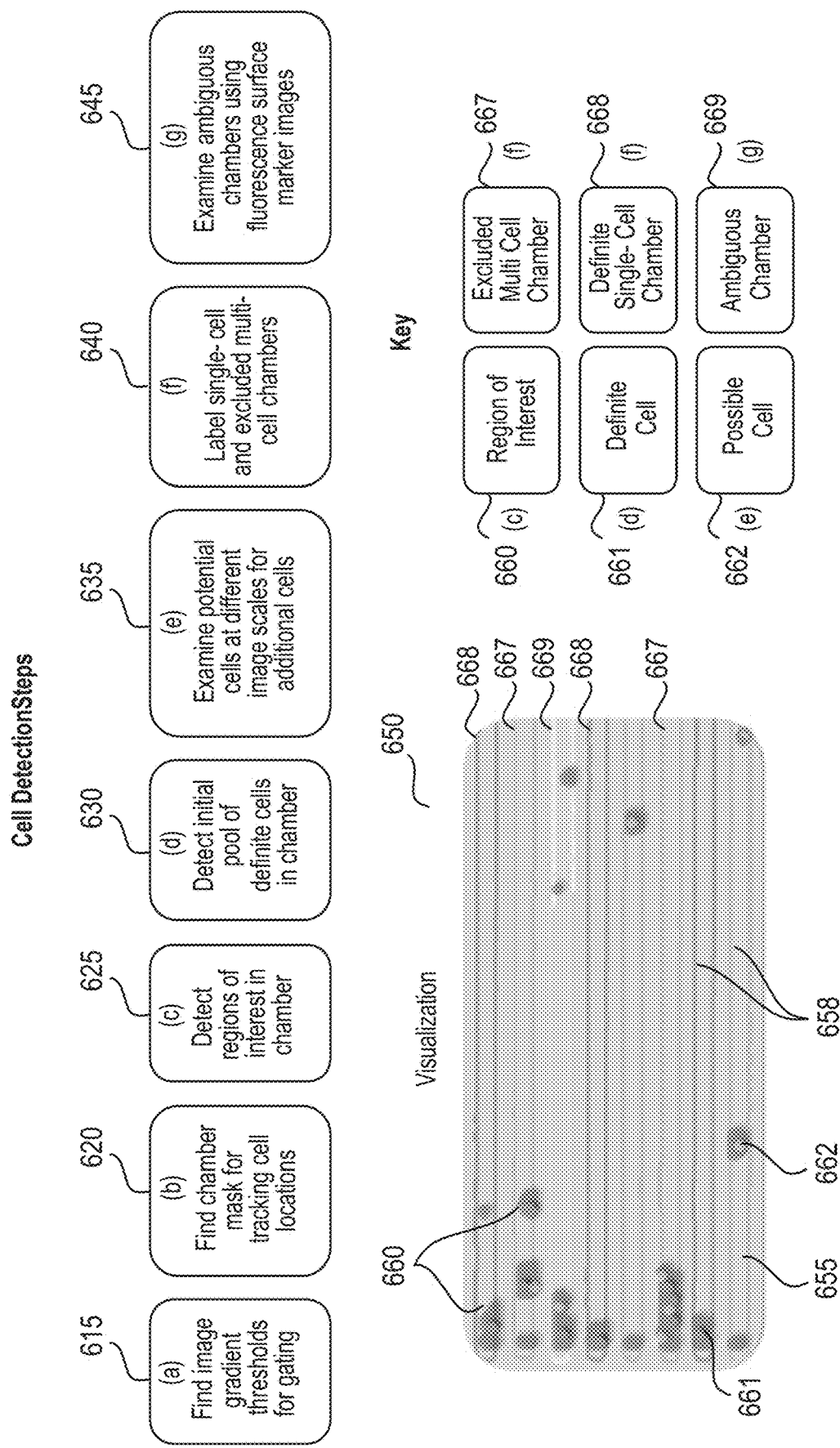
FIG. 6B illustrates an exemplary cell detection and visualization method for sample region boundaries according to the present disclosure.
Figure 6C:
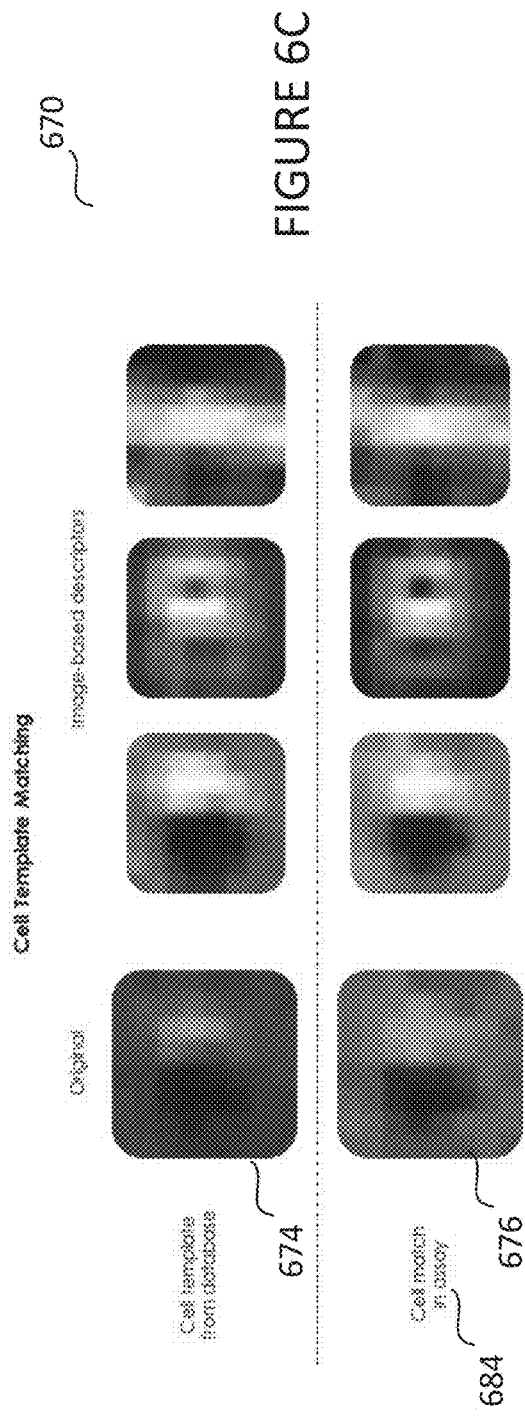
FIG. 6C depicts an exemplary cell template matching processes according to the present disclosure.
Figure 6D:
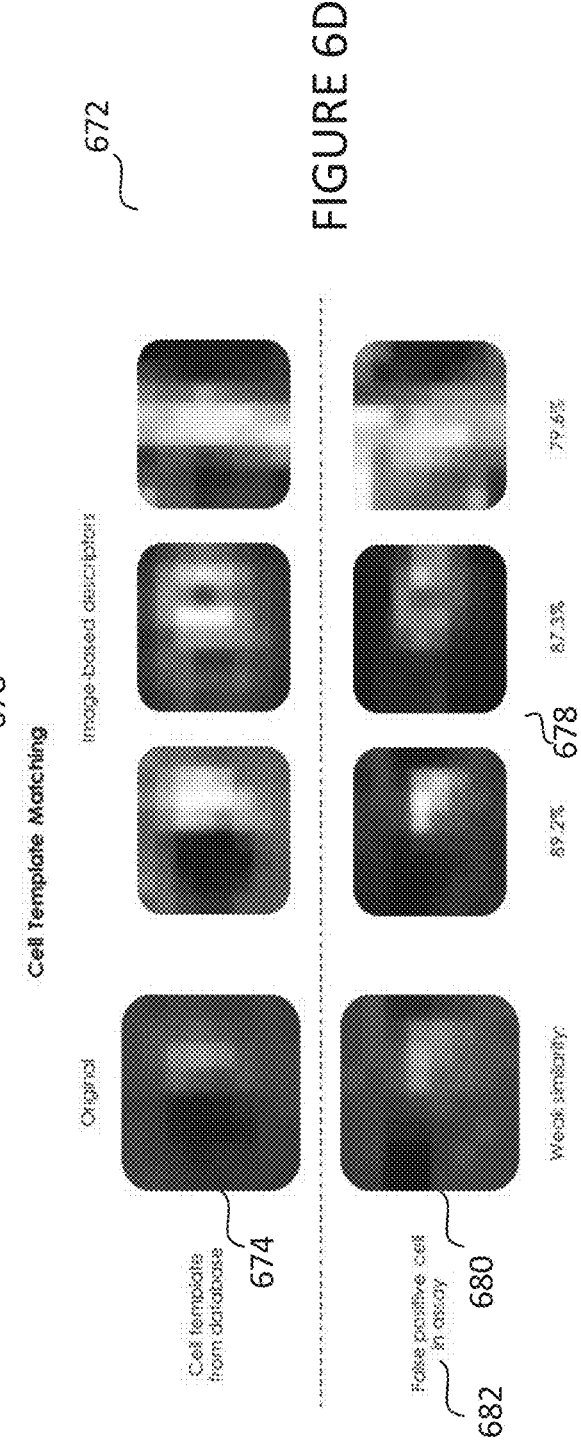
FIG. 6D depicts an exemplary cell template matching processes according to the present disclosure.

As shown in FIG. 6B, sample region masks or boundaries 655 and corresponding areas 658 may further be classified on the basis of cells/particulates identified in the processes above. For example, from the number of cells/particulates associated with a selected area 658, the region may be designated or flagged to be excluded from further analysis 667 (for example as containing multiple cells/particulates in a single cell experiment or analysis). Other areas 658 containing a desired number or cells/particulates may be designated or flagged to be included in further analysis 668 (for example as containing a single cell/particulate in a single cell experiment or analysis). Further, regions or chambers for which ambiguous results were obtained (for example where a clear identification of the presence or absence of a cell/particulate could not be made) may be flagged 669. In various embodiments, ambiguous chambers or regions 669 may be subjected to further processing or examination 645. In some instances, such regions 669 may be evaluated in connection with additional images/scans obtained for the sample array 122 such as the fluorescent cell stain/marker image depicted in FIG. 1F(c). In some cases, additional processing in the aforementioned manner may improve the confidence of cell/particulate identification and "rescue" associated regions which may be retained for further analysis.

The cell/particulate location identification process 600 depicted in FIG. 6A is completed with the output of image classifications in state 649. Output from the process 600 may include information relating to the identified cell/particulates 102 (e.g. location or positioning within the respective sample retention region, confidence determinations, cell/particulate classification or identification, etc.). Further information concerning the identified sample retention regions 122 may additionally be output including information relating to the number of cells/particulates 106 contained in respective regions and the overall quality of region imaging.

Figure 6E:
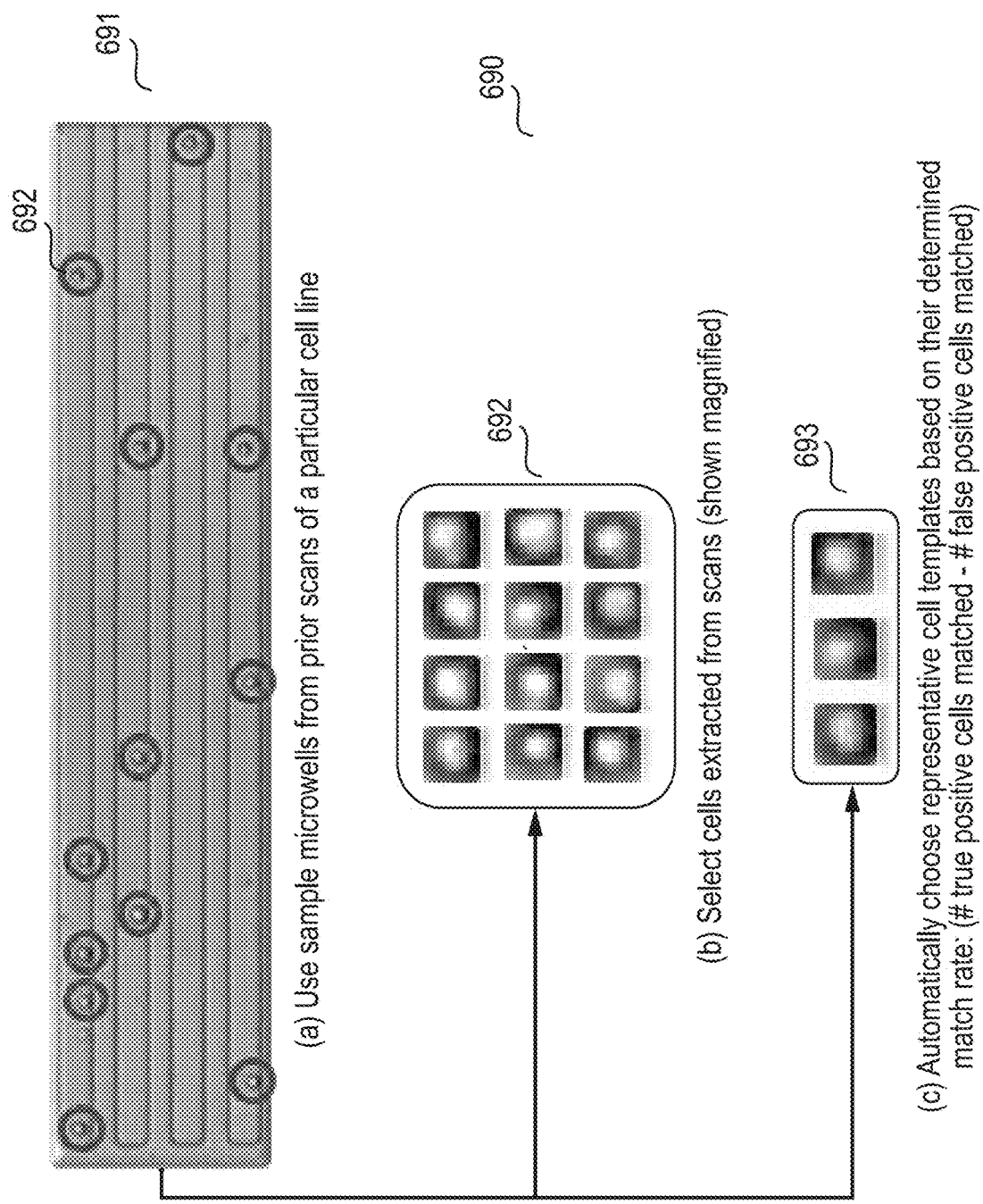
FIG. 6E depicts an exemplary process for generating a cell/particulate template library according to the present disclosure.

FIG. 6E depicts an exemplary process for generating a cell/particulate template library, database or population 674 for comparison in connection with the aforementioned methods identified in association with FIGS. 6C and 6D. Using previous imagings or scans 691 of known cells/particulates, one or more representative cell/particulate images 692 may be identified. In various embodiments, identification of a subset of cells/particulates 692 having varied characteristics (e.g. different morphologies, sizes, intensities, or other properties) may be associated with a selected type or class of cell/particulate 106. The subset 692 may be further refined and improved to form a representative cell/particulate subset 693 using data and information obtained from experimental results and analysis. In various embodiments, automated methods may select representative cell/particulate templates by applying criteria that consider similarities in morphology, experimental quality, confidence in match rates, and other criteria. Various representative cell/particulate subsets 693 may be collected from different experiments, literature descriptors and information, and other sources, improving the dataset over time. Additionally, in some instances, a representative cell/particulate subset may be determined in real time using images and data from a current experiment in which selected cell/particulate images are used as a template or basis for comparison against other cell/particulate images. In various embodiments, representative cell/particulate images are preferentially selected that are dissimilar in appearance to other false positive or undesired cells or particles that may reside in the sample retention regions 124.

Referring again to FIG. 1D, analyte patterns 142 associated with one or more scans obtained from imaging of the analyte detection substrate 134 are aligned and oriented (steps 1310, 1320) with selected images (e.g. first and second images for example corresponding to the high and lower resolution images) of the sample array 122. As previously described, association of the sample retention regions 124 with the analyte patterns 142 provides the ability to determine analytes 108 secreted, released, or associated with cells/particulates 108 residing in selected sample retention regions 124. In various embodiments, a plurality of imagings of the analyte patterns 142 may be obtained, for example, using differing spectral or optical characteristics during the imaging process. Multiple imagings in this manner may be used to resolve co-located or multiplexed analyte detection moieties 135 within the same analyte detection region 136 having discretely identifiable and/or spectrally separable labels or dyes providing the ability to distinguish multiple analytes 108 from a particular region of the analyte detection substrate 134.

Figure 7A:
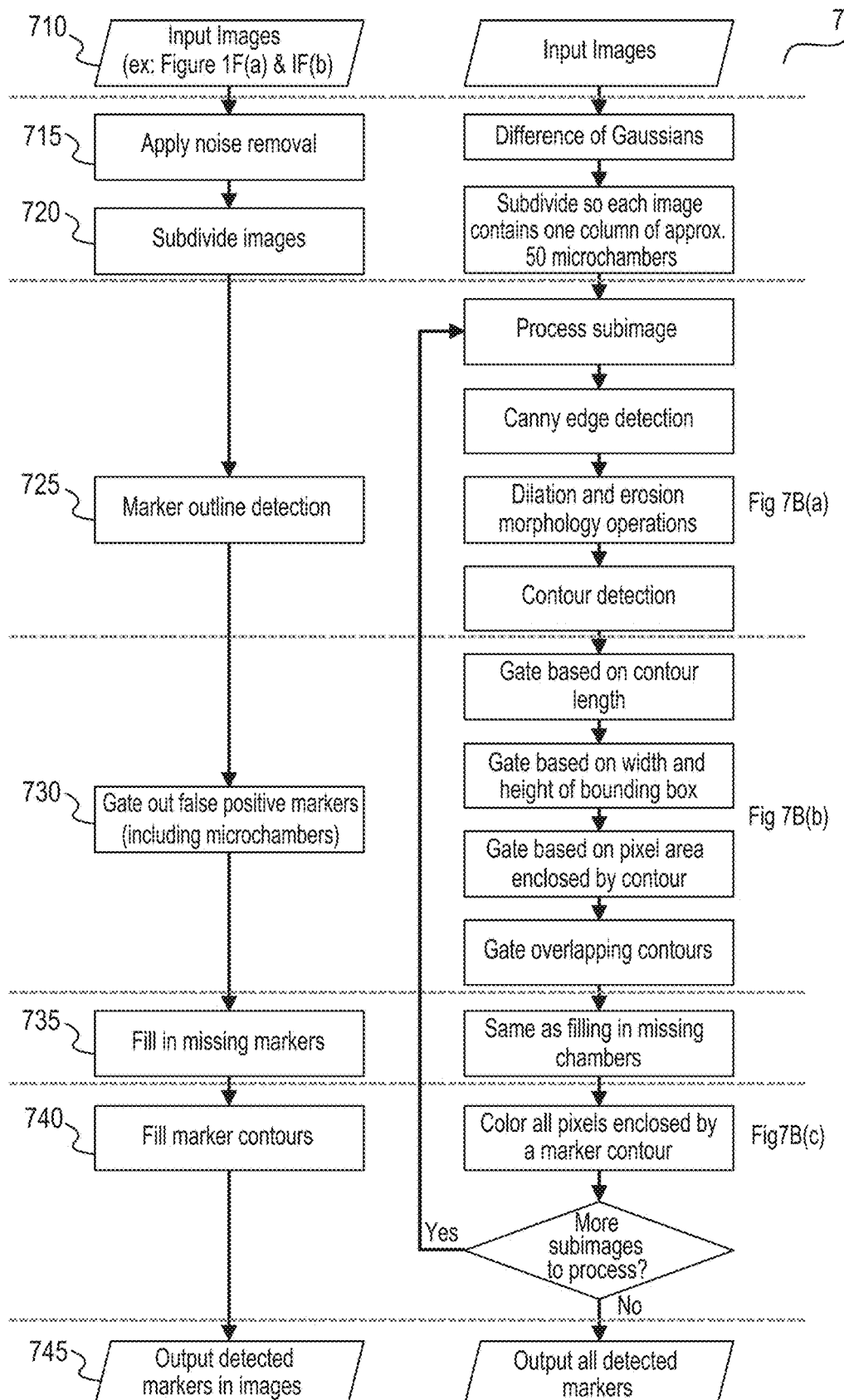
FIG. 7A depicts an exemplary workflow for alignment of images and scans according to the present disclosure.
Figure 7B:
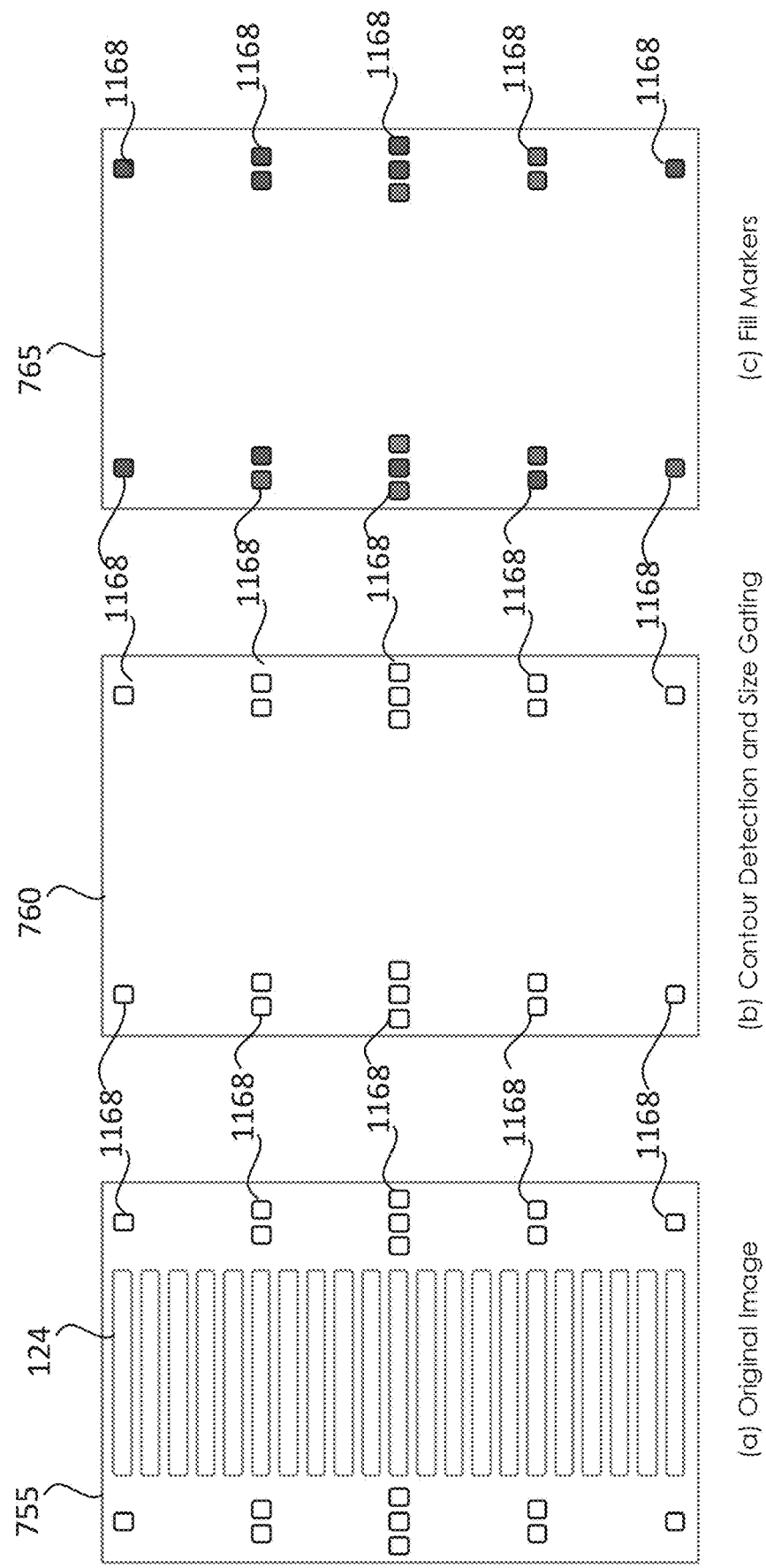
FIG. 7B illustrates exemplary operations applied to exemplary images and scans using alignment markers according to the present disclosure.

FIG. 7A depicts a detailed workflow for alignment of images and scans discussed above. FIG. 7B further illustrates the operations applied to exemplary images and scans using fiducials/alignment markers 1168. According to various embodiments, the first and second images of the sample retention regions 124 corresponding, for example, to higher and lower resolution images, may have different regions of interest. The imaging apparatus (e.g. a scanning optical microscope) may acquire multiple sub-images (e.g. on the order of tens or hundreds) based on different selected regions of interest. While these images may be tiled or aligned with respect to one another, such processes may be imperfect and results may vary significantly between high and lower resolution images.

To alleviate potential problems in alignment and to improve the overall accuracy alignment markers 1168 are located about the sample array 122. In various embodiments, the alignment markers 1168 may appear adjacent or in proximity to selected sample retention regions 124 as previously described. Alignment markers may be present for each column of sample retention regions 124 or disposed in various other positions about the sample array 122. In various embodiments, the number and/or size of the alignment markers 1168 may be varied in a repeating fashion or with a selected ordering further facilitating adjustment and alignment of the images and scans.

In various embodiments, due, in part, to inconsistencies or variations in the regions of interest, images may be desirably aligned to allow precise matching or alignment of scans corresponding to the detected analytes 108 with the corresponding images identifying the cells/particulates 106. In some instances, due for example to tiling inconsistences as well as the small feature sizes (e.g. sample retention regions 124/analyte detection regions 136) of the sample array 122 and the analyte detection substrate 134 and further including potential variations, inconsistencies, and issues associated with the features themselves, a single global alignment operation may be insufficient for accurately aligning all regions in all images/scans. Consequently, it is often desirable to provide mechanisms to locally align regions of each image/scan using subsets of alignment markers.

According to methods described in association with FIG. 7A first (e.g. for example high resolution) normal or light-field images may be readily aligned with second (e.g. for example lower resolution) normal or light-field images. In various embodiments, the process of image and scan alignment is facilitated by the lower resolution images having similar fields of view and tiling as the analyte scans reducing alignment complexities. In step 710, one or more first (high) and second (lower) resolution images (corresponding for example to those depicted in FIGS. 1F(a) and 1F(b)) may be selected as inputs into the marker detection and alignment process 700. A noise removal operation (step 715) improves the image quality and removes artifacts. Such as process may be accomplished using for example a difference of Gaussians approach as well as other noise removal methods. Input images are subdivided (step 720) such that each image comprises a range of selected or desired number of sample retention regions 124. For example, image subdivisions may be performed such that each sub-image comprises approximately a single column of sample retention regions 124 (for example between 10 and 100 or other selected amount).

For each sub-image, alignment markers 1168 may be identified by applying a marker outline detection method (step 725). In various embodiments, a Canny edge detection approach may be utilized. Edge detection may further comprise performing other quality assessments of the features contained in the images, such as, dilation and erosion morphology assessments of the alignment marker regions as well as feature contour detection. FIG. 7B illustrates an exemplary processing of sub-image region 755 comprising a plurality of alignment markers 1168 and associated sample retention regions 124. The original image 755 may be transformed according to the contour detection and size gating operations described above to discretely identify or locate the various alignment markers 1168. Following marker outline detection method (step 725), false or erroneous marker identification may be performed (step 730). To help insure actual or well resolved alignment markers are used in subsequent alignment operations, the detected markers may be evaluated based on various criteria. For example, the dimensionality or positioning of the alignment markers and sample analyte regions may be evaluated as well as the pixel areas associated with the various alignment markers. Overlapping contours representative of poorly resolved alignment markers may further be evaluated. In the various alignment marker assessment operations described above, low quality and/or poorly resolved alignment markers may be excluded from further analysis therefore desirably avoiding potential downstream alignment issues. In various embodiments, the number of alignment markers present in a respective sub-image is desirably redundant or in excess of what may be used for image/scan alignment. Such redundancy provides greater tolerance and flexibility to the alignment processes.

In addition to identifying false positive, low quality, and/or poorly resolved markers, the method 700 may include processes for identifying the expected locations for missing alignment markers or providing fill-in operations to correct for low quality and/or poorly resolved markers (step 735). Following these processes, remaining alignment markers 1168 may be more clearly identified by shading, coloring, or other methods to help insure the markers are clearly distinguishable within respective sub-images (step 740 and further illustrated in FIG. 7B(c)). The resulting identified and processed alignment markers 1168 and associated sub-images 765 may then be output for further processing (step 745).

Referring to FIG. 1D, as discussed above, similar operations 1310, 1320 may be used for each sub-image 755 associated with the various images obtained in the high and lower resolution imagings (for example, FIGS. 1F(a) and 1F(b)) resulting in processed images having high quality alignment markers 1168 identified in each instance. Thereafter, corresponding first (e.g. high resolution) and second (e.g. lower resolution) images may be aligned with respect to each other.

Figure 7C:
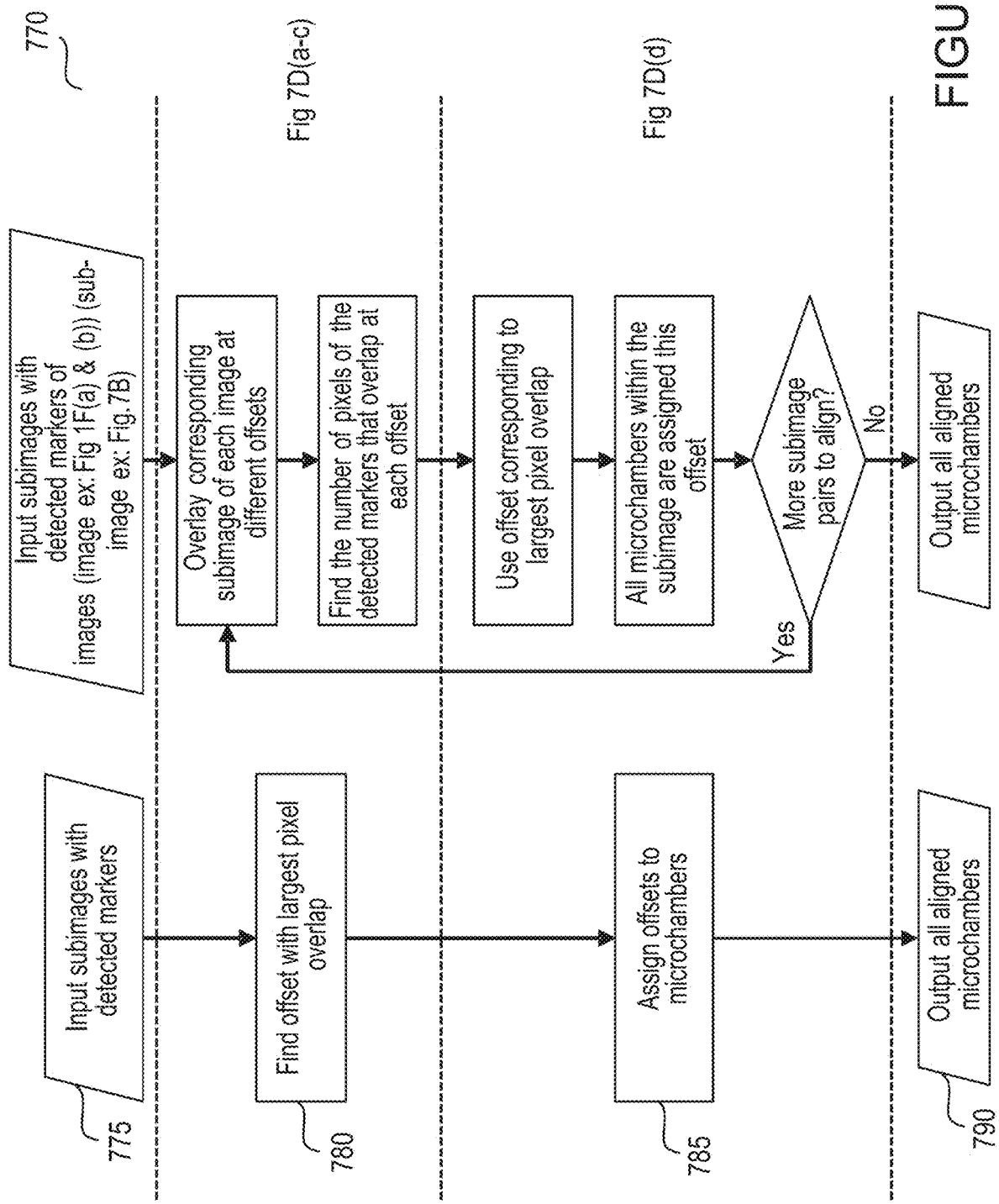
FIG. 7C depicts an exemplary method for first and second image alignment according to the present disclosure.
Figure 7D:
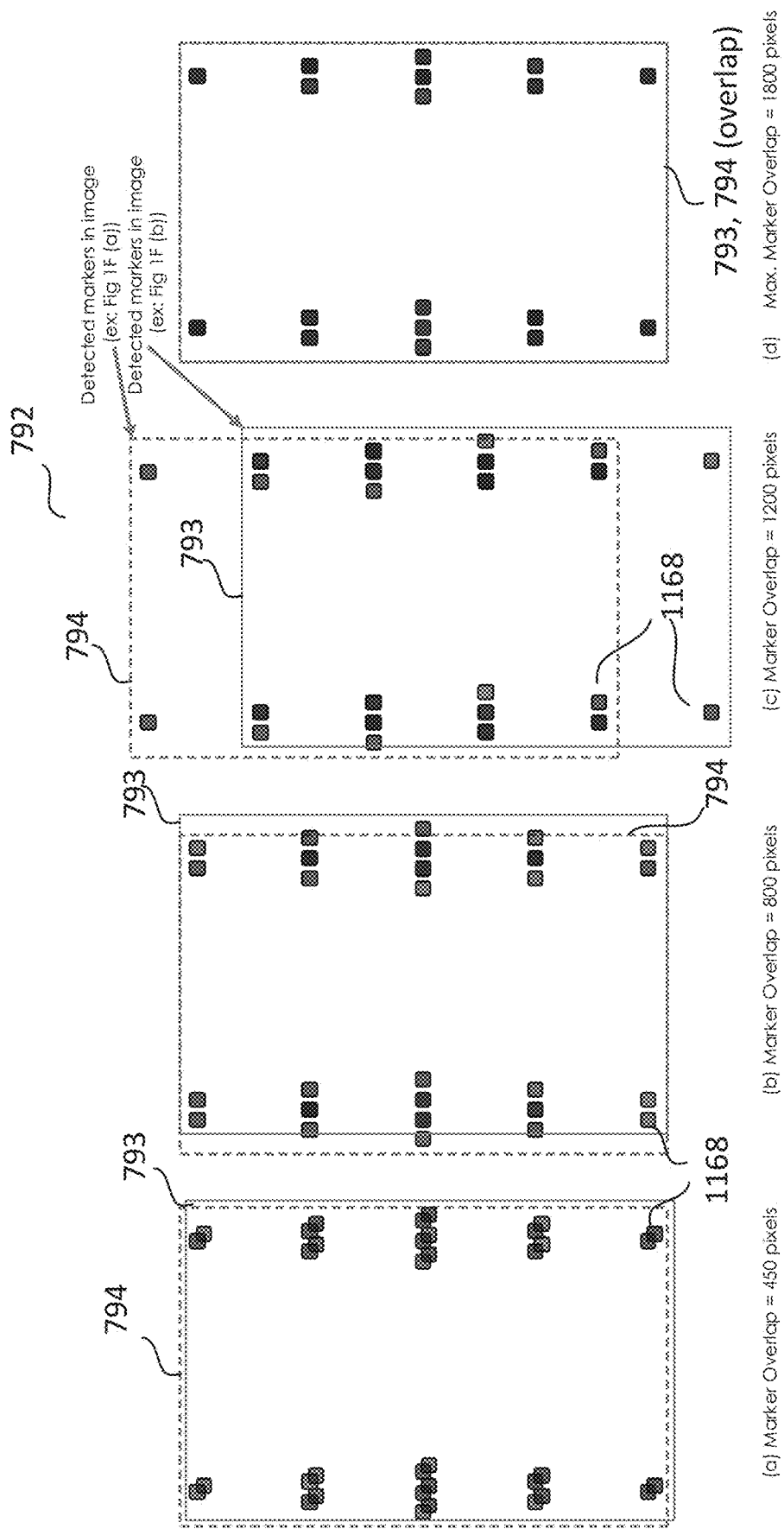
FIG. 7D illustrates an exemplary process for first and second image alignment according to the present disclosure.

An exemplary method 770 for first and second image alignment is shown in FIG. 7C with corresponding exemplary illustration 792 for the alignment process shown in FIG. 7D. Initially, sub-images with detected and validated alignment markers for corresponding first (e.g. high resolution) and second (e.g. lower resolution) images are received for processing (step 775). As previously described, multiple sub-images may be desirably aligned corresponding to similar or identical regions of interest. Sub-image alignment proceeds selecting a first sub-image to be overlaid/oriented by a corresponding second sub-image applying one or more offsets to aid in the alignment process (step 780).

Each offset may be representative of a shift in positioning the respective image frames with an offset distance determined, for example, by a number of pixels reflecting the offset distance or position. For each offset, detected alignment markers present in each sub-image are evaluated to determine the number of alignment markers that overlap between the respective sub-images. As will be described in greater detail, the number and degree of overlap between the alignment markers may be used as a factor in determining the extent or quality of sub-image overlap. For the various selected or determined sub-image offsets, the image offset with the largest pixel/alignment marker overlap may be identified.

FIG. 7D illustrates the multiple offset process of step 780 where a selected sub-image 793 is overlaid/oriented with another associated sub-image 794 for discrete offset intervals (a), (b), (c), and (d) corresponding to approximate alignment marker overlaps of 450 pixels, 800 pixels, 1200 pixels, and 1800 pixels respectively. Using the image offset corresponding to the largest pixel overlap (e.g. (d) in FIG. 7D), sample retention regions 124 within the sub-image are assigned or associated with the selected offset (step 785). This process may then be repeated for additional corresponding sub-images until substantially all corresponding sub-images across the one or more first and second images is completed. The output of the process 770 provides details and values for the alignment of the associated sample retention regions 124 in each sub-image for each corresponding first and second images. The aligned images may then be used in downstream processing and further associated with the analyte patterns as will be described in greater detail hereinbelow.

Referring again to FIG. 1D, detection and resolution of the discrete analytes 108 secreted or released by cells/particulates 106 located in respective sample retention regions 124 of the sample array 122 requires association and alignment of the corresponding fingerprint, barcode, or analyte patterns 142 formed on or associated with the analyte detection substrate 134. As noted elsewhere, the small size and large number of features visualized across multiple images and scans make it important to provide highly accurate means for orienting and aligning the images and scans with respect to each other. Misalignments can lead to poor quality data analysis including missed and erroneous analyte identifications. The methodologies described herein desirably avoid such problems and provide highly accurate means to associate and evaluate the images and scans.

In various embodiments, addressable fiducials or alignment markers 1168 are advantageously leveraged identifying and positioning associated images and scans with respect to one another. For example, alignment markers 1168 associated with, positioned about, or aligned with sample retention regions 124 of the sample array 122 (e.g. detected in images 1F(b)) may be used in connection with corresponding or other alignment markers 1171 associated with or positioned about analyte detection regions 136 of the analyte detection substrate 134 (e.g. detected in images 1G(b)).

It will be appreciated that a precise and/or unique alignment is desired between the sample array 122 and the analyte detection substrate 134. Such alignment helps insure microchambers/sample retention regions 124 are appropriately aligned with corresponding flow lanes/analyte detection regions 136. In this regard, various types, numbers and/or positionings of alignment markers 1168, 1171 may help facilitate identification of optimal alignment between the various images and scans of the sample array 122 and analyte detection substrate 134.

Figure 8A:
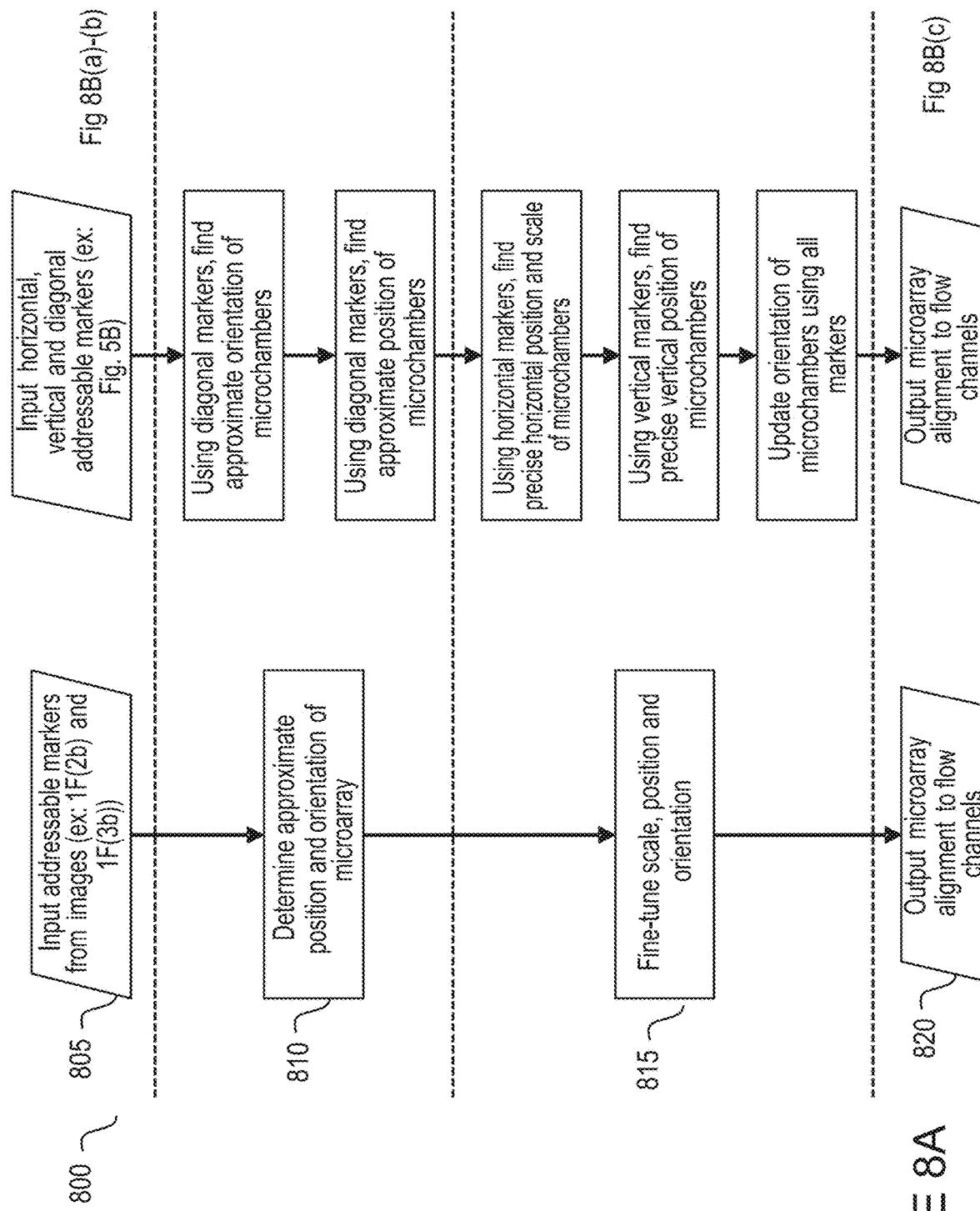
FIG. 8A depicts an exemplary process 800 for association and alignment of features according to the present disclosure.

Alignment markers 1168, 1171 may further aid in resolving variations in scale or differences in imaging characteristics between scans and/or images. For example, rotational and/or translational differences may exist between the images and scans that are desirably accounted for and corrected to improve alignment. To address these issues, accurate alignment marker detection is desirable and may be used to precisely align the various imagings. Several variables may be considered during alignment marker identification and resolution including, for example, x and y translations or offsets, image/scan rotational angle differences, and image/scan scaling factors. Taking these factors into account, detected alignment markers may be used to orient the sample retention regions 124 with analyte detection regions 136 with a high level of accuracy. FIG. 8A illustrates a detailed process 800 for association and alignment of the above-indicated features. FIG. 8B provides an illustration 850 of the processes described in FIG. 8A for an exemplary sub-image portion of sample retention regions 124 with corresponding analyte detection regions 136.

In step 805, alignment markers detected from corresponding scans of the analyte detection substrate 134 and sample array 122 may be collected and associated. (For example FIGS. 1F(2b) and 1F(3b)). Alignment markers may be positioned about the surfaces of the analyte detection substrate 134 and sample array 122 in various manners to aid in orientation in various directions such as horizontally, vertically, and/or diagonally. By way of example, alignment marker details and alignment information may be obtained from preceding steps such as information generated during analysis of analyte detection region location and identification (ex: FIG. 5). In step 810, an approximate position and orientation of selected sample retention regions 124 may be determined using selected alignment markers (ex: diagonal markers). In step 815, additional operations to refine the first determined positioning and orientation of the sample retention regions 124 may be performed. Using one or more different sets of alignment markers (ex: horizontal markers and/or vertical markers) more precise positioning and scaling of the sample retention regions 124 may be performed according to one or more operations. The updated position and alignment details of the sample retention regions 124 may then be used to align against the positioning for associated analyte detection regions 136. The results of the alignment for the respective images and scans are then output in state 820.

FIG. 8B provides an illustration of alignment 850 between sample retention regions 124 and analyte detection regions 136. In panel 855, a sub-image is depicted for detected flow lanes corresponding to the analyte detection regions 136 that may be determined from positioning of associated alignment markers 856. In panel 860, a sub-image with corresponding sample retention regions 124 is depicted with alignment markers 857. It can be noted from the image that the relative positioning of the two images appears slightly offset with respect to one another. Using the processes described above, the alignment markers 856, 857 from the two sub-images 855, 860 can be leveraged to help provide more precise alignment between the two sub-images. Thus, in sub-image 860 positioning and aligning using the two sets of alignment markers 856, 857 provides an accurate approach to visualizing analyte patterns 142 formed at intersections of the sample retention regions 124 and analyte detection regions 136. These regions of overlap further correspond to positions where signals for analytes 108 are expected to reside based on the type of analyte detection moiety 135 disposed therein as well as the presence of a detected analyte 108 secreted or released from one or more cells/particulates associated with the sample retention chamber 124.

Referring again to FIG. 1D, in step 1340 the location and positioning of analyte detection regions 136 is determined. In various embodiments, location information for the analyte detection regions 136 may be aided in part from previous analysis, calculations, and evaluations. For example, image analysis operations and information for alignment feature identification in steps 1220, 1240 may be leveraged to further identify associated flow lanes/analyte detection regions 136 (see also FIGS. 3 and 5). As shown in FIG. 5(f), located positions and orientations of alignment features/markers may be used to further identify flow lanes/analyte detection regions 136 associated with detected alignment features/markers based on expected positioning of the flow lanes/analyte detection regions with respect to the alignment feature/markers.

As shown in the analysis workflow 1000, steps 1400, 1410, and 1420 may be used to perform additional operations for cell/particulate identification. For example, in cell-based assays (e.g. single cell assays and/or cell-cell interaction assays) and associated analyte 108 analysis it may be desirable to conduct additional operations to discriminate between various different cell types. Additionally, it may be desirable to evaluate or determine the physiological or biochemical status of selected cells 106 for which analytes 108 are detected. According to various embodiments, one or more cell surface markers (e.g. for example surface markers corresponding to CD4+, CD8, and/or CD3) may be detected and/or other stains or dyes evaluated (e.g. for example vitality stains or dyes).

According to various embodiments, selected cell populations and cell characteristics may be identified, sorted, and/or distinguished by detection of one or more representative cell surface markers or indicators of expressed membrane associated/secreted proteins. Singular cells as well as multiple cells 106 retained in selected sample retention regions 124 may thus be exposed to various markers, dyes, stains, and/or reagents that are evaluated in addition to or in connection with the analyte patterns 142 resulting from secreted or released chemicals, biochemicals or other cell-associated constituents.

During single cell or few-cell analysis, the above-described identification and characterization operations may further be used to refine and/or confirm cell location and positioning within a selected microchamber or sample retention region 124 (step 1400). Such processes may proceed using the various acquired images and scans evaluating characteristic optical properties or cellular features associated with cells visible in the images and scans. For example, it may be observed that when a cell is labeled, marked or stained with appropriate dyes and/or antibodies, the cell position may be determined by a generally high fluorescence or signal intensity. Such signals may further indicate, for example, the presence of one or more corresponding and discernable surface markers (e.g. CD4+, CD8, and/or CD3) associated with the cell or in the case of vital stains or other dyes some other discernable characteristic (e.g. for example live vs dead cells).

Detected fluorescence or high signal intensities for cell surface markers provide a good indication of the positioning of the cell which is expected to be located close to or exactly in the same area as the observed fluorescence or observed signal. In some instances, however, surface marker antibodies, dyes, stains, or other markers may generate relatively noisy or diffuse signals that may result in areas of relatively high background within the sample retention region 124 containing the cell 106. High background or noise may obscure visualization or detection of cells/particulates 106 associated with the sample retention region 124. These high-background sample retention regions 124 may be desirably identified, flagged, and/or excluded from further analysis (step 1410).

Additionally, signal intensity or fluorescence may exhibit variance between cells/particulates 106 in different sample retention regions 124, vary from experiment to experiment, and/or vary with the quality or characteristics of the stain, marker, or dye used. In some instances, there may be a population of cells/particulates 106 that do not exhibit a detectable signal or possess only a weak signal despite having a corresponding surface marker or having been labelled with a selected stain, marker, or dye. Furthermore, in instances where two or more cells/particulates 106 of the same type or general characteristics reside in close proximity or next to each other, difficulties in distinguishing the origin of the fluorescence or signal may be observed. For cellular secretion, protein expression, and other types of bioanalysis it may be important to accurately determine the cell type and surface markers or other characteristic associated with each detected cell. Accordingly, it may be desirable to label potential or candidate cell identifications as definite cells or false positive cells based on cell surface markers or other signal properties associated with the cell (step 1420).

Figures 1, 9A:
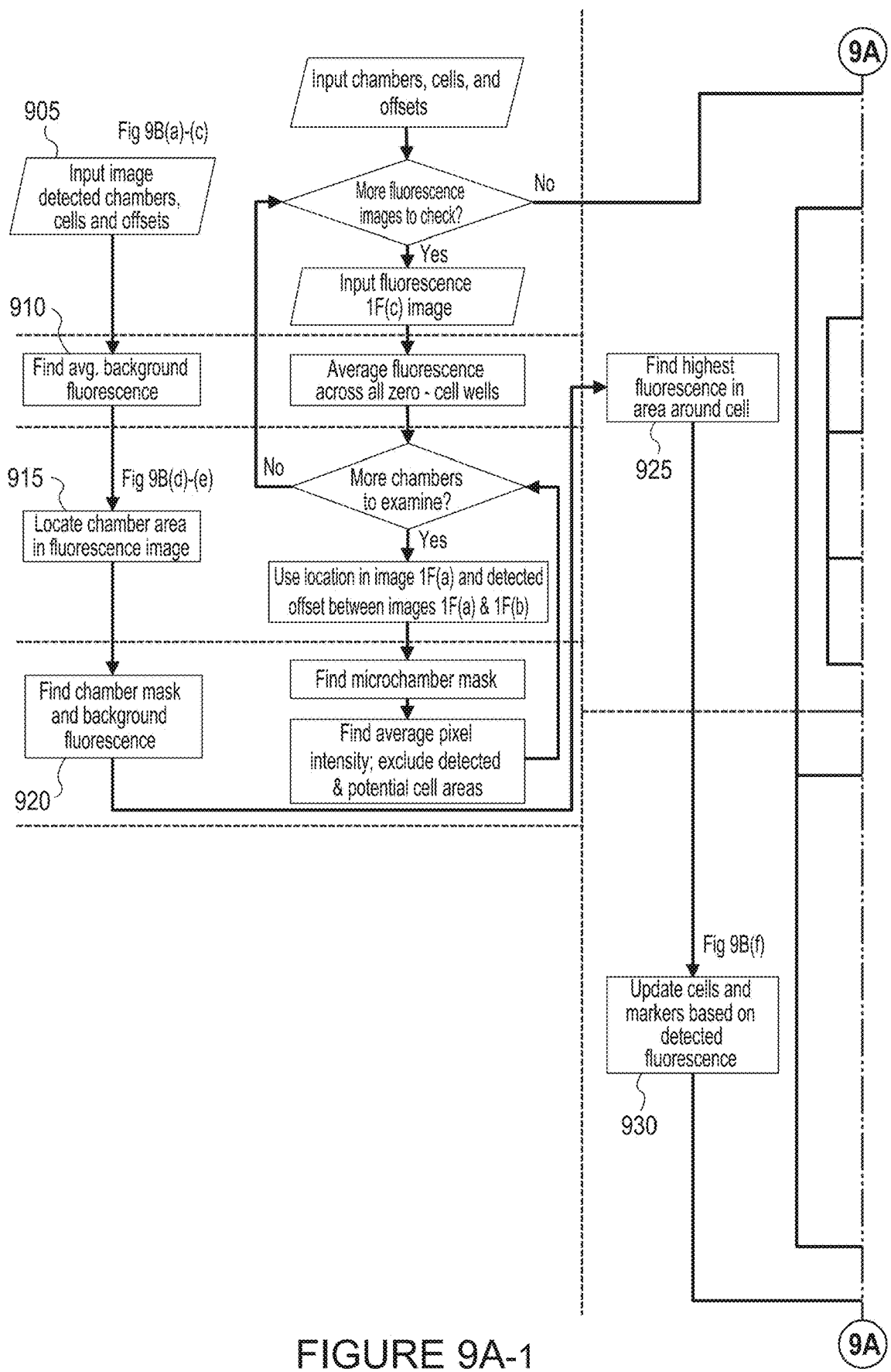
Figures 2, 9A:
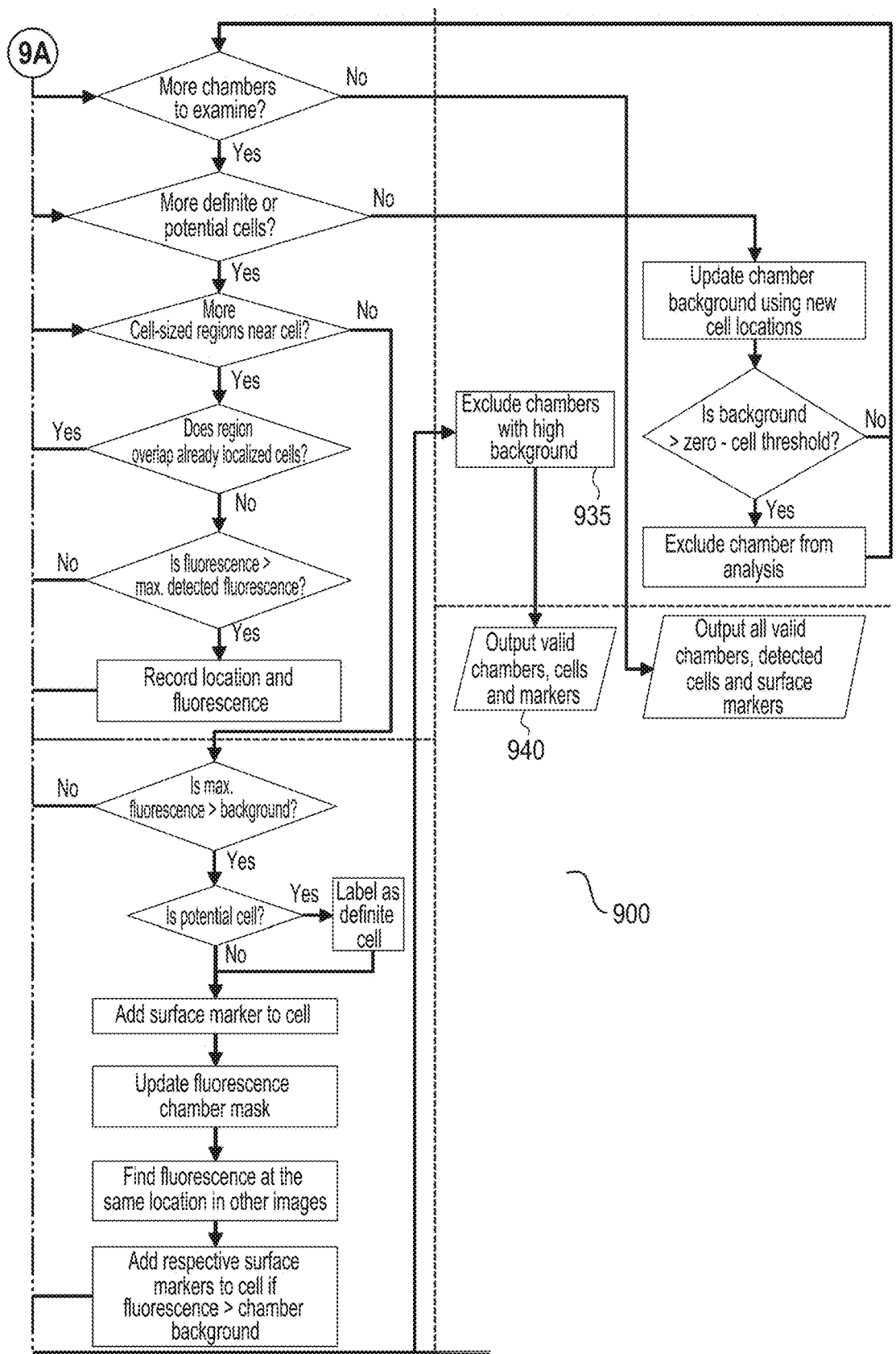
Figure 9B:
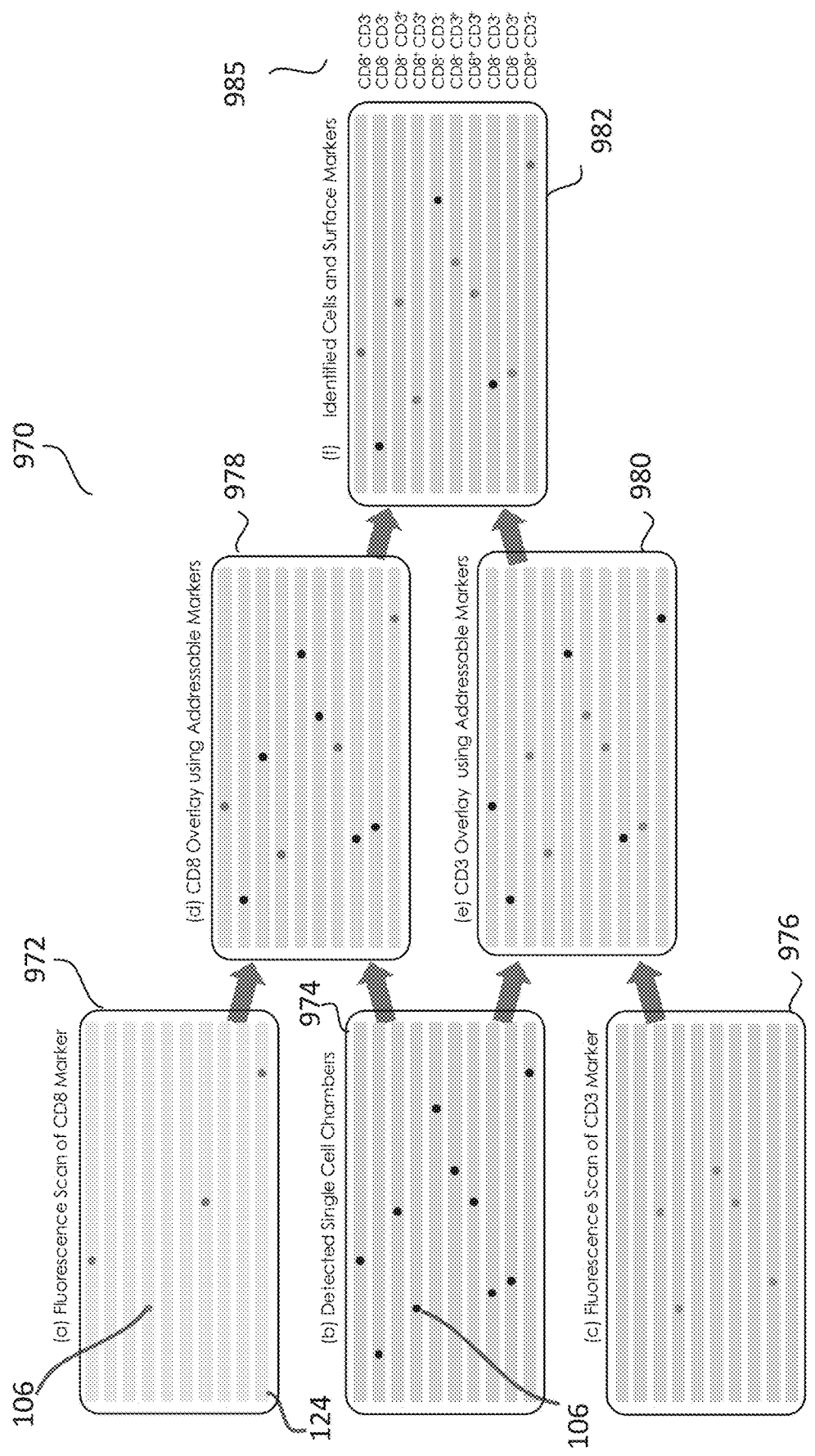
FIG. 9B illustrates an exemplary positioning and discrimination process for cells labelled with surface markers according to the present disclosure.

FIG. 9A depicts a detailed method 900 for cell/particulate position identification and discrimination. FIG. 9B further illustrates the positioning and discrimination process 970 depicting an exemplary sub-set of sample retention regions 124 with cells labelled with surface markers 985 (CD8 & CD3) for cell characterization and discrimination. The process 900 commences with receiving input images corresponding to cell/particulates 106 identifiable with dyes, markers, or labels that can be visualized for example by fluorescence detection (FIG. 1F(c)). As discussed above, the markers may comprise one or more cell/particulate surface markers imaged/scanned simultaneously or at different times and whose data is aggregated through the alignment and positioning mechanisms described herein. Additional information may also be utilized in the alignment process 900 corresponding to identified microchambers/sample retention regions, definite and potential cells candidates, and aligned microchamber/sample retention region information. (for example, obtained from the processes 400, 600, 700 described in association with FIGS. 4, 6, and 7 respectively)

Initially, in step 910 an average background signal or noise ratio may be determined (for example, to identify background fluorescence due to dyes, markers, or labels used in the analysis). The average background signal may further be determined by evaluation of one or more sample retention regions 124 lacking a cell/particulate 106 residing therein. In various embodiments, sample retention regions 124 lacking a cell/particulate 106 may be expected to exhibit lower background or reflect average nominal background present throughout each of the sample retention regions 124.

In step 915, sample retention regions or areas 124 are correlated with the input images (ex: FIG. 1F(c)). This process 915 may further utilize offset information determined previously for first and second aligned images (ex: FIG. 1F(a), 1F(b)). In step 920, a microchamber or sample retention region mask is determined to isolate or localize respective areas to be evaluated. A portion of this process 920 may include identifying an average pixel intensity or density in regions outside of the locations where cell/particulates 106 are detected or predicted to determine background within a respective sample retention region 124. For example, an average pixel intensity may be determined for portions of a selected sample retention region 124 by excluding detected or potential cell areas, signals, or intensities. Thereafter, the background signal (e.g. fluorescence) for a selected microchamber/sample retention region 124 may be determined.

In step 925, the sample retention region 124 may be evaluated further identifying high signal intensities in areas proximal to identified or predicted cell/particulate locations. For example, the highest fluorescent signal residing around or in proximity to a cell/particulate 106 may be determined for one or more surface markers or images. Taking into account the background signal/intensity information identified above and the maximal cell/particulate associated signal present, the relative position of cells/particulates 106 within respective images of sample retention regions 124 may be determined with a high degree of accuracy. This information may be further correlated with the one or more scans of analyte patterns 142 associated with the cell(s)/particulate(s) 106 in the corresponding sample retention region 124.

In step 930, cell/particulate surface marker intensities may be evaluated to determine and quantitate detected markers. In various embodiments, for each cell undergoing analysis the presence of one or more surface markers detected or associated with the cell may be used to determine the characteristics and/or status of the cell. Additionally, for instances where high background signals exist based on the determinations and calculations described above, associated sample retention regions 124 may be flagged and/or excluded from further analysis in step 935. Flagging or excluding sample retention regions in this manner may aid in generation of high quality results and/or prevent anomalous or erroneous interpretation of the sample data. Finally, in step 940 sample retention regions having acceptable background are output along with associated cell/particulate position and identification characteristics including surface marker patterns or descriptors (if present) for further processing.

FIG. 9B provides a pictorial representation 970 of the processes described in FIG. 9A where in an exemplary single cell assay, surface markers for CD3 and CD8 are imaged discretely and aligned. Imaging 972 reflects detected signals for CD8 surface marker detection. A portion of cells 106 in the imaging 972 exhibit sufficient signals to identify the presence of the CD8 marker. In imaging 974, an exemplary light field image of the same sample retention regions 124 indicate the presence the cells present in imaging 972 and other cells 106. Comparing, overlaying, or merging of the signals associated with the two imagings 972, 974 as depicted by composite imaging 978 can be accomplished using alignment markers and processes similar to those previously described.

Similarly, imaging 976 reflects detected signals for CD3 surface marker detection. A portion of cells 106 in the imaging 976 exhibit sufficient signals to identify the presence of the CD8 marker. Comparing, overlaying, or merging of the signals associated with the two imagings 972, 976 as depicted by composite imaging 980 can be accomplished using alignment markers and processes similar to those previously described. The composite imagings 978 and 980 can be further compared or overlaid to provide a final imaging that combines the data and signal information from each of the previous panels. Taken together, cell position as well as detected cell surface markers 985 may be determined. The presence of differentially detected markers (CD8, CD3) indicate differing characteristics and/or expression patterns for the cells. This information can further be used to classify or group the cells and discriminate between different cell types and/or states. Such classifications and groupings may be further considered in relation to respective detected analyte patterns 142 discussed below.

Figure 10A:
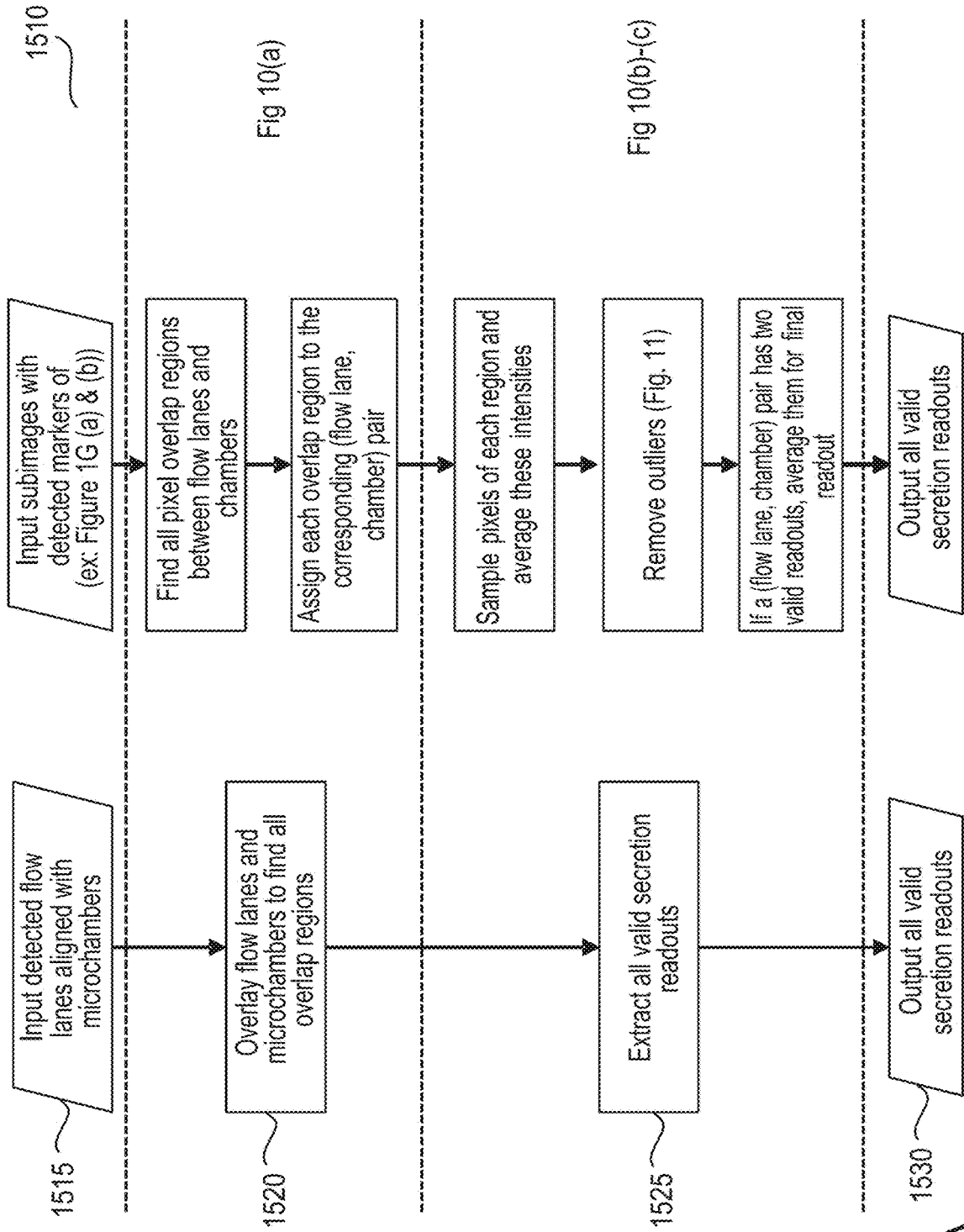
FIG. 10A depicts an exemplary process for merging sample retention region images/analyte scans according to the present disclosure.
Figure 10B:
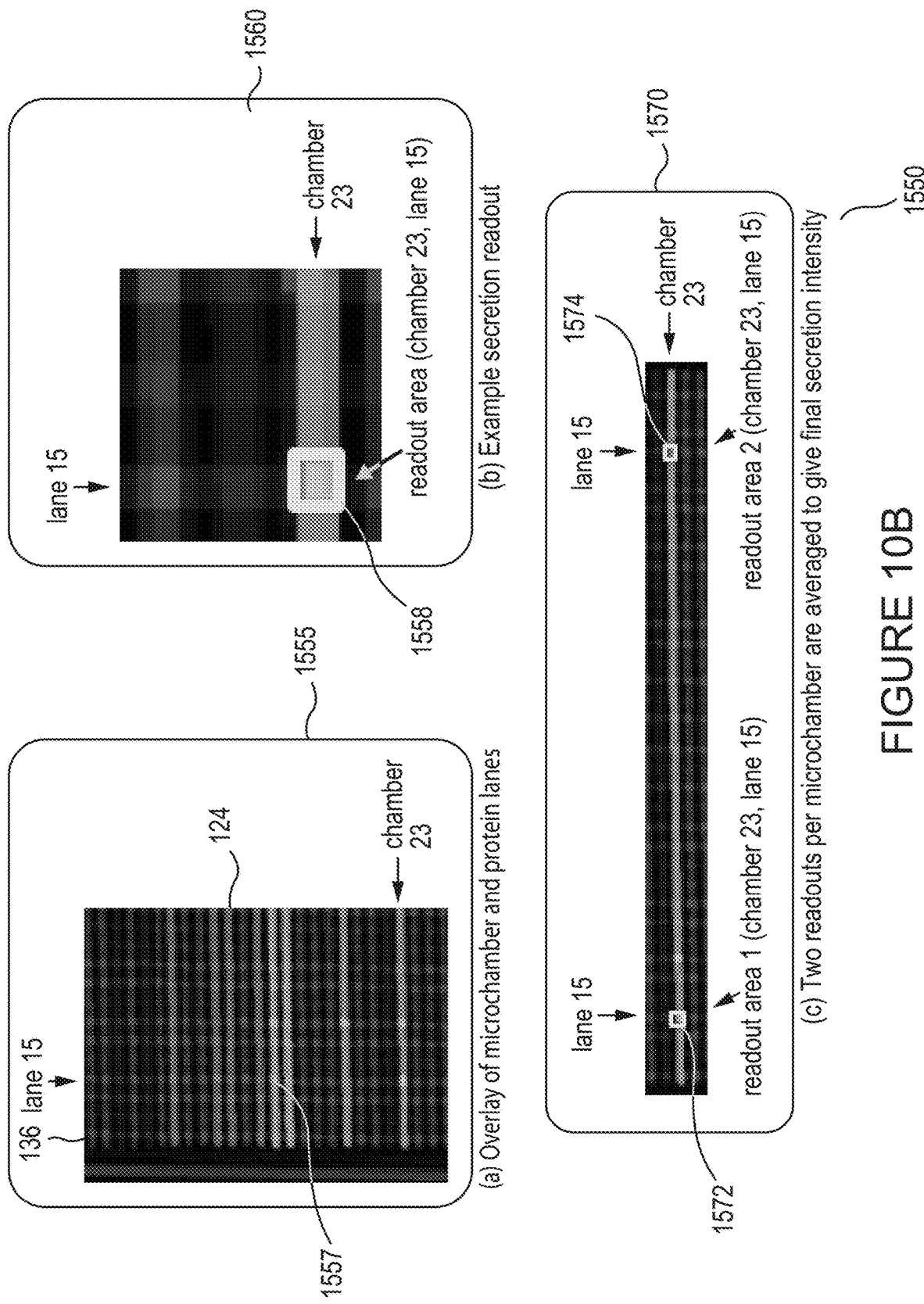
FIG. 10B illustrates exemplary imaging and pixel comparison processes according to the present disclosure.

Referring again to FIG. 1D, following positioning and alignment operations for the various images and scans associated with sample retention regions 124 of the sample array 122 and the analyte detection regions 136 of the analyte detection substrate 134, the analysis workflow 1000 may proceed with locating and identifying analyte patterns 142 associated with or attributable to selected cells/particulates 106 (step 1430). FIG. 10A provides details of a workflow 1510 for secretion readout determination. Additional secretion readout illustrations are provided in FIG. 10B.

In various embodiments, a selected analyte pattern 142 corresponding to one or more detected analytes 108 expressed, secreted, or released by the cell/particulate 106 comprise one or more discrete signals each associated with a respective analyte that are positioned about various known or expected locations with respect to the analyte detection substrate 134. The manner of fabricating, positioning and/or depositing the various analyte detection moieties 135/analyte detection regions 136 about the analyte detection substrate 134 determines the orientation and position of resultant detected analytes 108.

In various embodiments, two or more analytes may be detected in approximately the same position or region but observed in different scans. Positionally multiplexed analyte detection moieties 135 may thus be resolved from one another by the type of signal emitted and/or the scan or imaging in which they appear. (For example, co-located or positionally multiplexed analyte detection moieties may comprise discrete labels or fluorophores that may be separately detected and/or distinguished).

An analyte pattern 142 for a selected cell/particulate 106 may be identified or "read" by associating a selected sample retention region 124 with a corresponding series of one or more positions or regions 136 on the analyte detection substrate 134 where analyte detection moieties 135 are located. The disposition of the respective cell/particulate 106 that results in detected analytes 108 may therefore be determined by evaluating one or more selected pixel area(s) or regions for the cell images and the analyte detection scans where overlap occurs in a manner described in greater detail below. Signal intensity values identified in the representative signal/scan images may be mapped to discrete pixels and/or assigned numerical values representative of pixels in the imaging area for ease of identification and processing. In various embodiments, identified signal intensities of a selected threshold may be averaged to obtain a value that may be associated with the detected analyte 108. In various embodiments, higher accuracy quantification of analytes 108 and/or confirmation of the presence of selected analytes 108 may be determined using two or more regions of analyte detection/pixel analysis. Scans/imagings for these regions provide discrete overlap in two or more areas or locations between the sample retention regions 124 and the analyte detection regions 136. In various embodiments, the observed intensity values for each corresponding region of overlap may be compared and/or averaged to yield a higher confidence identification of respective detected analytes 108.

As shown in FIG. 10A, the analysis process 1510 may commence with acquiring detected flow lanes or analyte detection regions 136 that have been aligned with corresponding microchamber or sample retention regions 124. In various embodiments, sub-images corresponding to detected analytes 108 may be utilized to identify regions of intensity where one or more analytes are detected (see for example FIG. 1G (a) and (b)). Corresponding flow lanes or sample retention regions 124 may then be used to overlay or merge the analyte scans to locate regions of overlap. As discussed above, overlap may be determined according to pixels in the various images and scans. Regions or areas of overlap may then be assigned to corresponding sample retention regions 124/analyte detection regions 136 in a pairwise manner.

For assigned areas or regions of identified overlap the associated intensity data or signal information may be extracted from each position (step 1525). Associated or corresponding signals from selected areas may further be averaged to provide an output signal or readout that corresponds to the detected analyte 108. In certain instances, low confidence or outlier data or signals may be removed or flagged as described in greater detail with respect to FIG. 11 below. Duplicate or redundant signal intensities associated with the same cell/particulate 106 and analyte 108 pairings may further be compared and/or averaged for validity and/or confidence before generating a final analyte readout of the detected analyte 108. Thereafter, valid detected analytes 108, associated intensities, and other characteristics may be output (step 1530).

Figure 3:
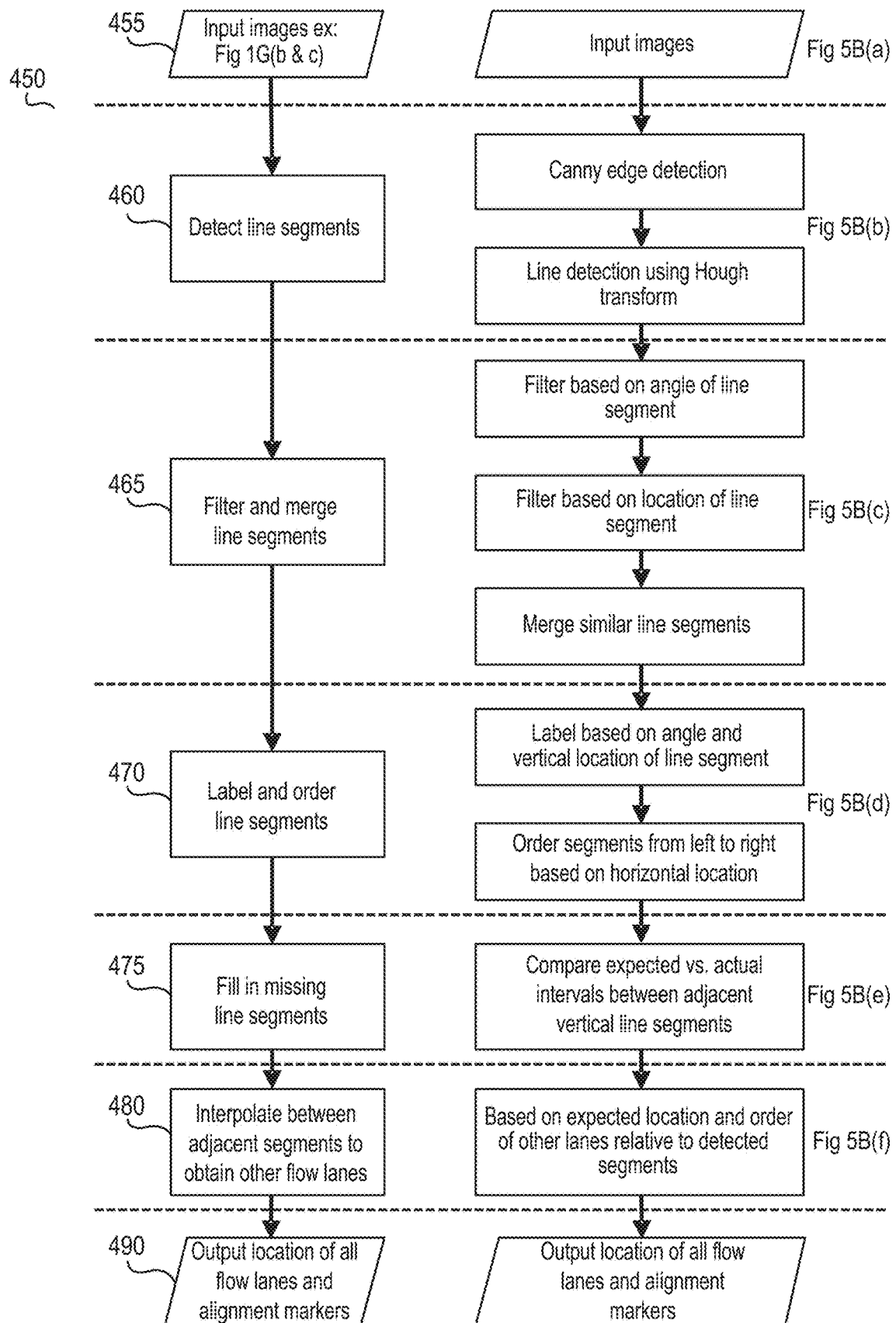
FIG. 3 depicts an exemplary method for location of alignment features according to the present disclosure.

FIG. 10E3 illustrates an example 1550 of the imaging and pixel comparison processes described in FIG. 10A. As shown in sub-image 1555, a plurality of analyte detection regions 136 (identified as "protein lanes") may be overlapping with a plurality of sample retention regions 124 (identified as "chambers"). According to the exemplary sub-image 1555, analyte detection regions 136 are generally vertically disposed overlaid or oriented with generally horizontally disposed sample retention regions 124. Overlapping regions 1557 with observable signal intensities are further identified. Sub-image 1560 provides a magnified view of a selected overlap region between analyte "lane" 15 and sample "chamber" 23. As depicted by the overlap region 1558, an analyte readout area may be designated indicative of the presence of a detected analyte 108. Sub-image 1570 further illustrates pairwise readouts for two distinct overlap regions 1572, 1574 corresponding to identical cell/particulate 106 and detected analyte 108 regions. These regions may be evaluated independently and the results compared and/or averaged as described above.

Figures 1, 10C:
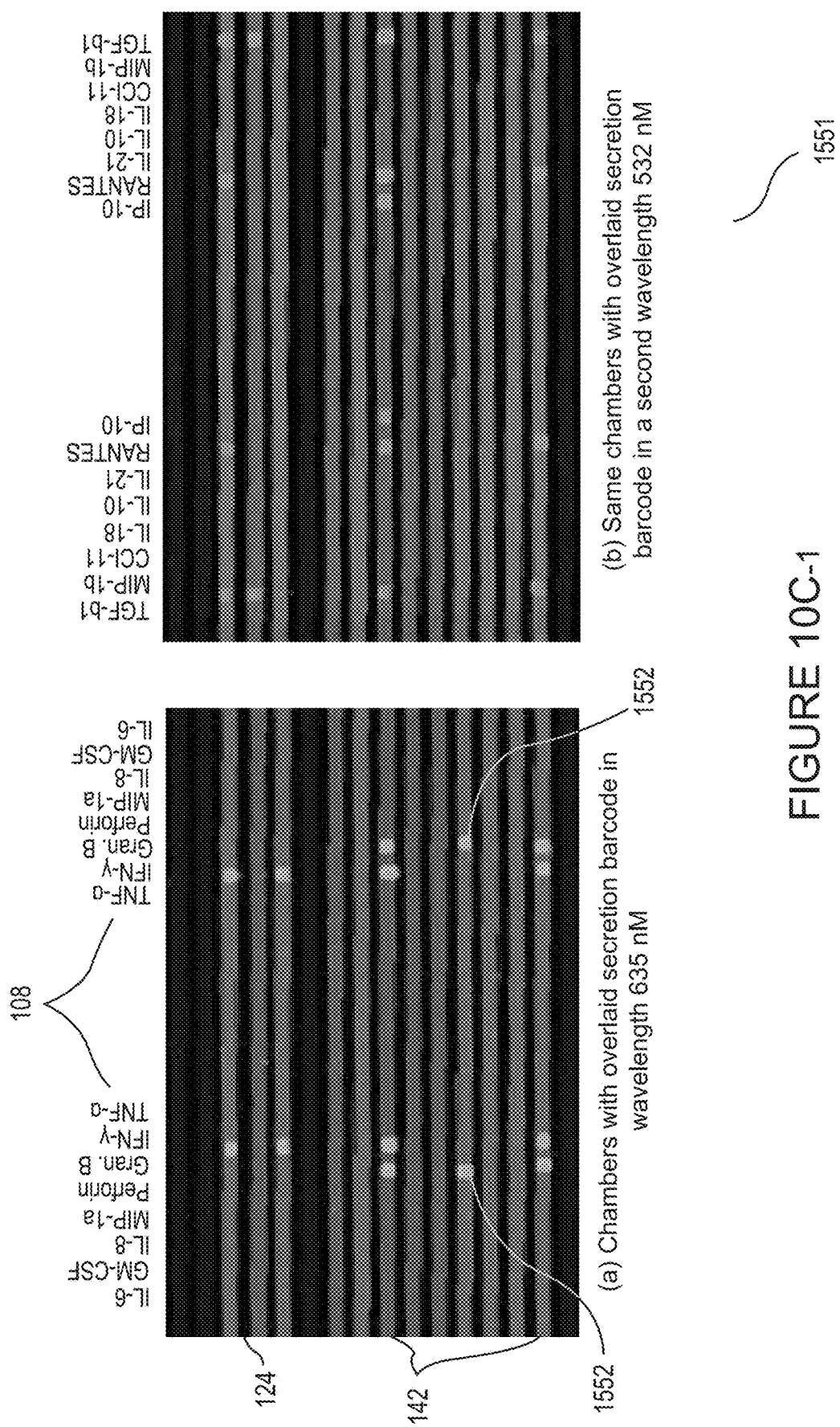
Figures 2, 10C:
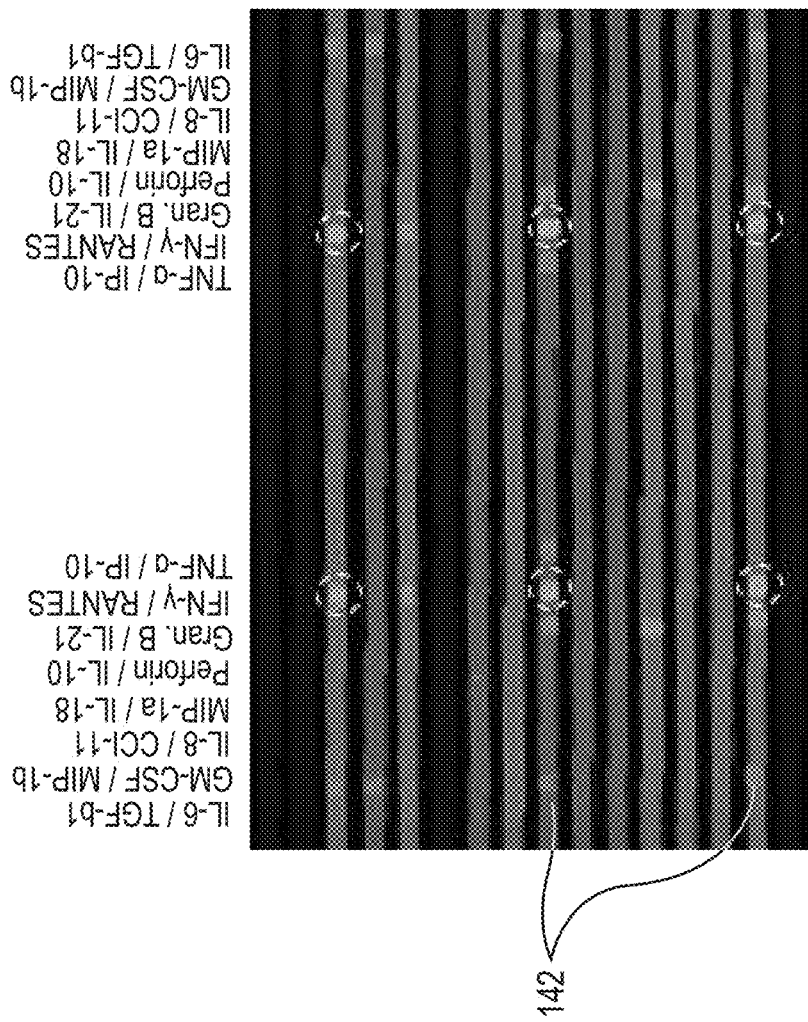

FIG. 10C illustrates a further example 1551 of the imaging and pixel comparison processes described in FIG. 10E3 above showing pairwise readouts 1552 associated with marker patterns 142 for exemplary sample retention regions 124. A plurality of analytes (e.g. cytokines) 108 may be discretely detected simultaneously and resolved from the marker patterns 142. As depicted in image panels (a) and (b), a plurality of images may be acquired using, for example, different wavelengths or with differing image acquisition characteristics to discretely identify markers 135 that may be co-located or positioned about the same analyte detection region 135. Images acquired with differing image acquisition characteristics may further be overlaid or merged as shown in panel (c).

Figure 11:
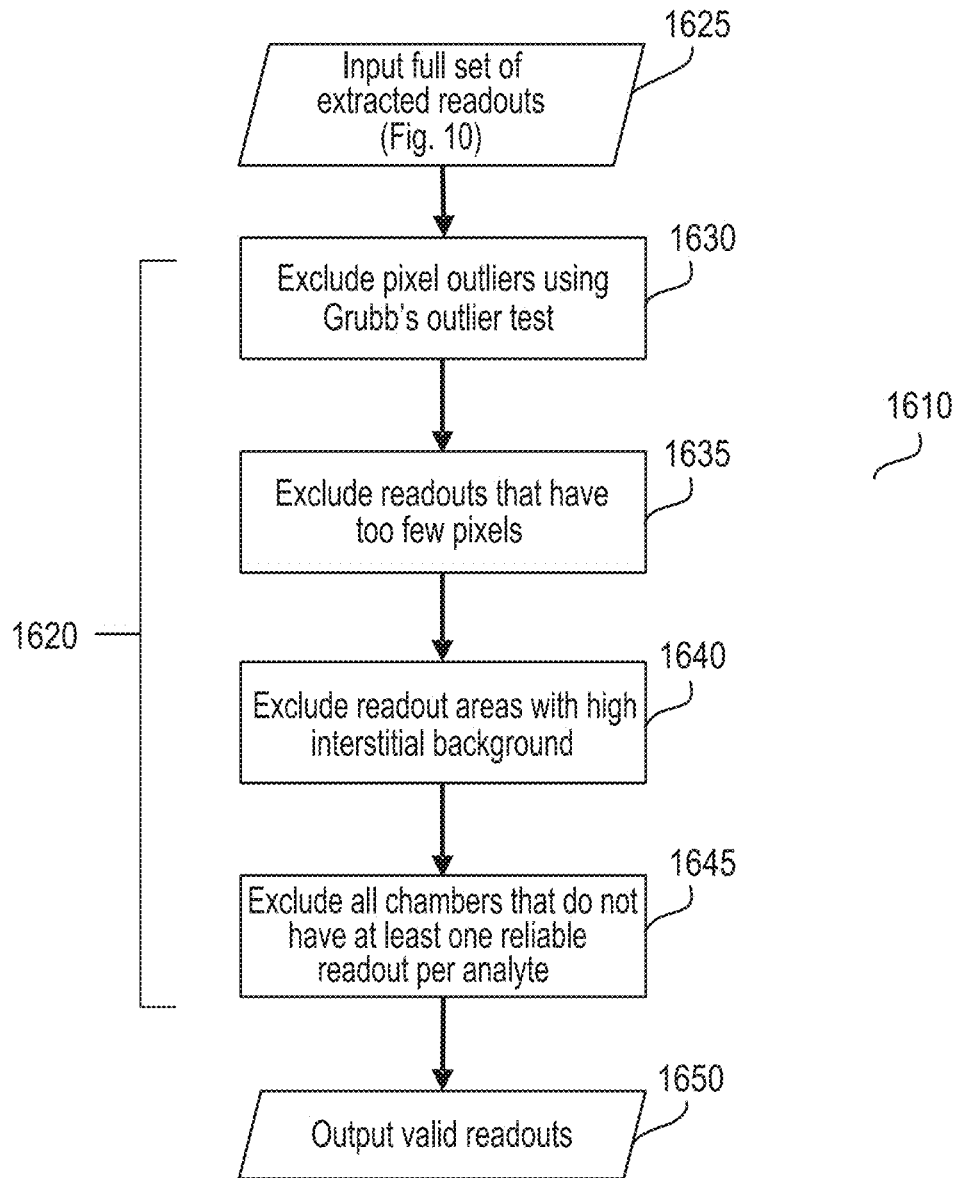
FIG. 11 depicts an exemplary process for gating outlier data and signals according to the present disclosure.

Referring again to FIG. 1D, following analyte/secretion location identification and analysis, a background signal evaluation and outlier detection analysis may be conducted (step 1440). FIG. 11 depicts a process 1610 for gating, excluding, and/or flagging potentially low confidence, error-prone or outlier data and signals. As discussed above in connection with FIG. 10, various scans or images (or portions thereof) may be subject to regions of high background and noise as well as other potential artifacts that may diminish the quality of signal data and results output by the analysis method 1000. To help avoid outputting erroneous and low quality results from the analysis, various quality checks or gating procedures 1620 may be applied to the output analyte identifications, readouts, and associated image/scan data obtained from step 1530. This data may be first received for quality review (step 1625) where one or more quality checks 1620 are applied.

One exemplary quality test 1630 may comprise an assessment of image/scan quality based on pixel information. A Grubb's test may be performed to exclude or flag pixels in the images/scans that are identified as potential outliers. In various embodiments, pixel data corresponding to images/scans for portions of the sample retention regions 124 overlapping with the analyte detection regions 136 (exemplified in FIG. 10B) may be considered as well as other regions of pixel data. Pixel data failing the Grubb's test may serve as an indicator that associated image/scan data in these regions are suspect and results/readouts may be excluded or flagged for further review.

Another exemplary quality test 1635 may comprise evaluating pixel areas or sizes of regions where intensity information was extracted and evaluated. Size thresholds may be applied to the image/scan data and analyte results/readouts associated with pixel areas that fall below or do not meet the selected threshold excluded or flagged for further review. As one example, insufficient overlap between an analyte detection region 136 and an associated sample retention region 124 may result in insufficient pixel information to accurately determine or assess the data. In regions with insufficient overlap as determined by preselected criteria the results/readouts may be excluded or flagged for further review.

A further exemplary quality test 1640 may comprise evaluating image/scan data to identify regions of high interstitial background. In various embodiments, evaluation of images/scans in areas substantially adjacent or proximal to identified analyte detection regions 136 and/or sample retention regions 124 (for example, above, below, to the right, or to the left) may indicate one or more of the interstitial regions exceed a threshold associated with the analyte signals. Such a result may suggest the associated data/readout is indicative of a false positive result. Consequently, such results/readouts may be excluded or flagged for further review.

Another exemplary quality test 1645 may consider observed analyte results associated with selected sample detection chambers 124. In various embodiments, sample retention chambers that are not associated with at least one reliable analyte identification/readout for selected analytes may be excluded or flagged for further review. In some instances, at least one reliable readout should be obtained from two or more associated analyte imaging areas.

Following application of one or more of the various gating and quality assessment checks described above, the resulting analyte data/readouts may be considered valid and output (step 1650). It will be appreciated that applying various quality assessments desirably improve the overall confidence and quality of the data analysis. Additional quality assessments may thus be applied to further enhance the output analyte data/readout quality.

Figure 12A:
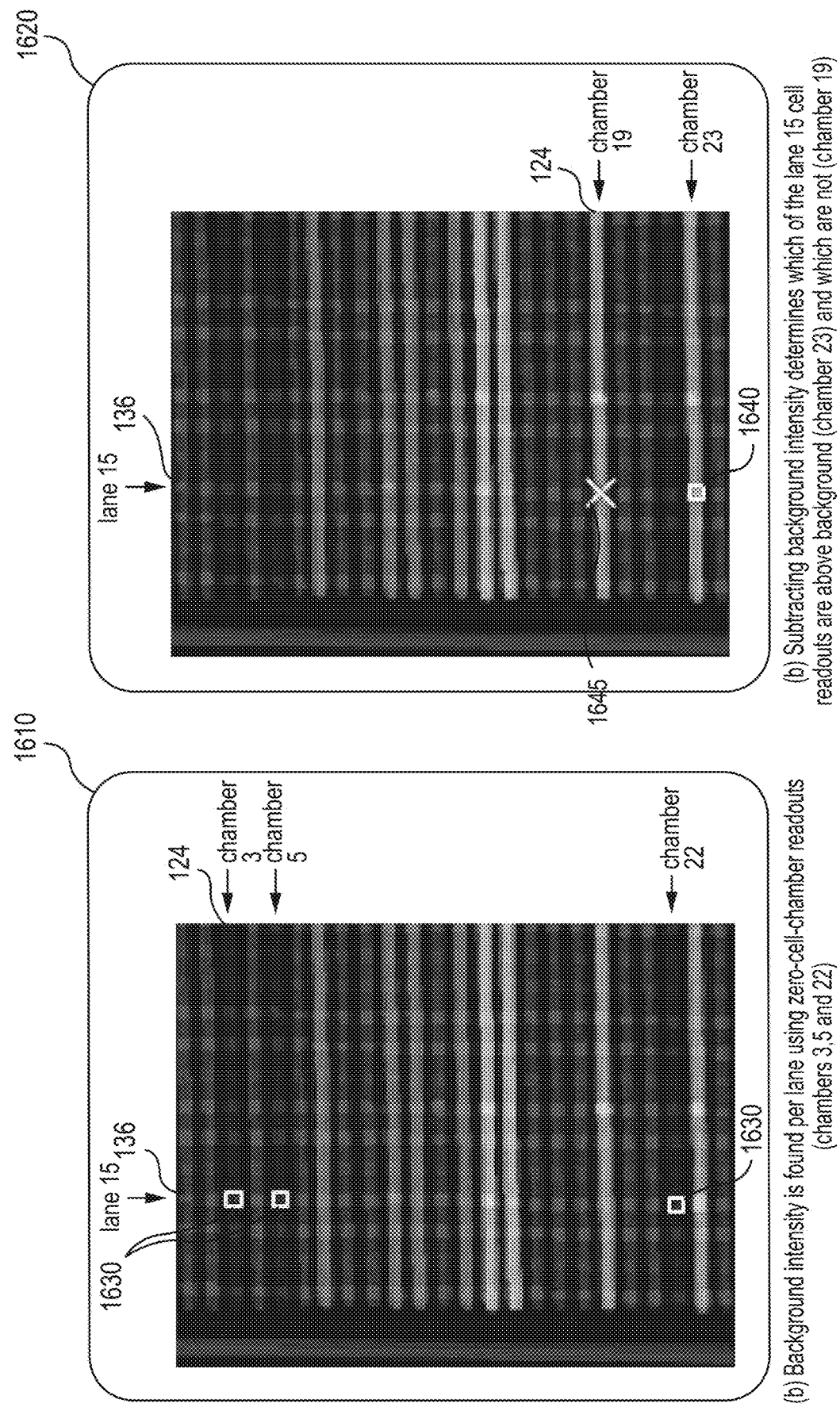
FIG. 12A illustrates exemplary images of a portion of a sample retention region with intersecting analyte detection regions according to the present disclosure.

Referring again to FIG. 1D, following exclusion of high background signals and associated analyte data, data analysis 1000 may proceed with quantification of signals for analytes 108 detected in one or more analyte detection regions 136 (step 1450). FIG. 12A illustrates exemplary imagings 1610, 1620 depicting a portion of selected sample retention regions 124 with intersecting analyte detection regions 136. Shown in image panel 1610, sample retention regions 124 (identified as "zero-cell-chambers" chambers 3, 5, 22) that have previously been determined to lack a cell/particulate 106 contained or residing therein are identified. Signal intensities in the regions associated with the various intersecting analyte detection regions 136 (e.g. lane 15) may be leveraged to determine or characterize background signal intensities.

For example, the signal intensities associated with one or more of the sample analyte regions lacking a cell/particulate 106 may be evaluated in the selected intersection regions 1630 to determine an associated background signal. In various embodiments, background signals may be determined for one or more analyte detection regions 136 and/or for one or more sample retention region 124. Background results may be further processed by combining, averaging, or other methods to determine an overall background signal value to be applied to other signal intensity data or applied individually to selected or corresponding signal intensity data for sample retention regions 124 located in proximity to a region 1630 where a background signal was determined.

As shown in image panel 1620, background signal intensities may then be applied to the signal intensity data associated detected analytes 108 for sample retention regions 124 that have been previously identified as containing at least one cell/particulate 106 (ex: chambers 19, 23). In various embodiments, background signal intensities may be used to evaluate the analyte signals/readouts associated with selected analyte detection regions 136 to further characterize the resultant detected analyte signals. For example, as shown in image panel 1620, signal intensities for a selected analyte detection region 136 (e.g. lane 15) may be evaluated for respective sample retention regions 124 (e.g. chambers 19, 23) and characterized with respect to background. For example, subtraction of background signal from associated signal intensities may be performed and corresponding regions characterized as above-background (ex: 1640) or below-background (ex: 1645). Background analysis in this manner may further be used to qualify the presence or absence of analyte 108 corresponding to the background-subtracted regions.

Figure 12B:
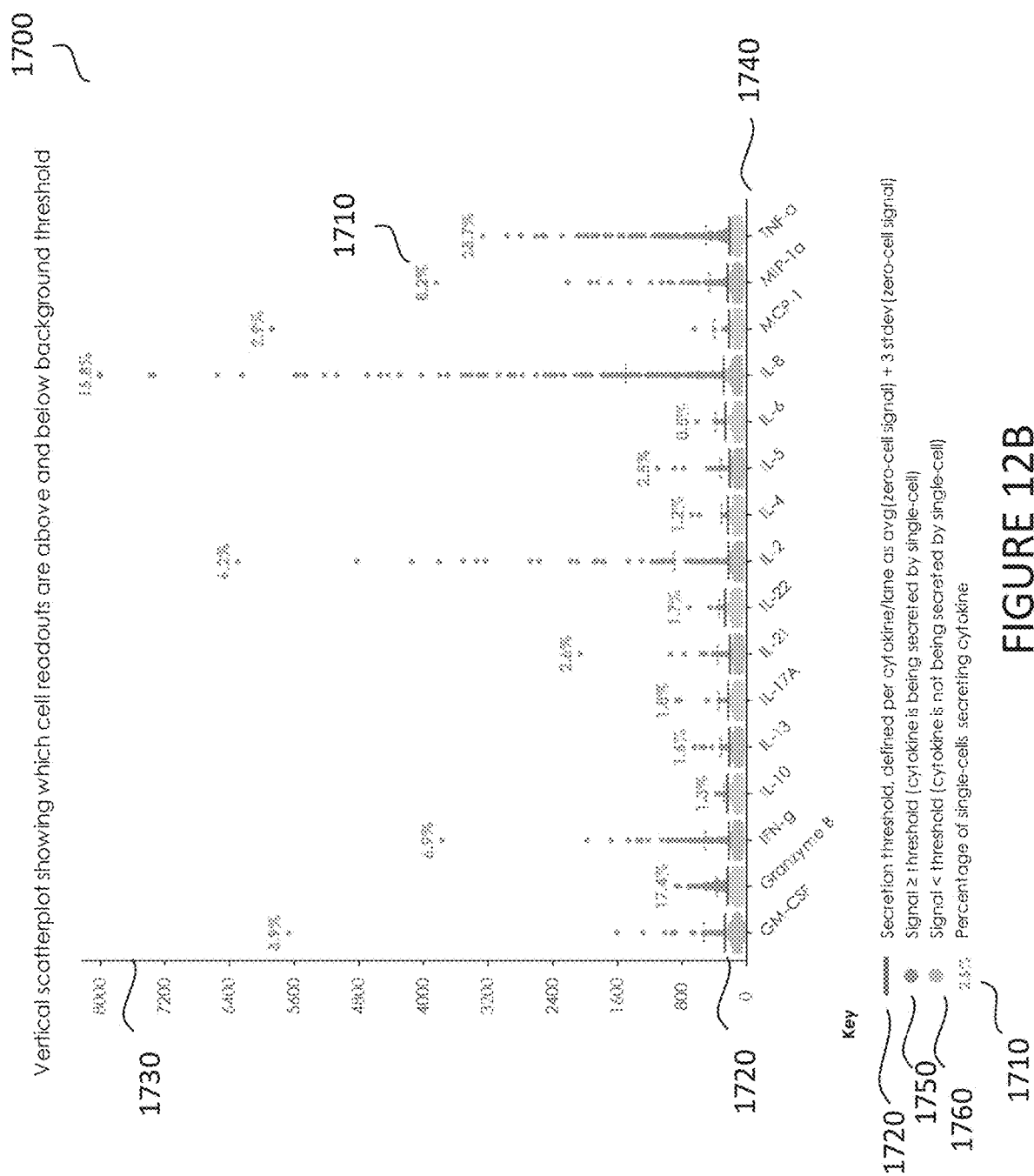
FIG. 12B depicts an exemplary scatterplot for evaluating a plurality of analytes according to the present disclosure.

FIG. 12B depicts an exemplary scatterplot 1700 for an experiment in which a plurality of samples (e.g. cells 106) are evaluated for a plurality of analytes (e.g. cytokines 108). Analysis results are shown as a number or percentage 1710 of cells exhibiting analyte signals/readouts with respect to a background signal or background threshold 1720. The vertical axis 1730 provides relative intensity values or units for selected cytokines depicted on the horizontal axis 1740. Background thresholds 1720 are determined for each cytokine independently and cells characterized by the detected presence of an analyte above-threshold 1750 or below-threshold 1760.

Analyte secretion or detection results depicted in the above-indicated manner provide a convenient method to evaluate overall expression, secretion, or presence of selected analytes for a potentially large number of cells simultaneously. Using this information, cells may be evaluated for analyte presence and/or response on a single cell basis while allowing potentially large populations of cells to be collectively profiled to reveal insights regarding the behaviors, responses, or characteristics of the cells. Applying the disclosed analysis methods therefore provides a practical means by which to assess for multiple analytes including biochemicals, cytokines, and chemokines secreted from the same cell across significant numbers of cells simultaneously while maintaining sensitivity and accuracy to detect analyte secretions for single cells or cell-cell interactions.

Figure 12C:
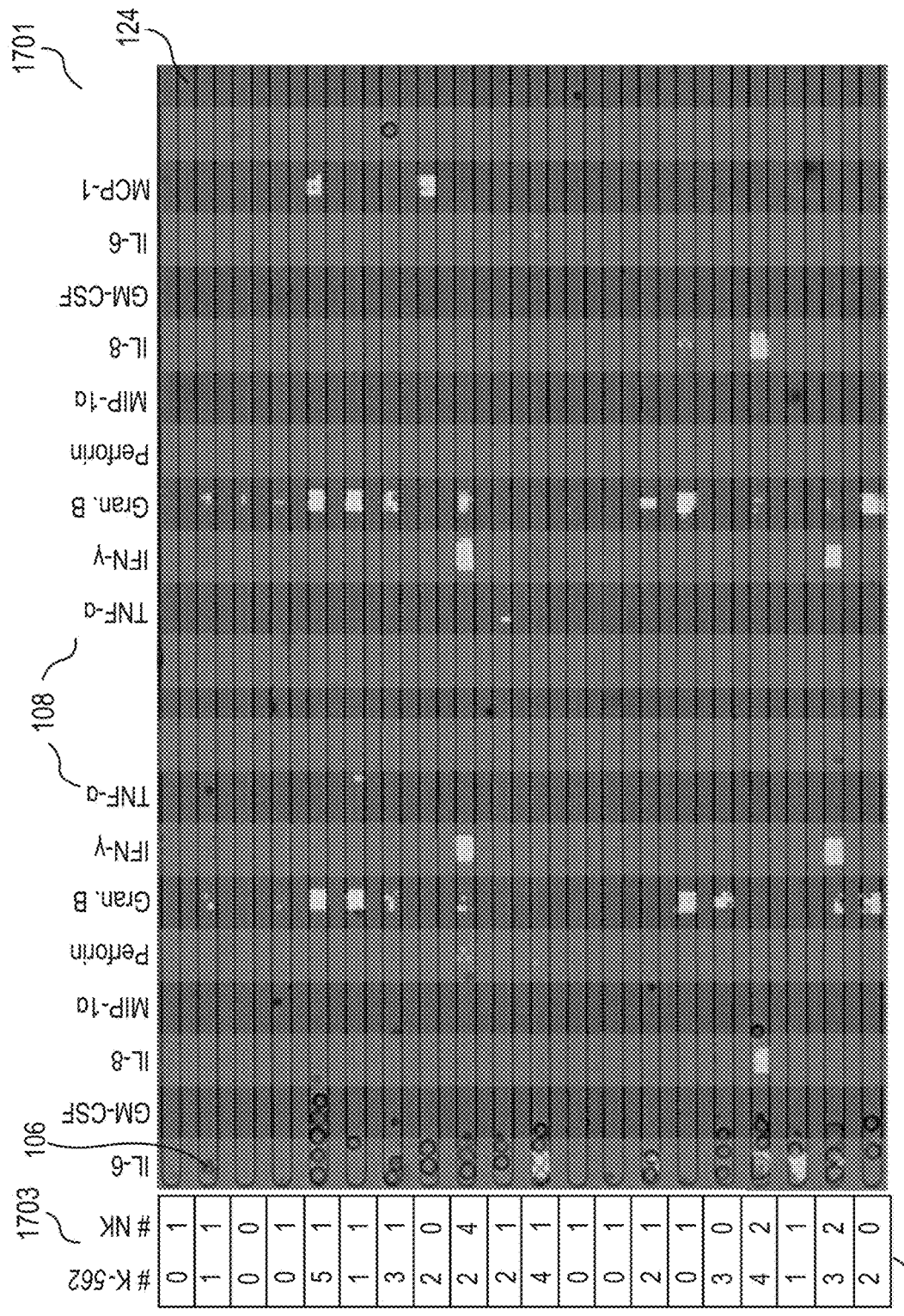
FIG. 12C illustrates exemplary imaging results for marker patterns/readouts from detected analytes associated with two cells cell types according to the present disclosure.

FIG. 12C illustrates exemplary imaging results 1701 for merged images of a selected subset of sample retention regions 124 with associated marker patterns/readouts resulting from detected analytes 108 associated with one or more cells 106 contained within the sample retention regions 124. Pairwise analyte analysis results are shown as described previously and further associated with a cell number 1702 and cell type 1703. Evaluating detected analyte results from respective sample retention regions 124 containing singular cell types 1703 (e.g. K-562 and NK cells) versus analyte results for sample retention regions 124 containing two or more cells of different types can provide, for example, information and insights into cell-cell interactions and associated changes in cellular analyte response or cellular secretions. Additionally, evaluating analyte results for sample retention regions 124 containing two or more cells of the same type can provide, for example, information and insights into cell-cell interactions and further be used for quantitative analyte analysis correlated with the number of cells present in the chamber.

Figure 13A:
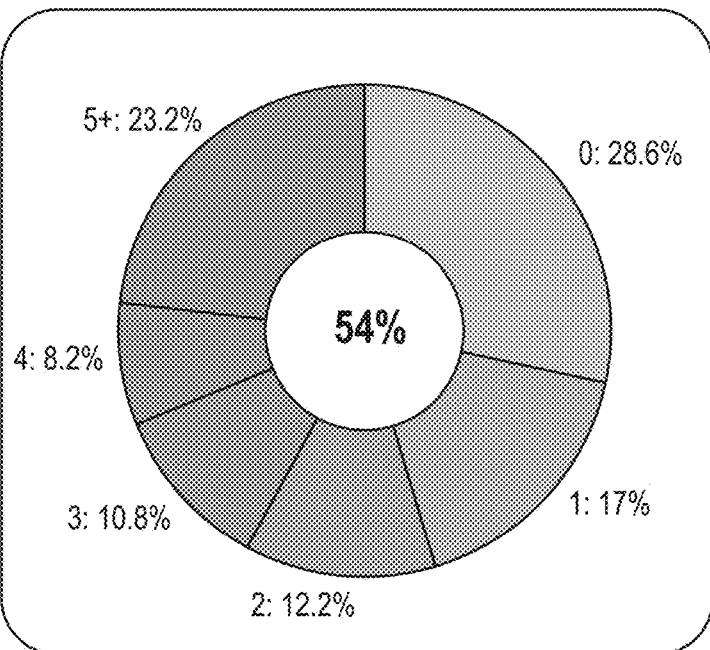
FIG. 13A depicts exemplary methods and tools for presenting and interpreting analyte data and results according to the present disclosure.
Figure 13A:
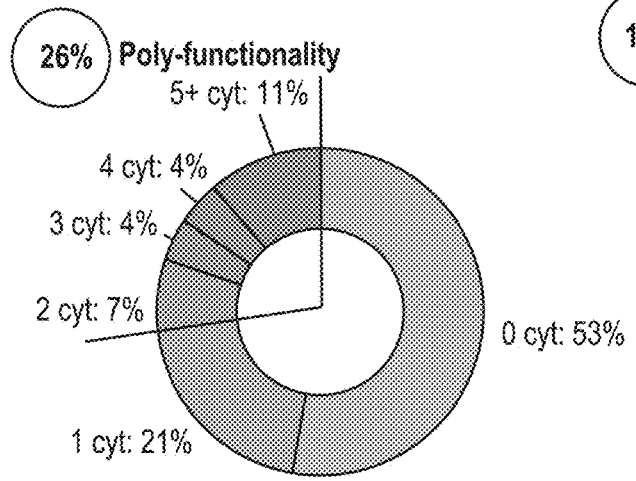
Figure 13A:
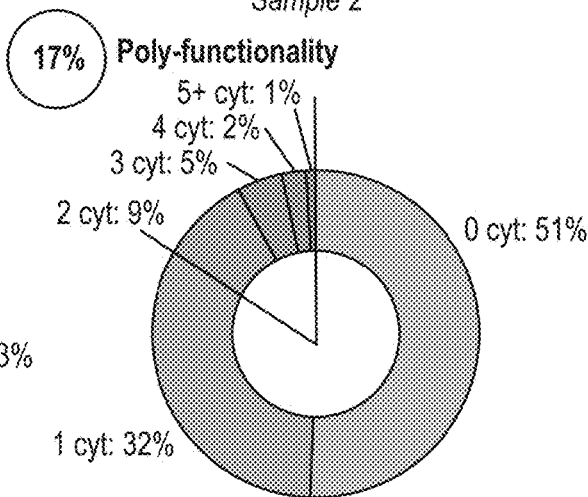
Figure 13B:
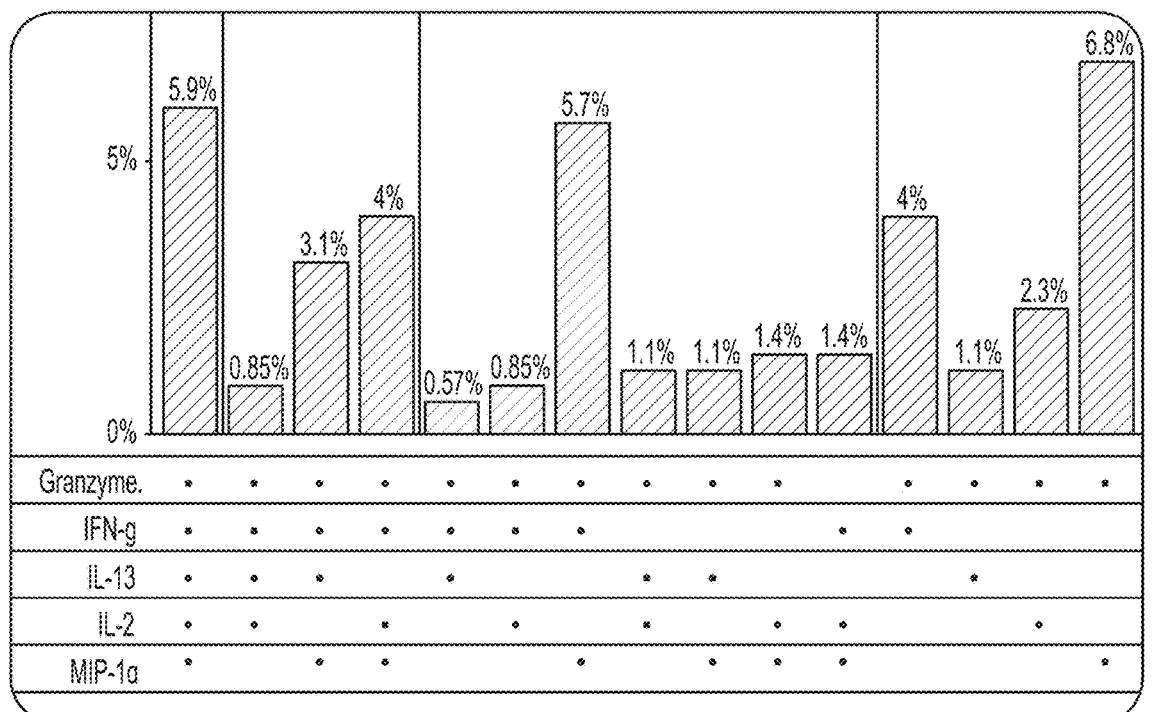
FIG. 13B depicts exemplary methods and tools for presenting and interpreting analyte data and results according to the present disclosure.
Figure 13B:
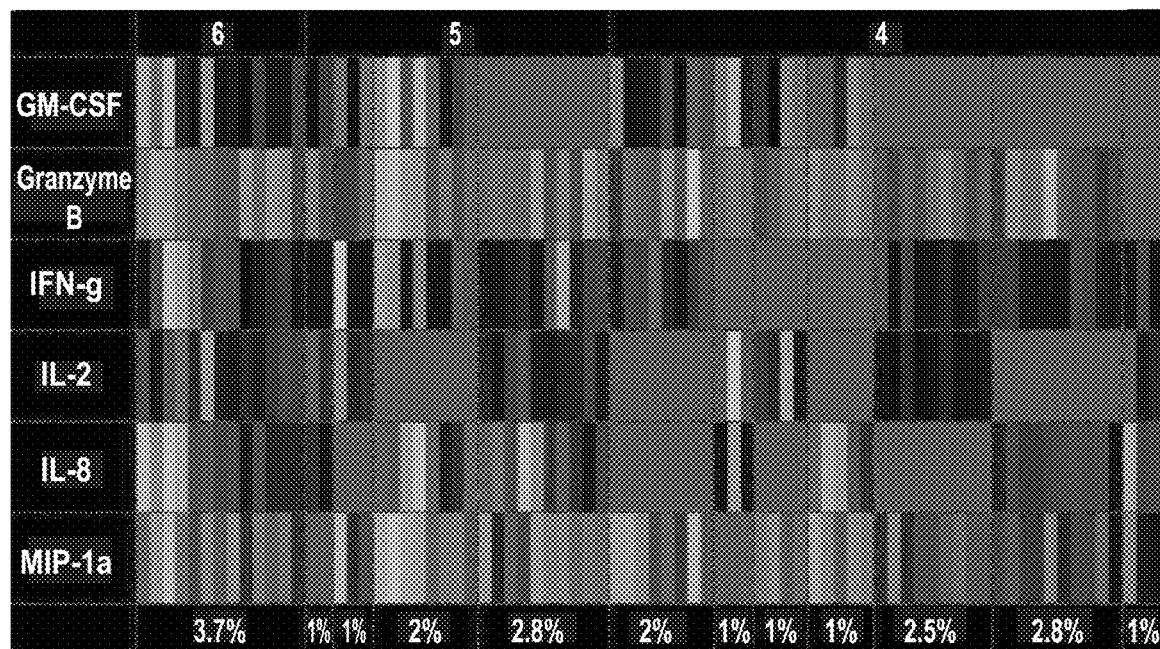

Referring again to FIG. 1D, the data analysis 1000 may include additional operations and tools for evaluation of populations of discrete cells to determine correlative analyte (e.g. cytokine/chemokine) response and functional profiling of samples (step 1460). In various embodiments, experimental data and results obtained according to the disclosed methods may be further analyzed, compared, and associated providing powerful tools for discovery, screening, surveying many different types of cellular characteristics, responses, and functionalities, such as those implicated and correlated with immune response. As shown in FIG. 13A and FIG. 13B, various methods and tools 1800 for presenting and interpreting analyte data and results may be utilized. For example, in single cell experiments, evaluation of polyfunctionality across a population of cells may be provided as output from the data analysis. Single cell expression data and information obtained from one or more experiments may be related to identify patterns and trends in polyfunctional expression (e.g. the ability to secrete multiple effector proteins/cytokines from the same cell). Secretion profiles corresponding to an exemplary polyfunctional assay for selected cytokines is depicted in exemplary pie charts 1805, bar graphs 1810, and heat maps 1815. Additional correlations may be made, for example, comparing cell types from multiple samples and comparing detected analytes to known or established parameters to determine analyte expression or secretion profiles, physiological correlations, disease states, and/or treatment response.

Figure 14A:
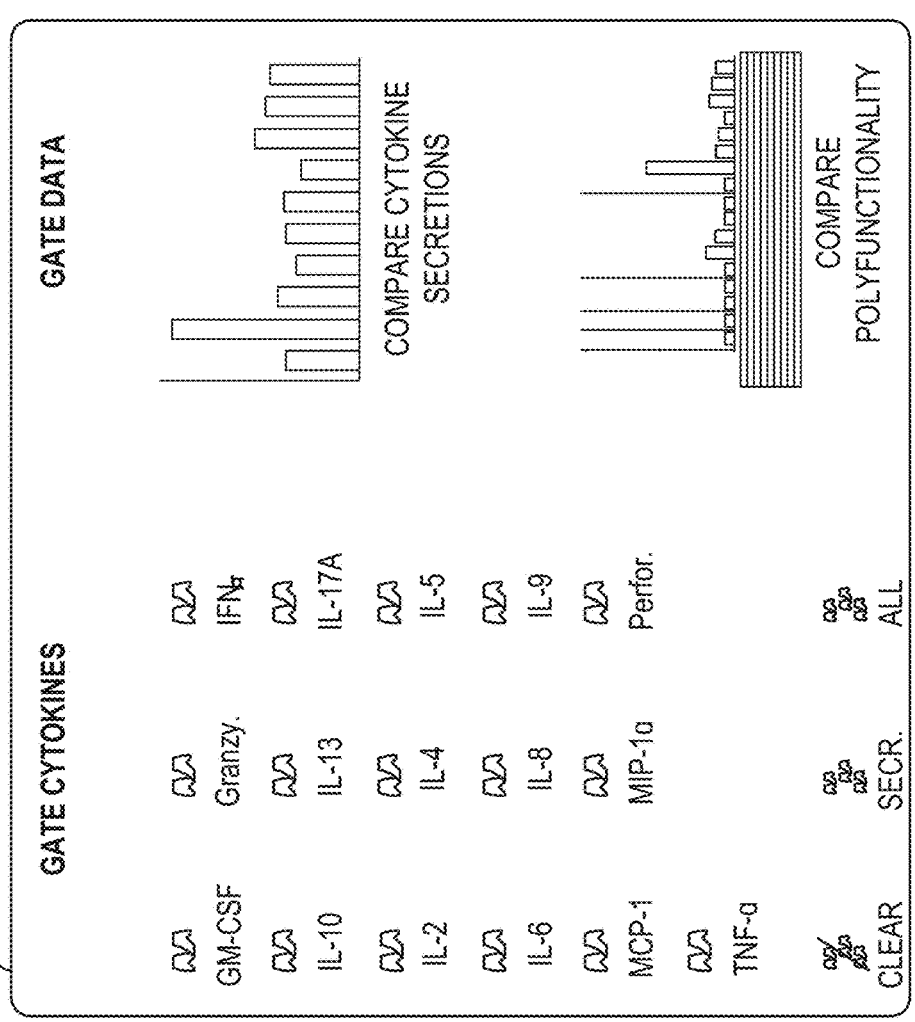
FIG. 14A depicts an exemplary database interface for evaluating experimental results according to the present disclosure.

Referring again to FIG. 1D, the data analysis 1000 may include additional operations and tools to facilitate comparison and/or correlation of experimental analyte response results with other information, for example, by comparison with a database of existing literature/publications/datasets (step 1470). FIG. 14A depicts a database interface 1850 containing information that may be used to evaluate single cell experimental results providing a tool for inference determination and discovery.

The database 1850 for example may comprise single cell secretion/analyte expression information from previous experiments as well as literature/published data. Exemplary experiment filters 1855, publication filters 1860, and data filters 1865 provide users with the ability to focus on desired or relevant information which may be used to query stored experimental data and publication information. The experimental filters 1855, for example, may allow selection or retrieval of data/information based on particular or selected informational sources, diseases/conditions, subject types, cell types and/or technologies (used for sample analysis, such as flow cytometry, Enzyme-Linked ImmunoSpot (ELISPOT), the presently described technology, etc.). The publications filters 1860, for example, may allow selection or retrieval of relevant literature/information based on particular or selected areas of interest, scientific categories, authors, publication year, and/or keywords. The data filter 1865, for example, may allow selection of data/information/literature based on particular or selected cytokines or other analytes of interest. The data filter 1865 may further provide functionality for data retrieval based comparisons between cytokine/analyte secretion profiles or values as well as selections based on polyfunctional cytokine/analyte response. Various metrics can be chosen to automatically compare the similarity of the overall cytokine/analyte secretion and/or polyfunctional profiles. To further facilitate user interaction with the database tool, various filters may be auto-populated with search and data selection criteria. In conjunction with any user-selected filters, an overall determination can be made as far as the relevance or similarity of a catalogued dataset with the user's current dataset. In various embodiments, where a conclusive correlation cannot be determined, providing a small set of relevant past experiments/datasets can help guide or aid a user in determining what subsequent tests may be informative to run, how a treatment could be performed relative to others, etc.

Figure 14B:
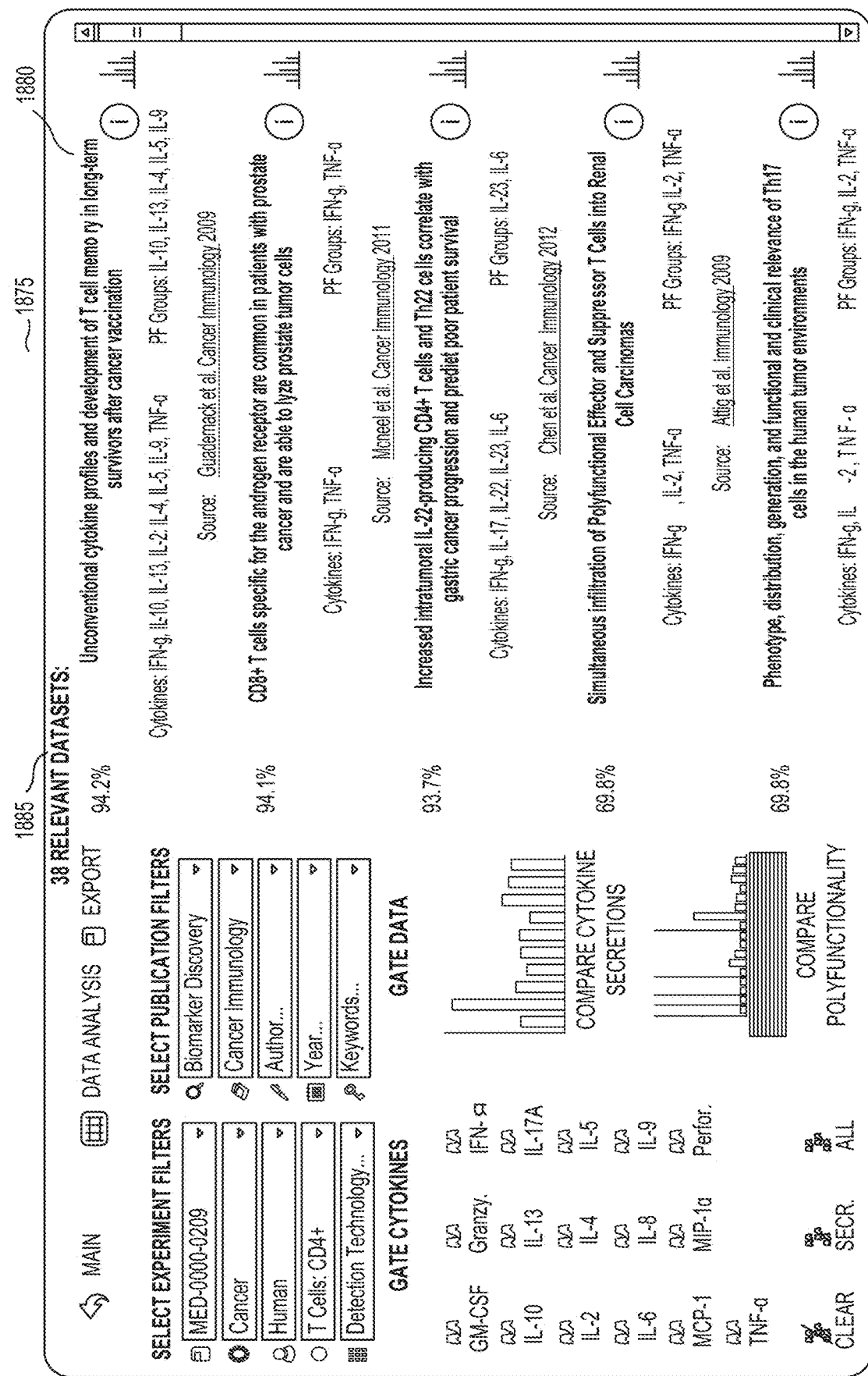
FIG. 14B depicts an exemplary results interface for displaying information from an experiment according to the present disclosure.

FIG. 14B depicts an exemplary results interface 1875 for displaying information from a selected single cell experiment. Results and relevant associated datasets 1880 may be selected and examined in more detail with convenient links to publications and associated data. A score or rank 1885 may further be attributed to the results 1880 based, for example, on their similarity to an experimental or desired cell profile providing details and correlations between the literature/publications with the obtained/experimental cellular response data.

Figure 14C:
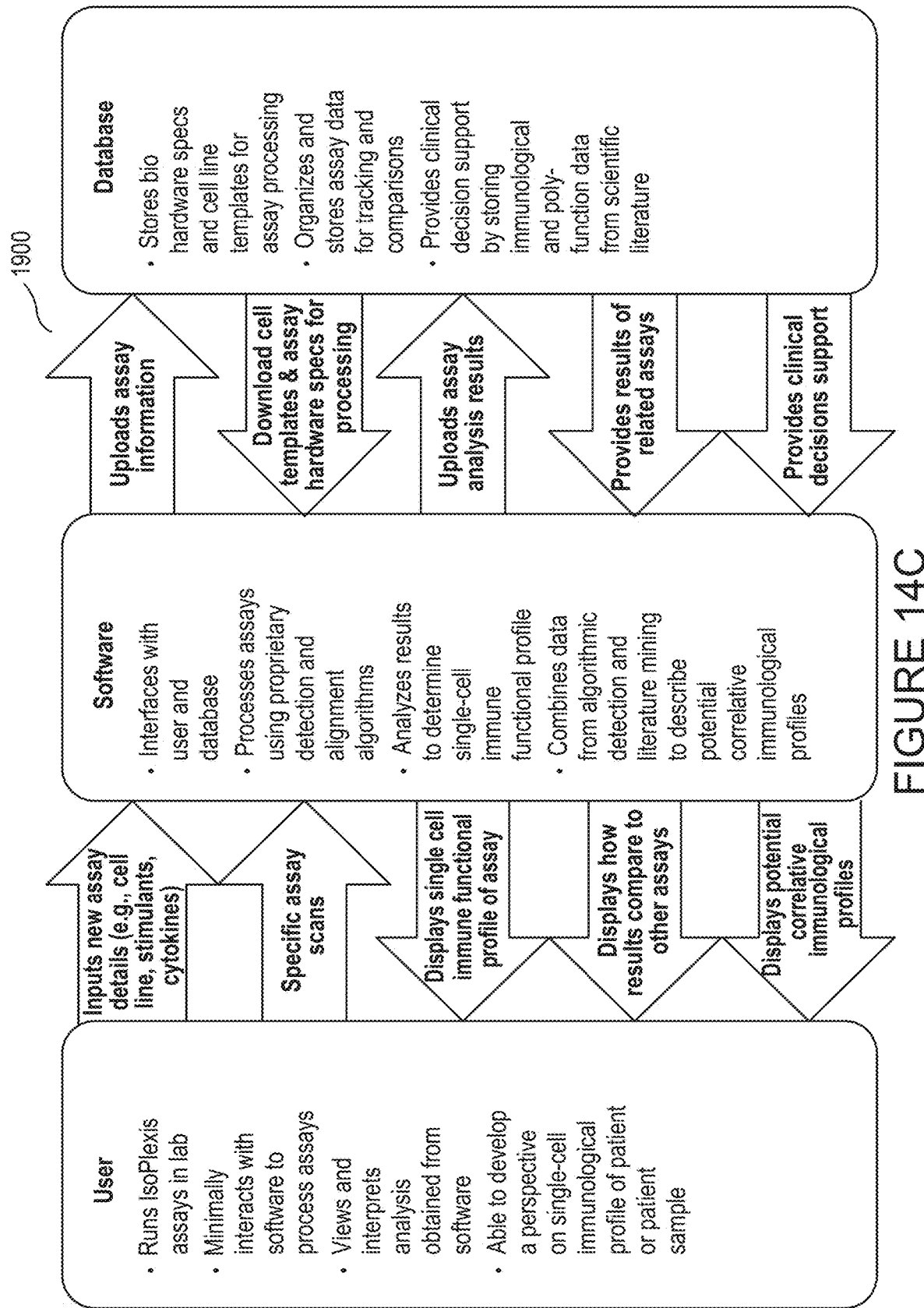
FIG. 14C depicts a workflow for analysis functionalities and database querying according to the present disclosure.

FIG. 14C depicts an overall workflow 1900 for the above-described data analysis functionalities and database to provide single-cell profiling capabilities in the context of immunological profiling analysis. Leveraging the throughput, sensitivity, and accuracy of the systems and methods disclosed herein enables functional characterization of single cells, populations of cells, and classes or types of cells providing additional data gathering, evidence evaluation, and inference determination functionalities to evaluate experimental results.

Figure 14D:
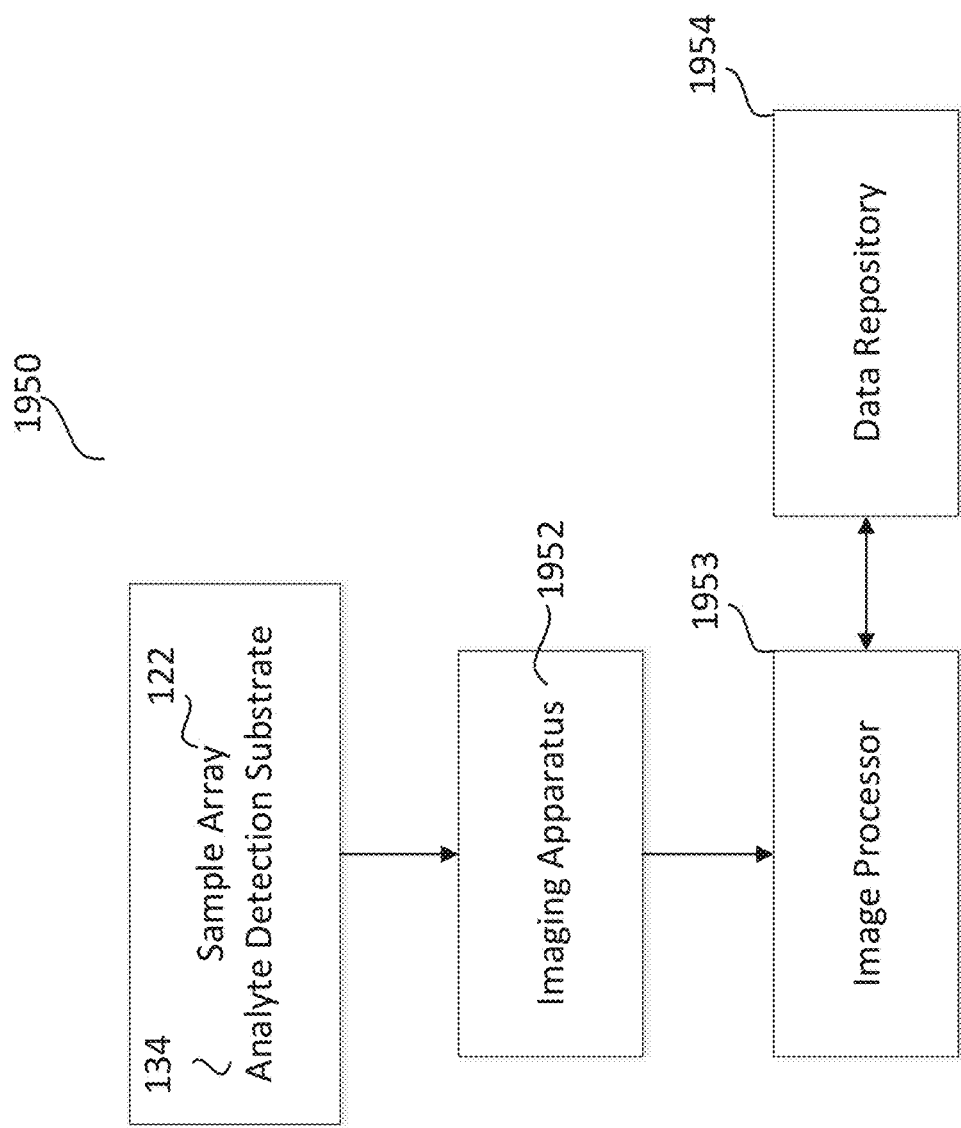
FIG. 14D depicts an exemplary platform comprising components for image acquisition and computational components for image analysis and subsequent analyte evaluation according to the present disclosure.

In various embodiments, and as shown in FIG. 14D the methods and processes described above and depicted in the associated figures may be implemented using a platform 1950 comprising components for image acquisition further comprising computational components for image analysis and subsequent analyte evaluation. The platform 1950 may further comprise an integrated system, for example, a singular device or instrument capable of performing each of the functions to output desired analyte results and associated data. Also, the platform 1950 may include discrete or separate components comprising various instruments and computing components for performing various desired functionalities.

In various embodiments, sample arrays 122 and associated analyte detection substrates 134 are processed by an imaging apparatus 1952 that acquires a plurality of images/scans. The imaging apparatus 1952 may include one or more imaging devices including by way of example microscopes, florescence detectors, microarray scanners, and/or other optical and signal detection apparatus. An image processor 1953 comprising, for example, a computing device with suitable image processing and data analysis software may be configured to receive signal information, images, scans, and other data associated with the imaging process. The image processor 1953 may further evaluate and analyze the information determine or associate analytes responsible for exhibited signals along with determining corresponding cell(s)/particulate(s) associated with the detected analytes.

The image processor 1953, for example, may determine correspondence between cytokine signals and detected single-cell chambers/microwells detected by the imaging apparatus 1952 and further associate the cytokine signals with one or more specific cells to generate a cell-by-cell profile of secreted proteins for individual cells. The image processor 1953 may further quantify detected analytes and associate this information with detected cells/particulates. The image processor 1953 may further perform additional analytics that associate detected analytes for the various detected cell(s)/particulate(s) across one or more analytes per cell/particulate. The image processor may further determine cell/particulate functional responses and characteristics and leverage information contained in one or more data repositories 1954 to perform further associations, determine outcome data and compare against existing information/literature as described above.

The imaging and analysis methods may be implemented using software comprising computer programs using standard programming techniques. Such programs may be executed on programmable computers each including an electronic processor, a data storage system (including memory and/or storage elements), at least one input device, and least one output device, such as a display or printer.

In some embodiments, the code is applied to obtaining and analyzing image and scan data (e.g., images and scans for sample retention regions 124, analyte detection regions 136, and associated cell(s)/particulate(s) 106 and analyte pattern(s) 142), to perform the functions described herein, and to generate output information (e.g., assessment/quantitation of analytes, polyfunctionality determinations, and associated correlations/inferences), which may be applied to one or more output devices. Each such computer program can be implemented in a high-level procedural or object-oriented programming language, or an assembly or machine language. Furthermore, the language can be a compiled or interpreted language. Each such computer program can be stored on a computer readable storage medium (e.g., CD ROM or magnetic diskette) that when read by a computer can cause the processor in the computer to perform the analysis described herein.

The speed, accuracy, and throughput capabilities of the system and methods of the present disclosure are useful for cell population analysis at the level of single cell assays and cell signaling assays between singular cells. In particular, the present teachings may be advantageously applied to cell population analysis to discriminate between highly polyfunctional classes of cells such as immunological cells (e.g. B-cells, T-cells, macrophages, and other immuno-cell types). Immuno-cells are associated with the secretion of many cytokines per cell and often exhibit significant differences between cytokine secretion profiles for individual cells. Applying the teachings disclosed herein, clinicians and researchers are able to analyze cell and protein secretion profiles in a sensitive and reproducible manner. Single cell cytokine secretion profiles (e.g. analyte readouts) may be analyzed for one or more patients or samples simultaneously and evaluated against databases of immuno-cell cytokine responses to evaluate immune functionality, regulation and toxicity. As previously described, the system provides a high degree of automation for processing of various cellular images, analyte detection scans, and querying databases of information to automate the single-cell functional analysis.

The composition of T-cell subpopulations (based for example on CD4/CD8 ratios) as well as their associated effector/cytokine secretion profiles may be correlative of clinical outcome and/or therapeutic response. Examples of where such analysis may useful include but are not limited to immune cell response for patients with human acquired immune deficiency syndrome (AIDS), as well as adaptive immune protection responses against pathogen infections.

In various instances, the same or similar cell type (e.g. for example CD4 or CD8 cells) may comprise highly heterogeneous populations with dynamic and evolving functional phenotypes. Such cells may be desirably classified at the single cell level by their immune effector functions (e.g. cytokine secretion profiles). Potency and durability of immune response can further be correlated with polyfunctionality and thus it is desirable to analyze multiple immune effector proteins from the same cell. In considering the nature of cytokine secretions, the degree of immune protection may be correlated with both the frequency of polyfunctional immune cells (for example T-cells) secreting distinct cytokines simultaneously, as well as the quality and/or amount of cytokine secretion.

Immune cells not only display distinctive and disparate immunological secretion profiles but also influence activity in the micro-environment where they reside. Cytokines such as the tumor-necrosis factor (TNF) are produced by immune cells, and can improve the efficacy of T-cell priming and induce adaptive anti-tumor immunity once introduced into the cancer environment. Conversely, other cytokines have been associated with poor patient outcomes, and have been reported to promote tumor growth and inhibit anti-tumor immune response. For example, imbalanced production of interleukin 6 (IL-6), vascular endothelial growth factor (VEGF), or macrophage colony-stimulating factor (M-CSF) inhibit adaptive anti-tumor immunity by suppressing dendritic cell maturation and activating regulatory T cells (Treg) to aid tumor cells in evading immune-surveillance. Transforming growth factor beta (TGF-β), which is abundantly expressed in many pathological conditions, heavily influences tumor growth and maintenance, as the cytokine has an important role in forming a tumor microenvironment and facilitating angiogenesis. Applying the teachings of the present disclosure, accurate measures of the preceding immunological cytokine actors at the single-cell level, across multiple cells and cell populations/samples may be conducted. Cytokine secretion profiles for individual cells or collections of cells may be further evaluated and compared to existing information and literature vales to create actionable patient immunological profiles and/or provide indicators or correlates of immune response and functional activation against cancers.

In other applications, polyfunctionality for diseased cells such as malignant hematological cells or solid tumor cells may be evaluated on the basis of cytokine secretions with various secretion profiles correlated with pathogenesis. Cytokines that may be analyzed may include by way of example, CCl-11, GM-CSF, Granzyme B, IFN-γ, IL-10, IL-12, IL-13, IL-17A, IL-17F, IL-18, IL-1β, IL-2, IL-21, IL-22, IL-4, IL-5, IL-6, IL-7, IL-8, IL-9, IP-10, MCP-1, MCP-4, MIP-1α, MIP-1β, Perforin, RANTES, sCD137, sCD40L, TGF-β1, TNF-α, TNF-β. Additionally, the system and methods of the present disclosure may be desirably applied in various clinical applications where characterization of effector function across wide spectra or populations of single cells, for example, in areas of cellular immunity and oncology tools is beneficial for accurate diagnosis or therapeutic evaluation.

While the principles of the disclosure have been illustrated in relation to the exemplary embodiments shown herein, the principles of the disclosure are not limited thereto and include any modification, variation or permutation thereof. Further, the examples set forth above are provided to give those of ordinary skill in the art a complete disclosure and description of how to make and use the embodiments of the devices, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains.

The terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. A number of embodiments of the disclosure have been described. Nevertheless, it will be understood that various modifications may be made without departing from the spirit and scope of the present disclosure. Accordingly, other embodiments are within the scope of the following claims.

What is claimed is:

1. A system for discretely resolving analytes associated with a cellular population comprising:
   a plurality of sample retention regions that receive at least one cell distributed from a population of cells and retain an associated plurality of analytes released by the at least one cell;
   a plurality of analyte detection regions patterned with a plurality of discretely positioned analyte detection moieties, the analyte detection regions disposed along parallel lines forming a barcode pattern alignable with the sample retention regions whereby, upon coupling, released analytes selectively associate with the plurality of analyte detection moieties forming an analyte barcode pattern for each analyte detection region;
   a plurality of first alignment markers disposed about the plurality of sample retention regions and a plurality of second alignment markers disposed about the plurality of analyte detection regions;
   an imaging apparatus that generates a plurality of images for selected sample retention regions and retained at least one cell and additionally at least one first alignment marker, the imaging apparatus further generating a plurality of images for analyte detection regions corresponding to the selected sample regions and associated analyte barcode patterns and additionally at least one second alignment marker; and
   an image processor that aligns associated images for selected sample retention regions using the at least one first alignment marker and further aligns images for analyte detection regions with corresponding images for selected sample retention regions using the at least one second alignment marker, the image processor further identifying retained at least one cell in respective sample retention regions and corresponding analyte barcode patterns to discretely resolve released analytes associated with the retained at least one cell based on the analyte detection moieties detected in the analyte barcode pattern.

2. The system of claim 1, wherein the image processor further evaluates the sample retention region images to determine image characteristics for associated sample retention regions.

3. The system of claim 2, wherein the image processor gates resolution of analytes and cellular associations based on the image characteristics of the sample retention regions.

4. The system of claim 1, wherein the image processor further evaluates the sample retention region images to determine image characteristics for the retained at least one cell.

5. The system of claim 4, wherein the system further comprises a cell template database including a plurality of cell images accessed by the image processor to identify the retained at least one cell by comparison of image characteristics with the plurality of cell images.

6. The system of claim 5, wherein the image processor identifies the retained at least one cell on the basis of similarity of image characteristics with at least one cell image in the cell template database.

7. The system of claim 1, wherein the at least one cell is labelled with at least one antibody, stain or dye that identifies the presence of at least one surface marker in at least one of the plurality of images is used by the image processor for cellular identification.

8. The system of claim 7, wherein the at least one labelled cell detected in at least one of the plurality of images is used by the image processor to discriminate between different types of cells.

9. The system of claim 1, wherein the at least one cell is labelled with a stain or dye detected in at least one of the plurality of images identifies cells as live or dead or highlights metabolic processes of cells.

10. The system of claim 1, wherein at least two or more discrete regions of the analyte barcode pattern associated with selected at least one cell are evaluated by the image processor to resolve released analytes for the selected at least on cell.

11. The system of claim 1, wherein the image processor further performs a background intensity determination for an image having at least one selected sample retention region lacking a corresponding retained cell.

12. The system of claim 11, wherein the image processor compares the determined background intensity to an intensity associated with a region of the analyte barcode pattern associated with selected at least one cell to be evaluated to resolve released analytes for the selected at least one cell.

13. The system of claim 1, wherein the image processor further identifies sample retention chambers retaining single cells and compares the discretely resolved released analytes for the single cells to reflect a distribution of detected analytes for the population of cells.

14. The system of claim 13, wherein the distribution of detected analytes for the population of cells characterizes polyfunctional ability of single cells from the population of cells to release multiple analytes.

15. The system of claim 13, further comprising an analyte response database comprising analyte profiles for patient, therapeutic, or disease response associated with selected analytes wherein the image processor compares the distribution of detected analytes for the population of cells to the analyte response database to correlate detected released analytes in the population of cells with the analyte profiles in the analyte response database.

16. The system of claim 1, wherein the analytes are selected from the group consisting of biomolecules, organic molecules, inorganic molecules, nucleic acids, peptides, proteins, antibodies, cytokines, chemokines, and ions.

17. The system of claim 1, wherein the analytes comprise cytokines or proteins secreted by the at least one cell from the population of cells and are selected from the group consisting of CCl-11, GM-CSF, Granzyme B, IFN-$\gamma$, IL-10, IL-12, IL-13, IL-17A, IL-17F, IL-18, IL-1$\beta$, IL-2, IL-21, IL-22, IL-4, IL-5, IL-6, IL-7, IL-8, IL-9, IP-10, MCP-1, MCP-4, MIP-1$\alpha$, MIP-1$\beta$, Perforin, RANTES, sCD137, sCD40L, TGF-$\beta$1, TNF-$\alpha$, and TNF-$\beta$.

18. The system of claim 1, wherein the cells are selected from the group consisting of B-cells, T cells, CD4+ cells, CD8+ cells, macrophage cells, dendritic cells, epithelial cells, brain cells, tumor cells, malignant cells and diseased cells.

19. A method for discretely resolving analytes associated with a cellular population comprising:
acquiring a plurality of images for a plurality of sample retention regions that receive at least one cell distributed from a population of cells and retain an associated plurality of analytes released by the at least one cell;
acquiring a plurality of images for a plurality of analyte detection regions patterned with a plurality of discretely positioned analyte detection moieties, the analyte detection regions disposed along parallel lines forming a barcode pattern alignable with the sample retention regions whereby, upon coupling, released analytes selectively associate with the plurality of analyte detection moieties forming an analyte barcode pattern for each analyte detection region;
resolving a plurality of first alignment markers disposed about the plurality of sample retention regions;
resolving a plurality of second alignment markers disposed about the plurality of analyte detection regions;
aligning associated images for selected sample retention regions using at least one of the plurality of first alignment markers and further aligning images for analyte detection regions with corresponding images for selected sample retention regions using the at least one of the plurality of second alignment markers; and
identifying retained at least one cell in respective sample retention regions and corresponding analyte barcode patterns to discretely resolve released analytes associated with the retained at least one cell based on the analyte detection moieties detected in the analyte barcode pattern.

20. One or more non-transitory computer-readable media having computer executable code stored thereon for discretely resolving analytes associated with a cellular population, the code comprising:
an executable routine for acquiring a plurality of images for a plurality of sample retention regions that receive at least one cell distributed from a population of cells and retain an associated plurality of analytes released by the at least one cell;
an executable routine for acquiring a plurality of images for a plurality of analyte detection regions patterned with a plurality of discretely positioned analyte detection moieties, the analyte detection regions disposed along parallel lines forming a barcode pattern-alignable with the sample retention regions whereby, upon coupling, released analytes selectively associate with the plurality of analyte detection moieties forming an analyte barcode pattern for each analyte detection region;
an executable routine for resolving a plurality of first alignment markers disposed about the plurality of sample retention regions;
an executable routine for resolving a plurality of second alignment markers disposed about the plurality of analyte detection regions;
an executable routine for aligning associated images for selected sample retention regions using at least one of the plurality of first alignment markers and further aligning images for analyte detection regions with corresponding images for selected sample retention regions using the at least one of the plurality of second alignment markers; and
an executable routine for identifying retained at least one cell in respective sample retention regions and corresponding analyte barcode patterns to discretely resolve released analytes associated with the retained at least one cell based on the analyte detection moieties detected in the analyte barcode pattern.

* * * * *